US009089476B2

(12) United States Patent
Soula et al.

(10) Patent No.: US 9,089,476 B2
(45) Date of Patent: Jul. 28, 2015

(54) INJECTABLE SOLUTION AT PH 7 COMPRISING AT LEAST ONE BASAL INSULIN WHOSE PI IS BETWEEN 5.8 AND 8.5

(75) Inventors: Olivier Soula, Meyzieu (FR); Gerard Soula, Meyzieu (FR); Jeff Tonnar, Lyons (FR); Alexandre Geissler, Lyons (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 13/571,026

(22) Filed: Aug. 9, 2012

(65) Prior Publication Data

US 2013/0065826 A1 Mar. 14, 2013

Related U.S. Application Data

(60) Provisional application No. 61/522,031, filed on Aug. 10, 2011, provisional application No. 61/579,966, filed on Dec. 23, 2011.

(30) Foreign Application Priority Data

Aug. 10, 2011 (FR) ...................................... 11 57291
Dec. 23, 2011 (FR) ...................................... 11 62445

(51) Int. Cl.
*A61K 38/28* (2006.01)
*A61K 9/08* (2006.01)
*A61K 9/00* (2006.01)

(52) U.S. Cl.
CPC ................ *A61K 9/0019* (2013.01); *A61K 9/08* (2013.01); *A61K 38/28* (2013.01)

(58) Field of Classification Search
None
See application file for complete search history.

(56) References Cited

U.S. PATENT DOCUMENTS

| | | | |
|---|---|---|---|
| 2,387,201 A | 10/1945 | Weiner | |
| 4,826,818 A | 5/1989 | Mori et al. | |
| 5,656,722 A | 8/1997 | Dörschug | |
| 6,100,376 A | 8/2000 | Dörschug | |
| 7,226,618 B1 | 6/2007 | Touraud et al. | |
| 7,718,609 B2 | 5/2010 | Steiner et al. | |
| 8,426,382 B2 * | 4/2013 | Soula et al. | 514/8 |
| 2003/0225033 A1 | 12/2003 | Groman et al. | |
| 2006/0099264 A1 | 5/2006 | Chan et al. | |
| 2006/0188555 A1 | 8/2006 | Cormier et al. | |
| 2007/0196497 A1 | 8/2007 | Pouliquen et al. | |
| 2008/0014250 A1 | 1/2008 | Soula et al. | |
| 2008/0026070 A1 | 1/2008 | Bonnet-Gonnet | |
| 2008/0039368 A1 | 2/2008 | Steiner et al. | |
| 2009/0011028 A1 | 1/2009 | Checot et al. | |
| 2009/0048412 A1 | 2/2009 | Soula et al. | |
| 2009/0110742 A1 | 4/2009 | Constancis et al. | |
| 2009/0304665 A1 * | 12/2009 | Frost et al. | 424/94.5 |
| 2010/0167984 A1 | 7/2010 | Soula et al. | |
| 2010/0167991 A1 * | 7/2010 | Soula et al. | 514/8 |
| 2010/0249020 A1 | 9/2010 | Soula et al. | |
| 2011/0172166 A1 | 7/2011 | Charvet et al. | |
| 2011/0178011 A1 | 7/2011 | Soula et al. | |
| 2011/0195913 A1 | 8/2011 | Charvet et al. | |
| 2011/0212901 A1 | 9/2011 | Akiyoshi et al. | |
| 2012/0295833 A1 | 11/2012 | Charvet et al. | |
| 2012/0309680 A1 | 12/2012 | Charvet et al. | |
| 2013/0065826 A1 | 3/2013 | Soula et al. | |
| 2013/0178415 A1 | 7/2013 | Soula | |
| 2014/0187499 A1 | 7/2014 | Soula et al. | |
| 2014/0378373 A2 | 12/2014 | Soula et al. | |
| 2015/0025005 A1 | 1/2015 | Langer et al. | |

FOREIGN PATENT DOCUMENTS

| | | |
|---|---|---|
| AU | 2007/255367 B2 | 12/2007 |
| EP | 1 222 926 | 7/2002 |
| EP | 2 360 188 A1 | 8/2011 |
| EP | 2 387 989 A2 | 11/2011 |
| FR | 2 801 226 A1 | 5/2001 |
| FR | 2 840 614 A1 | 12/2003 |
| FR | 2 862 536 A1 | 5/2005 |
| FR | 2 985 428 A1 | 7/2013 |
| FR | 2 985 429 A1 | 7/2013 |
| WO | WO 03/053339 A2 | 7/2003 |
| WO | WO 2004/060968 A1 | 7/2004 |
| WO | WO 2004/096854 A2 | 11/2004 |
| WO | 2006/051103 A2 | 5/2006 |
| WO | WO 2007/116143 A1 | 10/2007 |
| WO | WO 2007/121256 A2 | 10/2007 |
| WO | WO 2007/141344 A2 | 12/2007 |
| WO | WO 2008/030119 A1 | 3/2008 |
| WO | WO 2009/021955 A1 | 2/2009 |
| WO | WO 2009/063072 A2 | 5/2009 |
| WO | WO 2010/041138 A2 | 4/2010 |
| WO | WO 2010/053140 A1 | 5/2010 |
| WO | WO 2010/056403 A1 | 5/2010 |
| WO | WO 2010/122385 A1 | 10/2010 |
| WO | WO 2011/077405 A1 | 6/2011 |
| WO | WO 2011/098962 A2 | 8/2011 |
| WO | WO 2011/144673 A2 | 11/2011 |
| WO | WO 2011/144676 A1 | 11/2011 |
| WO | WO 2011/147980 A1 | 12/2011 |
| WO | WO 2012/153070 | 11/2012 |
| WO | WO 2013/021143 A1 | 2/2013 |
| WO | WO 2013/104861 A1 | 7/2013 |

OTHER PUBLICATIONS

International Search Report dated Dec. 3, 2012 issued in International Application No. PCT/FR2012/051880.

(Continued)

*Primary Examiner* — Karlheinz R Skowronek
*Assistant Examiner* — Joseph Fischer
(74) *Attorney, Agent, or Firm* — Oliff PLC

(57) ABSTRACT

A composition in the form of an injectable aqueous solution, the pH of which is between 6.0 and 8.0, includes at least a basal insulin, the isoelectric point pI of which is between 5.8 and 8.5; and a dextran substituted by radicals carrying carboxylate charges and hydrophobic radicals. Single-dose formulations at a pH of between 7 and 7.8 includes a basal insulin whose isoelectric point is between 5.8 and 8.5 and a prandial insulin.

25 Claims, 6 Drawing Sheets

(56) References Cited

OTHER PUBLICATIONS

Cengiz et al., Abstract of "Should We Mix Lispro with Glargine? Removing the Guesswork by Euglycemic Clamp Studies," *69th Annual Scientific Sessions of the American Diabetes Association (ADA)*, Abstract No. 19-OR, 2009.
Cengiz et al., "Early Pharmacokinetic and Pharmacodynamic Effects of Mixing Lispro With Glargine Insulin: Results of glucose clamp studies in youth with type I diabetes," *Diabetes Care*, May 2010, pp. 1009-1012, vol. 33, No. 5.
Testa et al., Abstract of "Patient Satisfaction, Quality of Life and Glycemic Variability in Type 1 and 2 Diabetes: A Cross-Over Trial of Insulin Glargine + Glulisine vs Premix Analog Insulin," *70th Annual Scientific Sessions of the American Diabetes Association (ADA)*, Abstract No. 2163-PO, 2010.
Testa et al., Abstract of "Decreased Glycemic Variability during Insulin Therapy Improves Patient-Centered Outcomes in Type 1 and 2 Diabetes," *70th Annual Scientific Sessions of the American Diabetes Association (ADA)*, Abstract No. 1-LB, 2010.
Sanchez-Chaves et al., "Poly (vinyl alcohol) functionalized by monosuccinate groups. Coupling of bioactive amino compounds," *Polymer*, 1998, pp. 2751-2757, vol. 39, No. 13.
French Search Report issued in French Application No. 1157291 dated Mar. 23, 2012 (w/translation).
Draft Prescribing Information concerning LANTUS®; Apr. 20, 2000; pp. 1-14.
McKeage et al.; "Insulin Glargine—A Review of its Therapeutic Use as a Long-Acting Agent for the Management of Type 1 and 2 Diabetes Mellitus;" *Drugs*; 2001; pp. 1599-1624; vol. 61, No. 11; Adis International Limited.
U.S. Office Action dated Oct. 23, 2014 from U.S. Appl. No. 13/737,353.
"Improved Outcomes for Patients Treated with Lantus® and Apidra® Regimen Compared with Sliding Scale Insulin;" Sanofi-Aventis Press Release; Jun. 25, 2010; Paris, France.
Uehata et al., "Effect of sulfobutyl ether-β-cyclodextrin on bioavailability of insulin glargine and blood glucose level after subcutaneous injection to rats," International Journal of Pharmaceutics, pp. 1-6, 2011.
Deming, "Polypeptide and Polypeptide Hybrid Copolymer Synthesis via NCA Polymerization," Adv Polm Sci, vol. 202, pp. 1-18, 2006.
Deming, "Facile synthesis of block copolypeptides of defined architecture," Nature, vol. 390, pp. 386-389, Nov. 27, 1997.
Lu et al., "Hexamethyldisilazane-Mediated Controlled Polymerization of α-Amino Acid N-Carboxyanhydrides," J. Am. Chem. Soc., vol. 129, pp. 14114-14115, 2007.
Lu et al., "N-Trimethylsilyl Amines for Controlled Ring-Opening Polymerization of Amino Acid N-Carboxyanhydrides and Facile End Group Functionalization of Polypeptides," J. Am. Chem. Soc., vol. 130, pp. 12562-12563, 2008. (with supporting Information pp. S1-S8).
Huile et al., "Controlled Release of Insulin From Nanoparticles of Amphiphilic Block Copolyamino Acid," Journal of Controlled Release, vol. 64, pp. 319-321, 2000.
"Byetta® Approved for Use with Insulin Glargine in the U.S.: Patients in Pivotal Study Achieved Better Glycemic Control Without Weight Gain or Increased Hypoglycemia Risk Versus Insulin Glargine" Amylin Pharmaceuticals, Inc. and Eli Lilly and Company, XP-002686281, Oct. 19, 2011.
"Highlights of Prescribing Information and Full Prescribing Information for Lantus," © 2009 sanofi-aventis U.S. LLC. Revised Jun. 2009, 24 pages.
Dubowchik et al.; "Improved Cytotoxicity of Antitumor Compounds Deliverable by the LDL Pathyway[1,2];" Biocoalugate Chem.; 1995; pp. 427-439; vol. 6.
Smoot et al.; "Oligosaccharide Synthesis: From Conventional Methods to Modern Expeditious Strategies;" Advances in Carbohydrate Chemistry and Biochemistry; 2009; pp. 161-250; vol. 62.
Lindhorst; Essentials of Carbohydrate Chemistry and Biochemistry; 2007; pp. 157-208.
Takata et al.; "Prodrugs of Vitamin E. 1. Preparation and Enzymatic Hydrolysis of Aminoalkanecarboxylic Acid Esters of d-a-Tocopherol;" Journal of Pharmaceutical Sciences; Jan. 1995; pp. 96-100; vol. 84, No. 1.
A. Magnani et al., "Novel Polysaccharide Hydrogels: Characterization and Properties." Polymers for Advanced Technologies, vol. 11, 2000, p. 488-495.
M. I. Papisov et al, "Semisynthetic Hydrophilic Polyals." Biomacromolecules, vol. 6, 2005, p. 2659-2670.
A. Yurkovetskiy et al., "Fully Degradable Hydrophilic Polyals for Protein Modification." Biomacromolecules, 2005, vol. 6, p. 2648-2658.
A. V. Yurkovetskiy et al., "Synthesis of a Macromolecular Camptothecin Conjugate with Dual Phase Drug Release." Molecular Pharmaceutics, 2004, vol. 1 No. 5, p. 375-382.
M. I. Papisov, "Acyclic Polyacetals from Polysaccharides: Biomimetic Biomedical "Stealth" Polymers." Biopolymers from Polysaccharides and Agroproteins, 2001, Chapter 19, p. 301-314.
M. Baudys et al, "Extending Insulin Action in Vivo by Conjugation to Carboxymethyl Dextran." Bioconjugate Chem, vol. 9, 1998, p. 176-183.
M. F. Ishak and Painter, T., "Kinetic Evidence for Hemiacetal Formation During the Oxidation of Dextran in Aqueous Periodate." Carbohydrate Research, vol. 64, 1978, p. 189-197.
U.S. Appl. No. 13/737,353, filed Jan. 9, 2013.
U.S. Appl. No. 14/179,212, filed Feb. 12, 2014.
U.S. Appl. No. 14/179,042, filed Feb. 12, 2014.
Dec. 20, 2013 Office Action issued in U.S. Appl. No. 13/737,353.
ICI Americas Inc., "The HLB System, a time-saving guide to emulsifier selection," 1980, pp. 1-22.
Package insert for Neut® Sodium Bicarbonate Additive Solution, Publication EN-0545, Hospira Corporation, revised Nov. 2004, pp. 1-4.
Apr. 20, 2015 Office Action issued in U.S. Appl. No. 14/179,212.

* cited by examiner

INJECTABLE SOLUTION AT PH 7 COMPRISING AT LEAST ONE BASAL INSULIN WHOSE PI IS BETWEEN 5.8 AND 8.5

The invention relates to therapies by injection of insulin(s) for treating diabetes.

Insulin therapy, or diabetes therapy by injecting insulin, has made remarkable progress in recent years by virtue especially of the development of novel insulins that offer correction of patients' glycaemia, which enables better simulation of the physiological activity of the pancreas.

To cover his daily insulin needs, a diabetic patient currently has available, schematically, two types of insulin with complementary actions: prandial insulins (or rapid-acting insulins) and basal insulins (or slow-acting insulins).

Prandial insulins allow rapid management (metabolization and/or storage) of the glucose provided by meals and snacks. The patient must inject a prandial insulin before each food intake, i.e. about 2 to 3 injections per day. The prandial insulins most commonly used are: the recombinant human insulin, NovoLog® (insulin aspart from Novo Nordisk), Humalog® (insulin lispro from Eli Lilly) and Apidra® (insulin glulisine from Sanofi-Aventis).

Basal insulins maintain the patient's glycaemic homeostasis, outside periods of food intake. They act essentially by blocking the endogenous production of glucose (hepatic glucose). The daily dose of basal insulin generally corresponds to 40-50% of the total daily insulin needs. Depending on the basal insulin used, this dose is dispensed in 1 or 2 injections, regularly distributed throughout the day. The basal insulins most commonly used are Levemir® (insulin detemir from Novo Nordisk) and Lantus® (insulin glargine from Sanofi-Aventis).

It will be noted, for the sake of completeness, that NPH (NPH insulin, for Neutral Protamine Hagedorn; Humuline NPH®, Insulatard®) is the oldest basal insulin. This formulation is the result of a precipitation of human insulin (anionic at neutral pH) with a cationic protein, protamine. These microcrystals are dispersed in an aqueous suspension and dissolve slowly after subcutaneous injection. This slow dissolution ensures sustained release of the insulin. However, this release does not ensure a constant concentration of insulin over time. The release profile is bell-shaped and lasts only between 12 and 16 hours. It is thus injected twice a day. This NPH basal insulin is much less efficient than the modern basal insulins Levemir® and Lantus®. NPH is an intermediate-acting basal insulin.

The principle of NPH changed with the appearance of rapid insulin analogues to give "Premix" products that afford both rapid action and intermediate action. NovoLog Mix® (Novo Nordisk) and Humalog Mix® (Eli Lilly) are formulations comprising a rapid insulin analogue, Novolog® and Humalog®, partially complexed with protamine. These formulations thus contain microcrystals of insulin whose action is said to be intermediate, and a proportion of insulin which has remained soluble, whose action is rapid. These formulations do indeed offer the advantage of a rapid insulin, but they also have the defect of NPH, i.e. a duration of action limited to between 12 and 16 hours and a bell-shaped release of insulin. However, these products enable the patient to carry out a single injection of an intermediate-acting basal insulin with a rapid-acting prandial insulin. In point of fact, many patients are desirous to reduce their number of injections.

The basal insulins currently marketed and currently under clinical development may be categorized as a function of the technical solution for obtaining sustained action, and two approaches are used at the present time.

The first, that of insulin detemir, is the binding to albumin in vivo. It is an analogue, soluble at pH 7, which comprises a fatty acid (tetradecanoyl) side chain attached to position B29 which, in vivo, enables this insulin to combine with albumin. Its sustained action is mainly due to this affinity for albumin after subcutaneous injection.

However, its pharmacokinetic profile does not make it possible to cover a whole day, which means that it is usually used in two injections per day.

Other basal insulins which are soluble at pH 7, such as Degludec®, are currently under development. Degludec® also comprises a fatty acid side chain attached to insulin (hexadecandioyl-γ-L-Glu).

The second, that of insulin glargine, is the precipitation at physiological pH. This is an analogue of human insulin obtained by elongation of the C-terminal part of the B chain of human insulin with two arginine residues, and by substitution of the asparagine residue A21 with a glycine residue (U.S. Pat. No. 5,656,722). The addition of the two arginine residues was conceived to adjust the pI (isoelectric point) of insulin glargine at physiological pH, and thus make this insulin analogue insoluble in physiological medium.

The substitution of A21 was conceived in order to make insulin glargine stable at acidic pH and thus to be able to formulate it in the form of an injectable solution at acidic pH. During subcutaneous injection, the passage of insulin glargine from an acidic pH (pH 4-4.5) to a physiological pH (neutral pH) brings about its precipitation under the skin. The slow redissolution of the insulin glargine microparticles ensures a slow and sustained action.

The hypoglycaemic effect of insulin glargine is virtually constant over a period of 24 hours, which allows the majority of patients to limit themselves to a single injection per day.

Insulin glargine is nowadays considered as the best basal insulin marketed.

However, the acidic pH of the formulations of basal insulins, the isoelectric point of which is between 5.8 and 8.5, of insulin glargine type, prevents any pharmaceutical combination with other proteins and in particular prandial insulins, since the latter are unstable at acidic pH.

However, no one has hitherto sought to dissolve these basal insulins, the isoelectric point of which is between 5.8 and 8.5, of insulin glargine type, at neutral pH, while maintaining a difference in solubility between the in vitro medium (containing it) and the in vivo medium (under the skin), independently of the pH.

Specifically, the operating principle of basal insulins, of insulin glargine type, outlined above, namely that they are soluble at acidic pH and precipitate at physiological pH, dissuades a person skilled in the art from any solution in which insulin of insulin glargine type would be dissolved at pH 6-8 while maintaining its essential property, which is that of precipitating in subcutaneous medium.

Furthermore, the impossibility of formulating a prandial insulin, at acidic pH, arises from the fact that a prandial insulin undergoes, under these conditions, a deamidation side reaction in position A21; this does not make it possible to satisfy the requirement of the US Pharmacopeia, namely less than 5% of by-product after 4 weeks at 30° C.

Furthermore, this acidic pH of formulations of basal insulins, the isoelectric point of which is between 5.8 and 8.5, of insulin glargine type, even prevents any extemporaneous combination with prandial insulins at neutral pH.

A recent clinical study, presented at the 69th Scientific Sessions of the American Diabetes Association, New Orleans, La., 5-9 Jun. 2009, verified this limitation of use of insulin glargine. A dose of insulin glargine and a dose of prandial insulin (in the case in point, insulin lispro) were mixed together just before injection (E. Cengiz et al., 2010, Diabetes Care, 33(5), 1009-12). This experiment made it possible to demonstrate a significant delay in the pharmacokinetic and pharmacodynamic profiles of prandial insulin, which may give rise to postprandial hyperglycaemia and to nocturnal hypoglycaemia. This study indeed confirms the incompatibility of insulin glargine with the currently marketed rapid-acting insulins.

Moreover, the instructions for use for Lantus®, the commercial product based on insulin glargine from the company Sanofi-Aventis, explicitly indicates to users that they should not mix it with a solution of prandial insulin, whichever it may be, on account of the serious risk of modifying the pharmacokinetics and pharmacodynamics of the insulin glargine and/or of the mixed prandial insulin.

However, from a therapeutic point of view, clinical studies made public during the 70th annual scientific sessions of the American Diabetes Association (ADA) of 2010, abstract 2163-PO and abstract number 0001-LB, in particular those conducted by the company Sanofi-Aventis, showed that treatments which combine Lantus®, insulin glargine, and a prandial insulin are much more efficient than treatments based on products of the "Premix", Novolog Mix® or Humalog Mix® type.

As regards combinations of insulin glargine and rapid insulin, the company Biodel has notably described, in U.S. Pat. No. 7,718,609, compositions comprising a basal insulin and a prandial insulin at a pH of between 3.0 and 4.2 in the presence of a chelating agent and polyacids. This patent teaches how to make a prandial insulin compatible at acidic pH in the presence of an insulin of insulin glargine type. It does not teach how to prepare a combination of insulin of insulin glargine type and of a prandial insulin at neutral pH.

From the analysis of the compositions described in the literature and the patents, it appears that the insolubility at pH 7 of basal insulins of the insulin glargine type is a prerequisite for having its slow action. As a result, all the solutions proposed for combining them with other products, such as prandial insulins, are based on tests of dissolution or stabilization of prandial insulins at acidic pH; see, for example, WO 2007/121256 and WO 2009/021955.

Surprisingly, the compositions according to the invention make it possible to dissolve, at pH 7, a basal insulin whose isoelectric point is between 5.8 and 8.5.

Surprisingly, the compositions according to the invention allow maintenance of the duration of the hypoglycaemic activity of the basal insulin whose isoelectric point is between 5.8 and 8.5, despite its dissolution at pH 7 before injection. This noteworthy property arises from the fact that the insulin of insulin glargine type dissolved at pH 7 in the composition of the invention precipitates in subcutaneous medium by means of a change of composition of the medium. The factor triggering the precipitation of the insulin of insulin glargine type is no longer the pH modification, but a modification of composition of the environment during the passage of the pharmaceutical composition into the physiological medium.

By solving this problem of solubility at pH 7, the present invention makes it possible:

to propose an injectable composition, intended for treating diabetes, comprising a basal insulin whose isoelectric point is between 5.8 and 8.5, in the form of a homogeneous solution at pH 7, while retaining its biological activity and its action profile;

to propose a composition in the form of a formulation comprising a combination of a basal insulin whose isoelectric point is between 5.8 and 8.5 and a prandial insulin without modification of the activity profile of the prandial insulin which is soluble at pH 6-8 and unstable at acidic pH, while maintaining the basal action profile intrinsic to the basal insulin;

to propose an injectable composition, intended for treating diabetes, additionally comprising a combination of a basal insulin whose isoelectric point is between 5.8 and 8.5 and a derivative or an analogue of a gastrointestinal hormone such as GLP-1 or "glucagon-like peptide-1";

for patients to reduce their number of injections;

for the said compositions to satisfy the requirements of the American Pharmacopeia and European Pharmacopoeia.

Surprisingly, in insulin combinations of insulin glargine type with a prandial insulin, which are subject-matters of the invention, the rapid action of the prandial insulin is preserved despite the precipitation of the insulin of insulin glargine type in subcutaneous medium.

The invention relates to a composition in the form of an injectable aqueous solution, the pH of which is between 6.0 and 8.0, comprising at least:

a) a basal insulin, the isoelectric point pI of which is between 5.8 and 8.5;

b) a dextran substituted by radicals carrying carboxylate charges and hydrophobic radicals of formula I or of formula II:

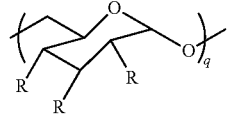

Formula I in which:

R is —OH or chosen from the group consisting of the radicals:

-(f-[A]-COOH)$_n$;

-(g-[B]-k-[D])$_m$, D comprising at least one alkyl chain comprising at least 8 carbon atoms;

n represents the degree of substitution of the glucoside units by -f-[A]-COOH and $0.1 \leq n \leq 2$;

m represents the degree of substitution of the glucoside units by -g-[B]-k-[D] and $0 < m \leq 0.5$;

q represents the degree of polymerization as glucoside units, that is to say the mean number of glucoside units per polysaccharide chain, and $3 \leq q \leq 50$;

-(f-[A]-COOH)$_n$:

-A- is a linear or branched radical comprising from 1 to 4 carbon atoms; the said -A- radical:

being bonded to a glucoside unit via a functional group f chosen from the group consisting of ether, ester and carbamate functional groups;

-(g-[B]-k-[D])$_m$:

—B— is a linear or branched, at least divalent, radical comprising from 1 to 4 carbon atoms; the said —B— radical:

being bonded to a glucoside unit via a functional group g chosen from the group consisting of ether, ester and carbamate functional groups;

being bonded to a -D radical via a functional group k; k chosen from the group consisting of ester, amide and carbamate functional groups; the said -D radical:

being an —X(-l-Y)$_p$ radical, X being an at least divalent radical comprising from 1 to 12 atoms chosen from the group consisting of C, N and O atoms, optionally carrying carboxyl or amine functional groups and/or resulting from an amino acid, a dialcohol, a diamine or a mono- or polyethylene glycol mono- or diamine; Y being a linear or cyclic alkyl group, an alkylaryl or an arylalkyl, of 8 to 30 carbon atoms, optionally substituted by one or more $C_1$ to $C_3$ alkyl groups; $p \geq 1$ and l a functional group chosen from the group consisting of ester, amide and carbamate functional groups;

f, g and k being identical or different;

the free acid functional groups being in the form of salts of alkali metal cations chosen from the group consisting of $Na^+$ and $K^+$;

and, when $p=1$, if Y is a $C_8$ to $C_{14}$ alkyl, then $q*m \geq 2$, if Y is a $C_{15}$ alkyl, then $q*m \geq 2$; and if Y is a $C_{16}$ to $C_{20}$ alkyl, then $q*m \geq 1$;

and, when $p \geq 2$, if Y is a $C_8$ to $C_9$ alkyl, then $q*m \geq 2$ and, if Y is a $C_{10}$ to $C_{16}$ alkyl, then $q*m \geq 0.2$;

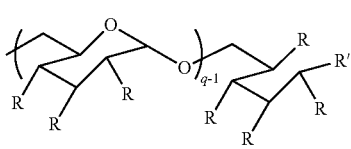

Formula II in which:

R is —OH or a -(f-[A]-COOH)$_n$ radical:
  -A- is a linear or branched radical comprising from 1 to 4 carbon atoms; the said radical -A-:
  being bonded to a glucoside unit via a functional group f chosen from the group consisting of ether, ester or carbamate functional groups;
  n represents the degree of substitution of the glucoside units by -f-[A]-COOH and $0.1 \leq n \leq 2$;

R' is chosen from the group consisting of the radicals:
  —C(O)NH-[E]-(o-[F])$_t$;
  —CH$_2$N(L)$_z$-[E]-(o-[F])$_t$;

in which:
  z is a positive integer equal to 1 or 2,
  L is chosen from the group consisting of:
    —H and z is equal to 1, and/or
    -[A]-COOH and z is equal to 1 or 2, if f is an ether functional group,
    —CO-[A]-COOH and z is equal to 1 if f is an ester functional group;
    —CO—NH-[A]-COOH and z is equal to 1 if f is a carbamate functional group;
  -[E]-(o-[F])$_t$:
    -E- is a linear or branched, at least divalent, radical comprising from 1 to 8 carbon atoms and optionally comprising heteroatoms, such as O, N or S;
    —F— is a linear or cyclic alkyl group, an alkylaryl or an arylalkyl, of 12 to 30 carbon atoms, optionally substituted by one or more $C_1$ to $C_3$ alkyl groups;
    o is a functional group chosen from the group consisting of ether, ester, amide or carbamate functional groups;
    t is a positive integer equal to 1 or 2;

q represents the degree of polymerization as glucoside units, that is to say the mean number of glucoside units per polysaccharide chain, and $3 \leq q \leq 50$;

the free acid functional groups being in the form of salts of alkali metal cations chosen from the group consisting of $Na^+$ and $K^+$;

when $z=2$, the nitrogen atom is in the form of a quaternary ammonium.

In one embodiment, when $p=1$, if Y is a $C_{21}$ to $C_{30}$ group, then $q*m \geq 1$.

In one embodiment, when $p=1$, if Y is a $C_{21}$ to $C_{30}$ group, then $q*m \geq 0.1$.

In one embodiment, the -(f-[A]-COOH)$_n$ radical is such that:
  -A- is a radical comprising one carbon atom; the said -A- radical being bonded to a glucoside unit via a ether functional group f.

In one embodiment, the -(g-[B]-k-[D])$_m$ radical is such that:
  —B— is a radical comprising one carbon atom; the said —B— radical being bonded to a glucoside unit via an ether functional group g, and
  X is a radical resulting from an amino acid.

In one embodiment, the -(f-[A]-COOH)$_n$ radical is such that:
  -A- is a radical comprising one carbon atom; the said -A- radical being bonded to a glucoside unit via an ether functional group f, and
  the -(g-[B]-k-[D])$_m$ radical is such that:
    —B— is a radical comprising one carbon atom; the said —B— radical being bonded to a glucoside unit via an ether functional group g, and
    X is a radical resulting from an amino acid,
    k is an amide functional group.

In one embodiment, the dextran substituted by radicals carrying carboxylate charges and hydrophobic radicals is of formula III:

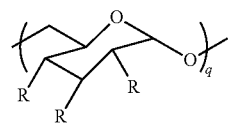

Formula III in which:

R is —OH or chosen from the group consisting of the radicals:
  -(f-[A]-COOH)$_n$;
  -(g-[B]-k-[D])$_m$, D comprising at least one alkyl chain comprising at least 8 carbon atoms;
  n represents the degree of substitution of the glucoside units by -f-[A]-COOH and $0.1 \leq n \leq 2$;
  m represents the degree of substitution of the glucoside units by -g-[B]-k-[D] and $0 < m \leq 0.5$;
  q represents the degree of polymerization as glucoside units, that is to say the mean number of glucoside units per polysaccharide chain, and $3 \leq q \leq 50$;

-(f-[A]-COOH)$_n$:
  -A- is a linear or branched radical comprising from 1 to 4 carbon atoms; the said -A- radical:
  being bonded to a glucoside unit via a functional group f chosen from the group consisting of ether, ester and carbamate functional groups;

-(g-[B]-k-[D])$_m$:
  —B— is a linear or branched, at least divalent, radical comprising from 1 to 4 carbon atoms; the said —B— radical:
  being bonded to a glucoside unit via a functional group g chosen from the group consisting of ether, ester and carbamate functional groups;

being bonded to a -D radical via a functional group k; k chosen from the group consisting of ester, amide and carbamate functional groups; the said -D radical:

being an —X(-l-Y)$_p$ radical, X being an at least divalent radical comprising from 1 to 12 atoms chosen from the group consisting of C, N and O atoms, optionally carrying carboxyl or amine functional groups and/or resulting from an amino acid, a dialcohol, a diamine or a mono- or polyethylene glycol mono- or diamine; Y being a linear or cyclic alkyl group, an alkylaryl or an arylalkyl, of 8 to 20 carbon atoms, optionally substituted by one or more $C_1$ to $C_3$ alkyl groups; p≥1 and l a functional group chosen from the group consisting of ester, amide and carbamate functional groups;

f, g and k being identical or different;

the free acid functional groups being in the form of salts of alkali metal cations chosen from the group consisting of $Na^+$ and $K^+$;

and, when p=1, if Y is a $C_8$ to $C_{14}$ alkyl, then q*m≥2, if Y is a $C_{15}$ alkyl, then q*m≥2; and if Y is a $C_{16}$ to $C_{20}$ alkyl, then q*m≥1;

and, when p≥2, if Y is a $C_8$ to $C_{11}$ alkyl, then q*m≥2 and, if Y is a $C_{12}$ to $C_{16}$ alkyl, then q*m≥0.3.

In one embodiment, the dextran substituted by radicals carrying carboxylate charges and hydrophobic radicals is of formula IV:

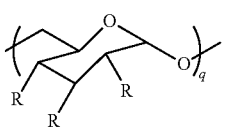

Formula IV in which:

R is —OH or chosen from the group consisting of the radicals:
-(f-[A]-COOH)$_n$;
-(g-[B]-k-[D])$_m$, D comprising at least one alkyl chain comprising at least 8 carbon atoms;

n represents the degree of substitution of the hydroxyl —OH functional groups by -f-[A]-COOH per glucoside unit; and 0.1≤n≤2;

m represents the degree of substitution of the hydroxyl —OH functional groups by -g-[B]-k-[D] per glucoside unit; and 0<m≤0.5;

q represents the degree of polymerization as glucoside units, that is to say the mean number of glucoside units per polysaccharide chain, and 3≤q≤50;

-(f-[A]-COOH)$_n$:
-A- is a linear or branched radical comprising from 1 to 4 carbon atoms; the said -A- radical:
being bonded to a glucoside unit via a functional group f chosen from the group consisting of ether, ester and carbamate functional groups;

-(g-[B]-k-[D])$_m$:
—B— is a linear or branched, at least divalent, radical comprising from 1 to 4 carbon atoms; the said —B— radical:
being bonded to a glucoside unit via a functional group g chosen from the group consisting of ether, ester and carbamate functional groups;
being bonded to a -D radical via a functional group k; k chosen from the group consisting of ester, amide and carbamate functional groups; the said -D radical:

being an —X(-l-Y)$_p$ radical, X being an at least divalent radical comprising from 1 to 12 atoms chosen from the group consisting of C, N and O atoms, optionally carrying carboxyl or amine functional groups and/or resulting from an amino acid, a dialcohol, a diamine or a mono- or polyethylene glycol mono- or diamine; Y being a linear or cyclic alkyl group, an alkylaryl or an arylalkyl, of 8 to 30 carbon atoms, optionally substituted by one or more $C_1$ to $C_3$ alkyl groups; p≥1 and l a functional group chosen from the group consisting of ester, amide and carbamate functional groups;

f, g and k being identical or different;

the free acid functional groups being in the form of salts of alkali metal cations chosen from the group consisting of $Na^+$ and $K^+$;

and, when p=1, if Y is a $C_8$ to $C_{14}$ alkyl, then q*m≥2, if Y is a $C_{15}$ alkyl, then q*m≥2; and if Y is a $C_{16}$ to $C_{30}$ alkyl, then q*m≥1;

and, when p≥2, if Y is a $C_8$ to $C_9$ alkyl, then q*m≥2 and, if Y is a $C_{10}$ to $C_{16}$ alkyl, then q*m≥0.2.

The structure drawn corresponds to the representation commonly used to represent dextran, which is a polysaccharide predominantly composed of (1,6) linkages between glucoside units, which is the representation adopted. Dextran also comprises (1,3) linkages at approximately 5% in general, which are deliberately not represented but which are, of course, included within the scope of the invention.

The term "basal insulin" whose isoelectric point is between 5.8 and 8.5 is understood to mean an insulin which is insoluble at pH 7 and which has a duration of action of between 8 and 24 hours or more in the standard models of diabetes.

These basal insulins whose isoelectric point is between 5.8 and 8.5 are recombinant insulins, the primary structure of which has been modified mainly by introduction of basic amino acids, such as arginine or lysine. They are described, for example, in the following patents, patent applications or publications: WO 2003/053339, WO 2004/096854, U.S. Pat. No. 5,656,722 and U.S. Pat. No. 6,100,376.

In one embodiment, the basal insulin whose isoelectric point is between 5.8 and 8.5 is insulin glargine.

In one embodiment, the compositions according to the invention comprise 100 IU/ml (i.e., approximately 3.6 mg/ml) of basal insulin whose isoelectric point is between 5.8 and 8.5.

In one embodiment, the compositions according to the invention comprise 40 IU/ml of basal insulin whose isoelectric point is between 5.8 and 8.5.

In one embodiment, the compositions according to the invention comprise 200 IU/ml of basal insulin whose isoelectric point is between 5.8 and 8.5.

In one embodiment, the compositions according to the invention comprise 300 IU/ml of basal insulin whose isoelectric point is between 5.8 and 8.5.

In one embodiment, the compositions according to the invention comprise 400 IU/ml of basal insulin whose isoelectric point is between 5.8 and 8.5

In one embodiment, the compositions according to the invention comprise 500 IU/ml of basal insulin whose isoelectric point is between 5.8 and 8.5.

In one embodiment, the ratio by weight of the basal insulin whose isoelectric point is between 5.8 and 8.5 to the substituted dextran, i.e. substituted dextran/basal insulin, is between 0.2 and 5.

In one embodiment, the ratio by weight of the basal insulin whose isoelectric point is between 5.8 and 8.5 to the substituted dextran, i.e. substituted dextran/basal insulin, is between 0.2 and 4.

In one embodiment, the ratio by weight of the basal insulin whose isoelectric point is between 5.8 and 8.5 to the substituted dextran, i.e. substituted dextran/basal insulin, is between 0.2 and 3.

In one embodiment, the ratio by weight of the basal insulin whose isoelectric point is between 5.8 and 8.5 to the substituted dextran, i.e. substituted dextran/basal insulin, is between 0.5 and 3.

In one embodiment, the ratio by weight of the basal insulin whose isoelectric point is between 5.8 and 8.5 to the substituted dextran, i.e. substituted dextran/basal insulin, is between 0.8 and 3.

In one embodiment, the ratio by weight of the basal insulin whose isoelectric point is between 5.8 and 8.5 to the substituted dextran, i.e. substituted dextran/basal insulin, is between 1 and 3.

In one embodiment, the concentration of substituted dextran is between 1 and 100 mg/ml.

In one embodiment, the concentration of substituted dextran is between 1 and 80 mg/ml.

In one embodiment, the concentration of substituted dextran is between 1 and 60 mg/ml.

In one embodiment, the concentration of substituted dextran is between 1 and 50 mg/ml.

In one embodiment, the concentration of substituted dextran is between 1 and 30 mg/ml.

In one embodiment, the concentration of substituted dextran is between 1 and 20 mg/ml.

In one embodiment, the concentration of substituted dextran is between 1 and 10 mg/ml.

In one embodiment, the concentration of polysaccharide is between 5 and 20 mg/ml.

In one embodiment, the concentration of polysaccharide is between 5 and 10 mg/ml.

In one embodiment, the compositions according to the invention additionally comprise a prandial insulin. Prandial insulins are soluble at pH 7.

The term "prandial insulin" is understood to mean a "rapid" or "regular" insulin.

"Rapid" prandial insulins are insulins which must meet the needs brought about by the ingestion of proteins and carbohydrates during a meal; they have to act in less than 30 minutes.

In one embodiment, "regular" prandial insulins are chosen from the group consisting of Humulin® (human insulin) and Novolin® (human insulin).

"Fast-acting" prandial insulins are insulins which are obtained by recombination and which are modified in order to reduce their action time.

In one embodiment, "fast-acting" prandial insulins are chosen from the group consisting of insulin lispro (Humalog®), insulin glulisine (Apidra®) and insulin aspart (NovoLog®).

In one embodiment, the compositions according to the invention comprise, in total, 100 IU/ml (i.e., approximately 3.6 mg/ml) of insulin with a combination of prandial insulin and basal insulin whose isoelectric point is between 5.8 and 8.5.

In one embodiment, the compositions according to the invention comprise, in total, 40 IU/ml of insulin with a combination of prandial insulin and basal insulin whose isoelectric point is between 5.8 and 8.5.

In one embodiment, the compositions according to the invention comprise, in total, 200 IU/ml of insulin with a combination of prandial insulin and basal insulin whose isoelectric point is between 5.8 and 8.5.

In one embodiment, the compositions according to the invention comprise, in total, 300 IU/ml of insulin with a combination of prandial insulin and basal insulin whose isoelectric point is between 5.8 and 8.5.

In one embodiment, the compositions according to the invention comprise, in total, 400 IU/ml of insulin with a combination of prandial insulin and basal insulin whose isoelectric point is between 5.8 and 8.5.

In one embodiment, the compositions according to the invention comprise, in total, 500 IU/ml of insulin with a combination of prandial insulin and basal insulin whose isoelectric point is between 5.8 and 8.5.

In one embodiment, the compositions according to the invention comprise, in total, 600 IU/ml of insulin with a combination of prandial insulin and basal insulin whose isoelectric point is between 5.8 and 8.5.

In one embodiment, the compositions according to the invention comprise, in total, 700 IU/ml of insulin with a combination of prandial insulin and basal insulin whose isoelectric point is between 5.8 and 8.5.

In one embodiment, the compositions according to the invention comprise, in total, 800 IU/ml of insulin with a combination of prandial insulin and basal insulin whose isoelectric point is between 5.8 and 8.5.

The proportions between the basal insulin whose isoelectric point is between 5.8 and 8.5 and the prandial insulin, expressed as percentage with respect to the total amount of insulin, are, for example, 25/75, 30/70, 40/60, 50/50, 60/40, 70/30, 80/20 and 90/10 for the formulations as described above from 40 to 800 IU/ml. However, any other proportion can be produced.

For a formulation comprising 100 IU/ml as total insulin, the proportions between the basal insulin whose isoelectric point is between 5.8 and 8.5 and the prandial insulin are, for example, in IU/ml, 25/75, 30/70, 40/60, 50/50, 60/40, 70/30, 80/20 or 90/10. However, any other proportion can be produced.

In one embodiment, the composition according to the invention additionally comprises a GLP-1, a GLP-1 analogue or a GLP-1 derivative.

In one embodiment, the GLP-1 analogues or derivatives are chosen from the group consisting of exenatide or Byetta®, developed by Eli Lilly & Co and Amylin Pharmaceuticals, liraglutide or Victoza® developed by Novo Nordisk, or lixisenatide or Lyxumia® developed by Sanofi, their analogues or derivatives and their pharmaceutically acceptable salts.

In one embodiment, the GLP-1 analogue or derivative is exenatide or Byetta®, its analogues or derivatives and their pharmaceutically acceptable salts.

In one embodiment, the GLP-1 analogue or derivative is liraglutide or Victoza®, its analogues or derivatives and their pharmaceutically acceptable salts.

In one embodiment, the GLP-1 analogue or derivative is lixisenatide or Lyxumia®, its analogues or derivatives and their pharmaceutically acceptable salts.

The term "analogue" is understood to mean, when it is used with reference to a peptide or a protein, a peptide or a protein in which one or more constituent amino acid residues have been replaced by other amino acid residues and/or from which one or more constituent amino acid residues have been deleted and/or to which one or more constituent amino acid residues have been added. The percentage of homology accepted for the present definition of an analogue is 50%.

The term "derivative" is understood to mean, when it is used with reference to a peptide or protein, a peptide or a protein or an analogue chemically modified by a substituent which is not present in the reference peptide or protein or analogue, that is to stay a peptide or a protein which has been modified by creation of covalent bonds, in order to introduce substituents.

In one embodiment, the concentration of GLP-1, of GLP-1 analogue or of GLP-1 derivative is within a range from 0.01 to 10 mg/ml.

In one embodiment, the concentration of exenatide, its analogues or derivatives and their pharmaceutically acceptable salts is within a range from 0.05 to 0.5 mg/ml.

In one embodiment, the concentration of liraglutide, its analogues or derivatives and their pharmaceutically acceptable salts is within a range from 1 to 10 mg/ml.

In one embodiment, the concentration of lixisenatide, its analogues or derivatives and their pharmaceutically acceptable salts is within a range from 0.01 to 1 mg/ml.

In one embodiment, the compositions according to the invention are produced by mixing commercial solutions of basal insulin whose isoelectric point is between 5.8 and 8.5 and commercial solutions of GLP-1, of GLP-1 analogue or of GLP-1 derivative in ratios by volume within a range from 10/90 to 90/10.

In one embodiment, the composition according to the invention comprises a daily dose of basal insulin and a daily dose of GLP-1, GLP-1 analogue or GLP-1 derivative.

In one embodiment, the compositions according to the invention comprise 500 IU/ml of basal insulin whose isoelectric point is between 5.8 and 8.5 and from 0.05 to 0.5 mg/ml of exenatide.

In one embodiment, the compositions according to the invention comprise 500 IU/ml of basal insulin whose isoelectric point is between 5.8 and 8.5 and from 1 to 10 mg/ml of liraglutide.

In one embodiment, the compositions according to the invention comprise 500 IU/ml of basal insulin whose isoelectric point is between 5.8 and 8.5 and from 0.05 to 0.5 mg/ml of lixisenatide.

In one embodiment, the compositions according to the invention comprise 100 IU/ml of basal insulin whose isoelectric point is between 5.8 and 8.5 and from 0.05 to 0.5 mg/ml of exenatide.

In one embodiment, the compositions according to the invention comprise 100 IU/ml of basal insulin whose isoelectric point is between 5.8 and 8.5 and from 1 to 10 mg/ml of liraglutide.

In one embodiment, the compositions according to the invention comprise 100 IU/ml of basal insulin whose isoelectric point is between 5.8 and 8.5 and from 0.05 to 0.5 mg/ml of lixisenatide.

In one embodiment, the compositions according to the invention comprise 40 IU/ml of basal insulin whose isoelectric point is between 5.8 and 8.5 and from 0.05 à 0.5 mg/ml of exenatide.

In one embodiment, the compositions according to the invention comprise 40 IU/ml of basal insulin whose isoelectric point is between 5.8 and 8.5 and from 1 to 10 mg/ml of liraglutide.

In one embodiment, the compositions according to the invention comprise 40 IU/ml of basal insulin whose isoelectric point is between 5.8 and 8.5 and from 0.05 à 0.5 mg/ml of lixisenatide.

In one embodiment, the compositions according to the invention comprise 200 IU/ml of basal insulin whose isoelectric point is between 5.8 and 8.5 and from 0.05 to 0.5 mg/ml of exenatide.

In one embodiment, the compositions according to the invention comprise 200 IU/ml of basal insulin whose isoelectric point is between 5.8 and 8.5 and from 1 to 10 mg/ml of liraglutide.

In one embodiment, the compositions according to the invention comprise 200 IU/ml of basal insulin whose isoelectric point is between 5.8 and 8.5 and from 0.05 to 0.5 mg/ml of lixisenatide.

In one embodiment, the compositions according to the invention additionally comprise zinc salts at a concentration of between 0 and 5000 µM.

In one embodiment, the compositions according to the invention additionally comprise zinc salts at a concentration of between 50 and 4000 µM.

In one embodiment, the compositions according to the invention additionally comprise zinc salts at a concentration of between 200 and 3000 µM.

In one embodiment, the compositions according to the invention additionally comprise zinc salts at a concentration of between 0 and 1000 µM.

In one embodiment, the compositions according to the invention additionally comprise zinc salts at a concentration of between 20 and 600 µM.

In one embodiment, the compositions according to the invention additionally comprise zinc salts at a concentration of between 50 and 500 µM.

In one embodiment, the compositions according to the invention comprise buffers chosen from the group consisting of Tris, citrates and phosphates at concentrations of between 0 and 100 mM, preferably between 0 and 50 mM or between 15 and 50 mM.

In one embodiment, the compositions according to the invention additionally comprise preservatives.

In one embodiment, the preservatives are chosen from the group consisting of m-cresol and phenol, alone or as a mixture.

In one embodiment, the concentration of the preservatives is between 10 and 50 mM.

In one embodiment, the concentration of the preservatives is between 10 and 40 mM.

The compositions according to the invention can additionally comprise additives, such as tonicity agents, such as glycerol, NaCl, mannitol and glycine.

The compositions according to the invention can additionally comprise additives in accordance with the pharmacopoeias, such as surfactants, for example polysorbate.

The compositions according to the invention can additionally comprise all the excipients in accordance with the pharmacopoeias which are compatible with the insulins used at the concentrations of use.

In one embodiment, $0.3 \leq n \leq 1.7$.
In one embodiment, $0.7 \leq n \leq 1.5$.
In one embodiment, $0.9 \leq n \leq 1.2$.
In one embodiment, $0.01 \leq m \leq 0.5$.
In one embodiment, $0.02 \leq m \leq 0.4$.
In one embodiment, $0.03 \leq m \leq 0.3$.
In one embodiment, $0.05 \leq m \leq 0.2$.
In one embodiment, $3 \leq q \leq 50$.
In one embodiment, $3 \leq q \leq 40$.
In one embodiment, $3 \leq q \leq 30$.
In one embodiment, $3 \leq q \leq 20$.
In one embodiment, $3 \leq q \leq 10$.

In one embodiment, the -(f-[A]-COOH)$_n$ radical is chosen from the group consisting of the following sequences, f having the meaning given above:

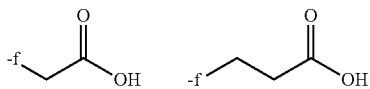

In one embodiment, the -(g-[B]-k-[D])$_m$ radical is chosen from the group consisting of the following sequences, g, k and D having the meanings given above:

In one embodiment, D is such that the X radical is an at least divalent radical resulting from an amino acid.

In one embodiment, D is such that the X radical is an at least divalent radical resulting from an amino acid chosen from the group consisting of glycine, leucine, phenylalanine, lysine, isoleucine, alanine, valine, aspartic acid and glutamic acid.

The radicals resulting from amino acids can be either laevorotatory or dextrorotatory.

In one embodiment, D is such that the X radical is an at least divalent radical resulting from a mono- or polyethylene glycol.

In one embodiment, D is such that the X radical is an at least divalent radical resulting from ethylene glycol.

In one embodiment, D is such that the X radical is an at least divalent radical resulting from a polyethylene glycol chosen from the group consisting of diethylene glycol and triethylene glycol.

In one embodiment, D is such that the X radical is an at least divalent radical resulting from a mono- or polyethylene glycol amine.

In one embodiment, D is such that the X radical is an at least divalent radical resulting from a mono- or polyethylene glycol amine chosen from the group consisting of ethanolamine, diethylene glycol amine and triethylene glycol amine.

In one embodiment, D is such that the X radical is an at least divalent radical resulting from a mono- or polyethylene glycol diamine.

In one embodiment, D is such that the X radical is an at least divalent radical resulting from ethylenediamine.

In one embodiment, D is such that the X radical is an at least divalent radical resulting from a mono- or polyethylene glycol diamine chosen from the group consisting of diethylene glycol diamine and triethylene glycol diamine.

In one embodiment, D is such that the Y group is an alkyl group resulting from a hydrophobic alcohol.

In one embodiment, D is such that the Y group is an alkyl group resulting from a hydrophobic alcohol chosen from the group consisting of octanol (capryl alcohol), 3,7-dimethyloctan-1-ol, decanol (decyl alcohol), dodecanol (lauryl alcohol), tetradecanol (myristyl alcohol) and hexadecanol (cetyl alcohol).

In one embodiment, D is such that the Y group is an alkyl group resulting from a hydrophobic acid.

In one embodiment, D is such that the Y group is an alkyl group resulting from a hydrophobic acid chosen from the group consisting of decanoic acid, dodecanoic acid, tetradecanoic acid and hexadecanoic acid.

In one embodiment, D is such that the Y group is a group resulting from a sterol.

In one embodiment, D is such that the Y group is a group resulting from a sterol chosen from the group consisting of cholesterol and its derivatives.

In one embodiment, D is such that the Y group is a group resulting from a tocopherol.

In one embodiment, D is such that the Y group is a group resulting from a tocopherol derivative chosen from the racemate, the L isomer or the D isomer of α-tocopherol.

In one embodiment, D is such that the X radical results from glycine, p=1, the Y group results from octanol and the functional group I is an ester functional group.

In one embodiment, D is such that the X radical results from glycine, p=1, the Y group results from dodecanol and the functional group I is an ester functional group.

In one embodiment, D is such that the X radical results from glycine, p=1, the Y group results from hexadecanol and the functional group I is an ester functional group.

In one embodiment, D is such that the X radical results from phenylalanine, p=1, the Y group results from octanol and the functional group I is an ester functional group.

In one embodiment, D is such that the X radical results from phenylalanine, p=1, the Y group results from 3,7-dimethyloctan-1-ol and the functional group I is an ester functional group.

In one embodiment, D is such that the X radical results from aspartic acid, p=2, the Y groups result from octanol and the functional groups I are ester functional groups.

In one embodiment, D is such that the X radical results from aspartic acid, p=2, the Y groups result from decanol and the functional groups I are ester functional groups.

In one embodiment, D is such that the X radical results from aspartic acid, p=2, the Y groups result from dodecanol and the functional groups I are ester functional groups.

In one embodiment, D is such that the X radical results from ethylenediamine, the Y group results from dodecanoic acid and the functional group I is an amide functional group.

In one embodiment, D is such that the X radical results from diethylene glycol amine, p=1, the Y group results from dodecanoic acid and the functional group I is an ester functional group.

In one embodiment, D is such that the X radical results from triethylene glycol diamine, p=1, the Y group results from dodecanoic acid and the functional group I is an amide functional group.

In one embodiment, D is such that the X radical results from triethylene glycol diamine, p=1, the Y group results from hexadecanoic acid and the functional group I is an amide functional group.

In one embodiment, D is such that the X radical results from leucine, p=1, the Y group results from cholesterol and the functional group I is an ester functional group.

In one embodiment, D is such that X results from ethylenediamine, p=1, the Y groups results from cholesterol and the functional group I is a carbamate functional group.

In one embodiment, the E radical is an at least divalent radical resulting from an amino acid chosen from the group consisting of glycine, leucine, phenylalanine, lysine, isoleucine, alanine, valine, serine, threonine, aspartic acid and glutamic acid.

The radicals resulting from amino acids can be either laevorotatory or dextrorotatory.

In one embodiment, the E radical is an at least divalent radical resulting from a mono- or polyethylene glycol amine.

In one embodiment, the E radical is an at least divalent radical resulting from a mono- or polyethylene glycol amine chosen from the group consisting of ethanolamine, diethylene glycol amine and triethylene glycol amine.

In one embodiment, the E radical is an at least divalent radical resulting from a mono- or polyethylene glycol diamine.

In one embodiment, the E radical is an at least divalent radical resulting from ethylenediamine.

In one embodiment, the E radical is an at least divalent radical resulting from a mono- or polyethylene glycol diamine chosen from the group consisting of diethylene glycol diamine and triethylene glycol diamine.

In one embodiment, the F group is an alkyl group resulting from a hydrophobic alcohol.

In one embodiment, the F group is a group resulting from a hydrophobic alcohol chosen from the group consisting of dodecanol (lauryl alcohol), tetradecanol (myristyl alcohol) and hexadecanol (cetyl alcohol).

In one embodiment, the F group is a group resulting from a hydrophobic acid.

In one embodiment, the F group is a group resulting from a hydrophobic acid chosen from the group consisting of dodecanoic acid, tetradecanoic acid and hexadecanoic acid.

In one embodiment, the F group is a group resulting from a sterol.

In one embodiment, the F group is a group resulting from a sterol chosen from the group consisting of cholesterol and its derivatives.

In one embodiment, the F group is a group resulting from a tocopherol.

In one embodiment, the F group is a group resulting from a tocopherol derivative chosen from the racemate, the L isomer or the D isomer of α-tocopherol.

In one embodiment, the E radical results from ethylenediamine, t=1, o is a carbamate functional group and the F group results from cholesterol.

In one embodiment:
- -(f-[A]-COOH)$_n$ is such that A is the —CH$_2$— radical and f is an ether functional group;
- -(g-[B]-k-[D])$_m$ is such that g is an ether functional group, B is the —CH$_2$— radical, k is an amide functional group and D is such that X results from glycine, l is an ester functional group and Y results from octanol;
- q=38, n=0.9 and m=0.2.

In one embodiment:
- -(f-[A]-COOH)$_n$ is such that A is the —CH$_2$— radical and f is an ether functional group;
- -(g-[B]-k-[D])$_m$ is such that g is an ether functional group, B is the —CH$_2$— radical, k is an amide functional group and D is such that X results from glycine, p=1, l is an ester functional group and Y results from hexadecanol;
- q=19, n=1.0 and m=0.1.

In one embodiment:
- -(f-[A]-COOH)$_n$ is such that A is the —CH$_2$— radical and f is an ether functional group;
- -(g-[B]-k-[D])$_m$ is such that g is an ether functional group, B is the —CH$_2$— radical, k is an amide functional group and D is such that X results from phenylalanine, p=1, l is an ester functional group and Y results from octanol;
- q=38, n=1.0 and m=0.1.

In one embodiment:
- -(f-[A]-COOH)$_n$ is such that A is the —CH$_2$— radical and f is an ether functional group;
- -(g-[B]-k-[D])$_m$ is such that g is an ether functional group, B is the —CH$_2$— radical, k is an amide functional group and D is such that X results from phenylalanine, p=1, l is an ester functional group and Y results from octanol;
- q=19, n=1.0 and m=0.2.

In one embodiment:
- -(f-[A]-COOH)$_n$ is such that A is the —CH$_2$— radical and f is an ether functional group;
- -(g-[B]-k-[D])$_m$ is such that g is an ether functional group, B is the —CH$_2$— radical, k is an amide functional group and D is such that X results from phenylalanine, p=1, l is an ester functional group and Y results from 3,7-dimethyloctan-1-ol;
- q=38, n=1.0 and m=0.1.

In one embodiment:
- -(f-[A]-COOH)$_n$ is such that A is the —CH$_2$— radical and f is an ether functional group;
- -(g-[B]-k-[D])$_m$ is such that g is an ether functional group, B is the —CH$_2$— radical, k is an amide functional group and D is such that X results from aspartic acid, p=2, l are ester functional groups and Y result from octanol;
- q=38, n=1.05 and m=0.05.

In one embodiment:
- -(f-[A]-COOH)$_n$ is such that A is the —CH$_2$— radical and f is an ether functional group;
- -(g-[B]-k-[D])$_m$ is such that g is an ether functional group, B is the —CH$_2$— radical, k is an amide functional group and D is such that X results from aspartic acid, p=2, l are ester functional groups and Y result from decanol;
- q=38, n=1.05 and m=0.05.

In one embodiment:
- -(f-[A]-COOH)$_n$ is such that A is the —CH$_2$— radical and f is an ether functional group;
- -(g-[B]-k-[D])$_m$ is such that g is an ether functional group, B is the —CH$_2$— radical, k is an amide functional group and D is such that X results from aspartic acid, p=2, l are ester functional groups and Y result from dodecanol;
- q=19, n=1.05 and m=0.05.

In one embodiment:
- -(f-[A]-COOH)$_n$ is such that A is the —CH$_2$— radical and f is an ether functional group;
- -(g-[B]-k-[D])$_m$ is such that g is an ether functional group, B is the —CH$_2$— radical, k is an amide functional group and D is such that X results from ethylenediamine, p=1, l is an amide functional group and Y results from dodecanoic acid;
- q=38, n=1.0 and m=0.1.

In one embodiment:
- -(f-[A]-COOH)$_n$ is such that A is the —CH$_2$—CH$_2$— radical and f is an ester functional group;
- -(g-[B]-k-[D])$_m$ is such that g is an ester functional group, B is the —CH$_2$—CH$_2$— radical, k is an amide functional group and D is such that X results from glycine, p=1, l is an ester functional group and Y results from dodecanol;
- q=38, n=1.3 and m=0.1.

In one embodiment:
- -(f-[A]-COOH)$_n$ is such that A is the —CH$_2$— radical and f is a carbamate functional group;
- -(g-[B]-k-[D])$_m$ is such that g is a carbamate functional group, B is the —CH$_2$— radical, k is an amide functional group and D is such that X results from aspartic acid, p=2, l are ester functional groups and Y result from octanol;
- q=38, n=1.3 and m=0.1.

In one embodiment:
- -(f-[A]-COOH)$_n$ is such that A is the —CH$_2$— radical and f is an ether functional group;
- -(g-[B]-k-[D])$_m$ is such that g is an ether functional group, B is the —CH$_2$— radical, k is an amide functional group and D is such that X results from aspartic acid, p=2, l are ester functional groups and Y result from dodecanol;
- q=4, n=0.96 and m=0.07.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from diethylene glycol amine, p=1, l is an ester functional group and Y results from dodecanoic acid;
q=38, n=1.0 and m=0.1.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from triethylene glycol diamine, p=1, l is an amide functional group and Y results from dodecanoic acid;
q=38, n=1.0 and m=0.1.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from triethylene glycol diamine, p=1, l is an amide functional group and Y results from hexadecanoic acid;
q=38, n=1.05 and m=0.05.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from glycine, p=1, l is an ester functional group and Y results from hexadecanol;
q=19, n=1.05 and m=0.05.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from glycine, p=1, l is an ester functional group and Y results from hexadecanol;
q=38, n=0.37 and m=0.05.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from leucine, p=1, l is an ester functional group and Y results from cholesterol;
q=19, n=1.61 and m=0.04.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from leucine, p=1, l is an ester functional group and Y results from cholesterol;
q=19, n=1.06 and m=0.04.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from leucine, p=1, l is an ester functional group and Y results from cholesterol;
q=19, n=0.66 and m=0.04.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from leucine, p=1, l is an ester functional group and Y results from cholesterol;
q=19, n=0.46 and m=0.04.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from leucine, p=1, l is an ester functional group and Y results from cholesterol;
q=4, n=1.61 and m=0.05.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from ethylenediamine, p=1, l is a carbamate functional group and Y results from cholesterol;
q=19, n=1.61 and m=0.04.

In one embodiment:
-(f-[A]-COOH)$_n$ is such that A is the —CH$_2$— radical and f is a carbamate functional group;
-(g-[B]-k-[D])$_m$ is such that g is a carbamate functional group, B is the —CH$_2$— radical, k is an amide functional group and D is such that X results from leucine, p=1, l is an ester functional group and Y results from cholesterol;
q=19, n=1.96 and m=0.04.

In one embodiment:
-(f-[A]-COOH)$_n$ is such that A is the —CH$_2$— radical and f is an ether functional group;
-[E]-(o-[F])$_t$ is such that E results from ethylenediamine, o is a carbamate functional group and F results from cholesterol;
q=19 and n=1.65.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from leucine, p=1, l is an ester functional group and Y results from cholesterol;
q=38, n=0.99 and m=0.05.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from aspartic acid, p=2, l are ester functional groups and Y result from dodecanol;
q=4, n=1.41 and m=0.16.

In one embodiment:
-(f-[A]-COOH)$_n$ is such that A is the —CH$_2$— radical and f is an ether functional group;
-(g-[B]-k-[D])$_m$ is such that g is an ether functional group, B is the —CH$_2$— radical, k is an amide functional group and D is such that X results from aspartic acid, p=2, l are ester functional groups and Y result from dodecanol;
q=4, n=1.50 and m=0.07.

In one embodiment:
-(f-[A]-COOH)$_n$ is such that A is the —CH$_2$— radical and f is an ether functional group;

-(g-[B]-k-[D])$_m$ is such that g is an ether functional group, B is the —CH$_2$— radical, k is an amide functional group and D is such that X results from aspartic acid, p=2, l are ester functional groups and Y result from decanol;

q=4, n=1.05 and m=0.05.

In one embodiment, the compositions according to the invention comprise a dextran chosen from the group consisting of the following dextrans of formula I, III or IV:

Sodium dextranmethylcarboxylate modified by octyl glycinate,

Sodium dextranmethylcarboxylate modified by cetyl glycinate,

Sodium dextranmethylcarboxylate modified by octyl phenylalaninate,

Sodium dextranmethylcarboxylate modified by 3,7-dimethyl-1-octyl phenylalaninate, Sodium dextranmethylcarboxylate modified by dioctyl aspartate, Sodium dextranmethylcarboxylate modified by didecyl aspartate, Sodium dextranmethylcarboxylate modified by dilauryl aspartate, Sodium dextranmethylcarboxylate modified by N-(2-aminoethyl)dodecanamide, Sodium dextransuccinate modified by lauryl glycinate, N-(sodium methylcarboxylate) dextran carbamate modified by dioctyl aspartate, Sodium dextranmethylcarboxylate modified by 2-(2-aminoethoxy)ethyl dodecanoate, Sodium dextranmethylcarboxylate modified by 2-(2-{2-[dodecanoylamino]ethoxy}ethoxy)ethylamine, Sodium dextranmethylcarboxylate modified by 2-(2-{2-[hexadecanoylamino]ethoxy}ethoxy)ethylamine, Sodium dextranmethylcarboxylate modified by cholesteryl leucinate, Sodium dextranmethylcarboxylate modified by cholesteryl 1-ethylenediaminecarboxylate, N-(sodium methylcarboxylate) dextran carbamate modified by cholesteryl leucinate.

In one embodiment, the compositions according to the invention comprise a dextran chosen from the group consisting of the dextran of the following formula II:

Sodium dextranmethylcarboxylate modified by cholesteryl 1-ethylenediaminecarboxylate grafted by reductive amination to the reducing chain end.

The invention also relates to single-dose formulations at a pH of between 6.6 and 7.8 comprising a basal insulin whose isoelectric point is between 5.8 and 8.5 and a prandial insulin.

The invention also relates to single-dose formulations at a pH of between 7 and 7.8 comprising a basal insulin whose isoelectric point is between 5.8 and 8.5 and a prandial insulin.

In one embodiment, the basal insulin whose isoelectric point is between 5.8 and 8.5 is insulin glargine.

In one embodiment, the prandial insulin is chosen from the group consisting of Humulin® (human insulin) and Novolin® (human insulin).

In one embodiment, the prandial insulin is chosen from the group consisting of insulin lispro (Humalog®), insulin glulisine (Apidra®) and insulin aspart (NovoLog®).

The dissolution at a pH of between 6.6 and 7.8 of the basal insulins whose isoelectric point is between 5.8 and 8.5 by the polysaccharides of formula I, II, III or IV can be observed and controlled in a simple way, with the naked eye, by virtue of a change in appearance of the solution The dissolution at a pH of between 7 and 7.8 of the basal insulins whose isoelectric point is between 5.8 and 8.5 by the polysaccharides of formula I, II, III or IV can be observed and controlled in a simple way, with the naked eye, by virtue of a change in appearance of the solution.

Furthermore and just as importantly, the Applicant Company has been able to confirm that a basal insulin whose isoelectric point is between 5.8 and 8.5, dissolved in the presence of a polysaccharide of formula I, II, III or IV, had lost none of its slow insulin action.

The preparation of a composition according to the invention exhibits the advantage of being able to be carried out by simple mixing of an aqueous solution of basal insulin whose isoelectric point is between 5.8 and 8.5, of a solution of prandial insulin and of a polysaccharide of formula I, II, III or IV in aqueous solution or in the lyophilized form. If necessary, the pH of the preparation is adjusted to pH 7.

The preparation of a composition according to the invention exhibits the advantage of being able to be carried out by simple mixing of an aqueous solution of basal insulin whose isoelectric point is between 5.8 and 8.5, of a polysaccharide of formula I, II, III or IV in aqueous solution or in the lyophilized form, and of a prandial insulin in aqueous solution or in the lyophilized form.

In one embodiment, the mixture of basal insulin and polysaccharide is concentrated by ultrafiltration before mixing with the prandial insulin in aqueous solution or in the lyophilized form.

If necessary, the composition of the mixture is adjusted in excipients, such as glycerol, m-cresol, zinc chloride and tween, by addition of concentrated solutions of these excipients to the mixture. If necessary, the pH of the preparation is adjusted to 7.

DESCRIPTION OF THE FIGURES

FIG. 1: Mean+standard deviation of the mean curves for the sequential administrations of Apidra® and Lantus® (□) in comparison with a composition according to the invention Polysaccharide 4/Lantus®/Apidra® (75/25) (■).

FIG. 2: Apidra® Lantus® individual curves (tested on six pigs).

FIG. 3: Polysaccharide 4/Apidra®/Lantus® individual curves (tested on six pigs).

FIG. 4: Mean+standard deviation of the mean curves for the sequential administration of Humalog® and Lantus® (□) in comparison with the administration of a composition according to the invention Polysaccharide 4/Humalog®/Lantus® (■).

FIG. 5: Humalog® Lantus® individual curves (tested on six pigs).

FIG. 6: Polysaccharide 4/Humalog®/Lantus® individual curves (tested on five pigs).

FIG. 7: Mean+standard deviation of the mean curves for the sequential administrations of Humalog® (100 IU/ml, 0.13 IU/kg) and Lantus® (100 IU/ml, 0.4 IU/kg) (...■..), in comparison with a composition according to the invention described in Example B28 (0.53 IU/kg) (—■—).

FIG. 8: Mean+standard deviation of the mean curves for the sequential administrations of Humalog® (100 IU/ml, 0.13 IU/kg) and Lantus® (100 IU/ml, 0.4 IU/kg) (...■..), in comparison with a composition according to the invention described in Example B27 (0.47 IU/kg) (—■—).

FIG. 9: Mean+standard deviation of the mean curves for the sequential administrations of Humalog® (100 IU/ml, 0.13 IU/kg) and Lantus® (100 IU/ml, 0.4 IU/kg) (...■..), in comparison with a composition according to the invention described in Example B29 (0.53 IU/kg) ( —■— ).

FIG. 10: Mean+standard deviation of the mean curves for the sequential administrations of Humalog® (100 IU/ml, 0.13 IU/kg) and Lantus® (100 IU/ml, 0.4 IU/kg) (...■..), in comparison with a composition according to the invention described in Example B31 (0.48 IU/kg) ( —■— ).

FIG. 11: Mean+standard deviation of the mean curves for the sequential administrations of Humalog® (100 IU/ml, 0.24 IU/kg) and Lantus® (100 IU/ml, 0.4 IU/kg) (...■..), in comparison with a composition according to the invention described in Example B30 (0.64 IU/kg) ( —■— ).

FIG. 12: Mean+standard deviation of the mean curves for the sequential administrations of Humalog® (100 IU/ml, 0.13 IU/kg) and Lantus® (100 IU/ml, 0.4 IU/kg) (...■..), in comparison with a composition according to the invention described in Example B32 (0.53 IU/kg) ( —■— ).

EXAMPLES

Part A

Polysaccharides

Figure 1:
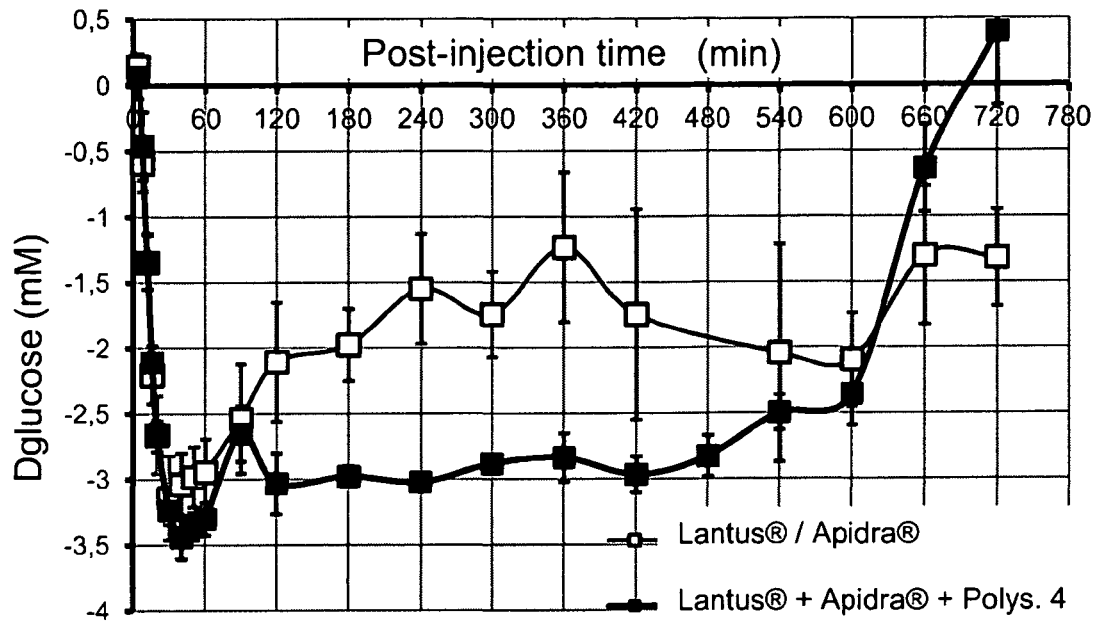
FIGS. 1 to 6 present the results obtained in the form of pharmacodynamic curves for glucose. The axis of the ordinates represents the Dglucose (expressed in mM) as a function of the post-injection time (expressed in minutes).

Table 1 below presents, in a nonlimiting way, examples of polysaccharides which can be used in the compositions according to the invention.

TABLE 1

| POLY-SACCHARIDES | SUBSTITUENTS -f-A-COONa -g-B-k-D | COMMON NAME |
|---|---|---|
| Polysaccharide 1<br>q: 38<br>n: 0.9<br>m: 0.2 | | Sodium dextranmethylcarboxylate modified by octyl glycinate |
| Polysaccharide 2<br>q: 19<br>n: 1.0<br>m: 0.1<br>Polysaccharide 16<br>q: 19<br>n: 1.05<br>m: 0.05<br>Polysaccharide 17<br>q: 38<br>n: 0.37<br>m: 0.05 | | Sodium dextranmethylcarboxylate modified by cetyl glycinate |
| Polysaccharide 3<br>q: 38<br>n: 1.0<br>m: 0.1<br>Polysaccharide 4<br>q: 19<br>n: 1.0<br>m: 0.2 | | Sodium dextranmethylcarboxylate modified by octyl phenylalaninate |
| Polysaccharide 5<br>q: 38<br>n: 1.0<br>m: 0.1 | | Sodium dextranmethylcarboxylate modified by 3,7-dimethyl-1-octyl phenylalaninate |

TABLE 1-continued

| | | |
|---|---|---|
| Polysaccharide 6<br>q: 38<br>n: 1.05<br>m: 0.05 | 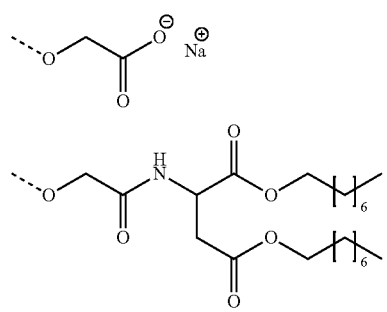 | Sodium dextranmethylcarboxylate modified by dioctyl aspartate |
| Polysaccharide 7<br>q: 38<br>n: 1.05<br>m: 0.05<br>Polysaccharide 29<br>q: 4<br>n: 1.05<br>m: 0.05 | 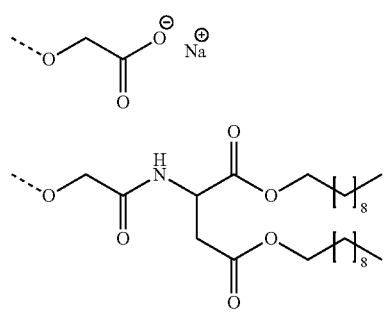 | Sodium dextranmethylcarboxylate modified by didecyl aspartate |
| Polysaccharide 8<br>q: 19<br>n: 1.05<br>m: 0.05<br>Polysaccharide 27<br>q: 4<br>n: 1.41<br>m: 0.16<br>Polysaccharide 28<br>q: 4<br>n: 1.50<br>m: 0.07 | 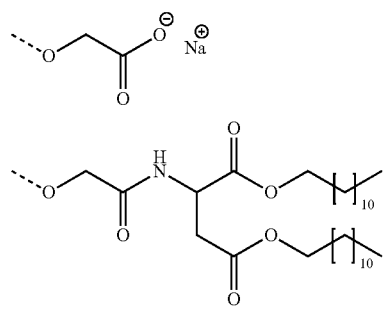 | Sodium dextranmethylcarboxylate modified by dilauryl aspartate |
| Polysaccharide 9<br>q: 38<br>n: 1.0<br>m: 0.1 | 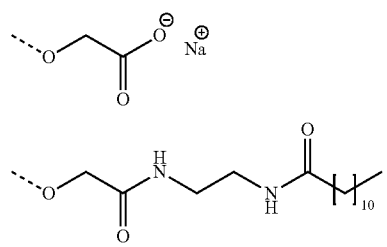 | Sodium dextranmethylcarboxylate modified by N-(2-aminoethyl)dodecanamide |
| Polysaccharide 10<br>q: 38<br>n: 1.3<br>m: 0.1 | 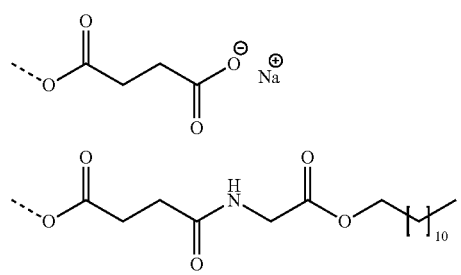 | Sodium dextransuccinate modified by lauryl glycinate |

TABLE 1-continued

| | | |
|---|---|---|
| Polysaccharide 11<br>q: 38<br>n: 1.3<br>m: 0.1 | 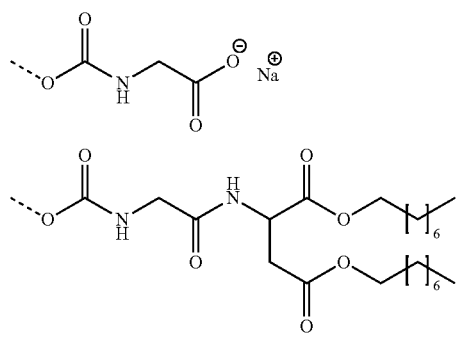 | N-(sodium methylcarboxylate) dextran carbamate modified by dioctyl aspartate |
| Polysaccharide 12<br>q: 4<br>n: 0.96<br>m: 0.07 | 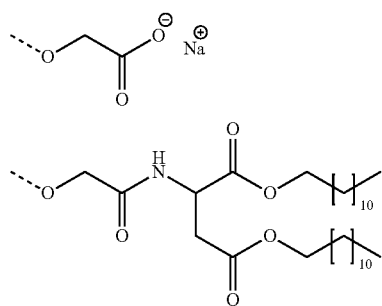 | Sodium dextranmethylcarboxylate modified by dilauryl aspartate |
| Polysaccharide 13<br>q: 38<br>n: 1.0<br>m: 0.1 | 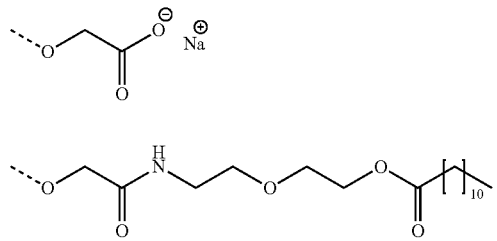 | Sodium dextranmethylcarboxylate modified by 2-(2-aminoethoxy)ethyl dodecanoate |
| Polysaccharide 14<br>q: 38<br>n: 1.0<br>m: 0.1 | 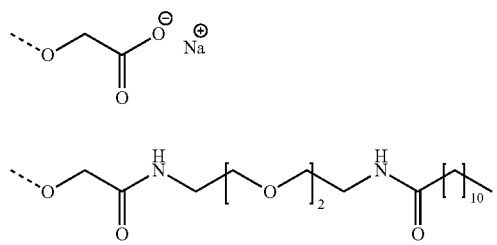 | Sodium dextranmethylcarboxylate modified by 2-(2-{2-[dodecanoylamino]ethoxy}ethoxy)ethylamine |
| Polysaccharide 15<br>q: 38<br>n: 1.05<br>m: 0.05 | 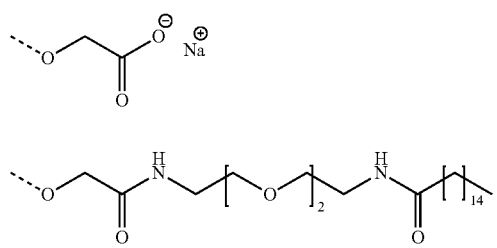 | Sodium dextranmethylcarboxylate modified by 2-(2-{2-[hexadecanoylamino]ethoxy}ethoxy)ethylamine |

TABLE 1-continued

Polysaccharide 18
q: 19
n: 1.61
m: 0.04

Polysaccharide 19
q: 19
n: 1.06
m: 0.04

Polysaccharide 20
q: 19
n: 0.66
m: 0.04

Polysaccharide 21
q: 19
n: 0.46
m: 0.04

Polysaccharide 22
q: 4
n: 1.61
m: 0.04

Polysaccharide 26
q: 38
n: 0.99
m: 0.05

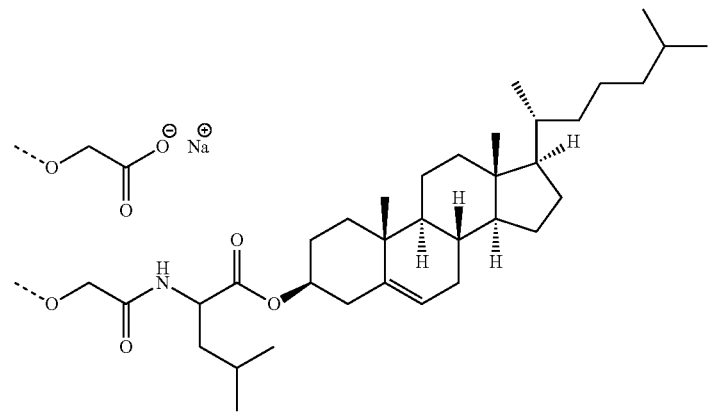

Sodium dextranmethylcarboxylate modified by cholesteryl leucinate

Polysaccharide 23
q: 19
n: 1.61
m: 0.04

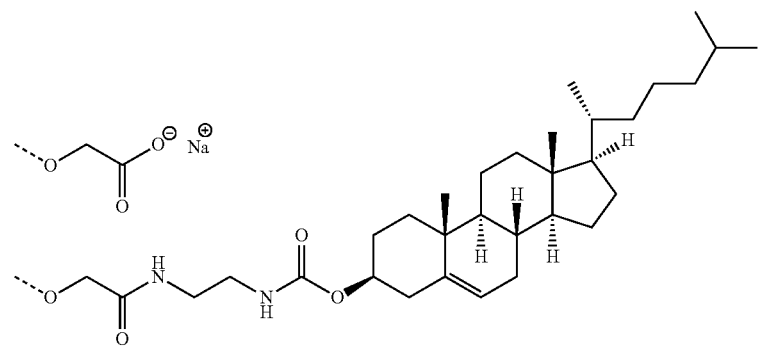

Sodium dextranmethylcarboxylate modified by cholesteryl 1-ethylenediaminecarboxylate Polysaccharide 24
q: 19
n: 1.96
m: 0.04

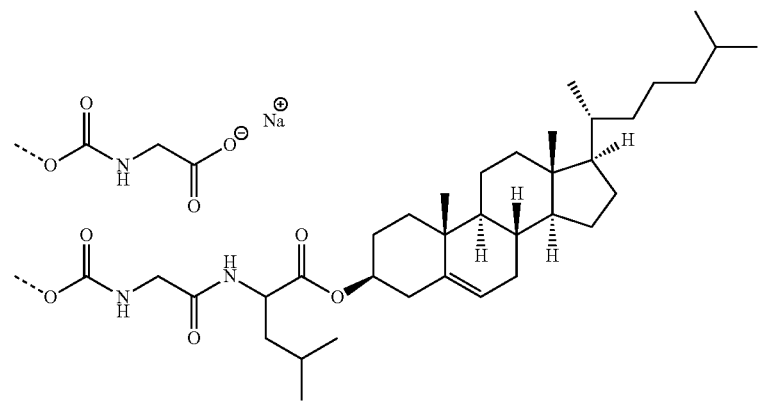

N-(sodium methylcarboxylate) dextran carbamate modified by cholesteryl leucinate

| POLY-SACCHARIDES | SUBSTITUENTS -f-A-COONa -[E]-o-[F] | COMMON NAME |
|---|---|---|
| Polysaccharide 25 q: 19 n: 1.65 | | Sodium dextranmethylcarboxylate modified by cholesteryl 1-ethylenediaminecarboxylate grafted by reductive amination to the reducing chain end |

Example A1

Preparation of Polysaccharide 1

16 g (i.e., 296 mmol of hydroxyls) of dextran with a weight-average molar mass of approximately 10 kg/mol (q=38, Pharmacosmos) are dissolved in water at 420 g/l. 30 ml of 10N NaOH (296 mmol) are added to the solution. The mixture is brought to 35° C. and then 46 g (396 mmol) of sodium chloroacetate are added. The temperature of the reaction mixture is brought to 60° C. at 0.5° C./min and then maintained at 60° C. for 100 minutes. The reaction medium is diluted with 200 ml of water, neutralized with acetic acid and purified by ultrafiltration through a 5 kDa PES membrane against 6 volumes of water. The final solution is assayed by dry extract, to determine the concentration of polysaccharide, and then assayed by acid/base titration in 50/50 (V/V) water/acetone, to determine the mean number of methylcarboxylate units per glucoside unit.

According to the dry extract: [polysaccharide]=31.5 mg/g.

According to the acid/base titration: the mean number of methylcarboxylate units per glucoside unit is 1.1.

The sodium dextranmethylcarboxylate solution is passed through a Purolite resin (anionic) in order to obtain dextranmethylcarboxylic acid, which is subsequently lyophilized for 18 hours.

Octyl glycinate, para-toluenesulphonic acid salt, is obtained according to the process described in U.S. Pat. No. 4,826,818.

10 g of dextranmethylcarboxylic acid (44.86 mmol of methylcarboxylic acid) are dissolved in DMF at 60 g/l and then cooled to 0° C. 3.23 g of octyl glycinate, para-toluenesulphonic acid salt, (8.97 mmol) are suspended in DMF at 100 g/l. 0.91 g of triethylamine (8.97 mmol) is subsequently added to the suspension. Once the polysaccharide solution is at 0° C., a solution of NMM (5.24 g, 51.8 mmol) in DMF (530 g/l) and 5.62 g (51.8 mmol) of EtOCOCl are subsequently added. After reacting for 10 minutes, the octyl glycinate suspension is added. The medium is subsequently maintained at 10° C. for 45 minutes. The medium is subsequently heated to 30° C. A solution of imidazole (10.38 g in 17 ml of water) and 52 ml of water are added to the reaction medium. The polysaccharide solution is ultrafiltered through a 10 kDa PES membrane against 15 volumes of 0.9% NaCl solution and 5 volumes of water. The concentration of the polysaccharide solution is determined by dry extract. A fraction of solution is lyophilized and analyzed by $^1$H NMR in $D_2O$ in order to determine the degree of substitution of the methylcarboxylates to give octyl glycinate per glucoside unit.

According to the dry extract: [Polysaccharide 1]=36.4 mg/g

According to the acid/base titration: n=0.9

According to the $^1$H NMR: m=0.2.

Example A2

Preparation of Polysaccharide 2

Cetyl glycinate, para-toluenesulphonic acid salt, is obtained according to the process described in U.S. Pat. No. 4,826,818.

A sodium dextranmethylcarboxylate, synthesized according to the process described in Example A1 using a dextran with a weight-average molecular weight of approximately 5 kg/mol (q=19, Pharmacosmos), modified by cetyl glycinate, is obtained by a process similar to that described in Example A1.

According to the dry extract: [Polysaccharide 2]=15.1 mg/g

According to the acid/base titration: n=1.05

According to the $^1$H NMR: m=0.05.

Example A3

Preparation of Polysaccharide 3

Octyl phenylalaninate, para-toluenesulphonic acid salt, is obtained according to the process described in U.S. Pat. No. 4,826,818.

A sodium dextranmethylcarboxylate, synthesized according to the process described in Example A1 using a dextran with a weight-average molecular weight of approximately 10 kg/mol (q=38, Pharmacosmos), modified by octyl phenylalaninate, is obtained by a process similar to that described in Example A1.

According to the dry extract: [Polysaccharide 3]=27.4 mg/g

According to the acid/base titration: n=1.0

According to the $^1$H NMR: m=0.1.

Example A4

Preparation of Polysaccharide 4

A sodium dextranmethylcarboxylate, synthesized according to the process described in Example A1 using a dextran with a weight-average is molecular weight of approximately 5 kg/mol (q=19, Pharmacosmos), modified by octyl phenylalaninate, is obtained by a process similar to that described in Example A3.

According to the dry extract: [Polysaccharide 4]=21.8 mg/g
According to the acid/base titration: n=1.0
According to the $^1$H NMR: m=0.2.

Example A5

Preparation of Polysaccharide 5

3,7-dimethyl-1-octyl phenylalaninate, para-toluenesulphonic acid salt, is obtained according to the process described in U.S. Pat. No. 4,826,818.

A sodium dextranmethylcarboxylate, synthesized according to the process described in Example A1 using a dextran with a weight-average molecular weight of approximately 10 kg/mol (q=38, Pharmacosmos), modified by 3,7-dimethyl-1-octyl phenylalaninate, is obtained by a process similar to that described in Example A1.

According to the dry extract: [Polysaccharide 5]=24.3 mg/g
According to the acid/base titration: n=1.0
According to the $^1$H NMR: m=0.1.

Example A6

Preparation of Polysaccharide 6

Dioctyl aspartate, para-toluenesulphonic acid salt, is obtained according to the process described in U.S. Pat. No. 4,826,818.

A sodium dextranmethylcarboxylate, synthesized according to the process described in Example A1 using a dextran with a weight-average molecular weight of approximately 10 kg/mol (q=38, Pharmacosmos), modified by dioctyl aspartate, is obtained by a process similar to that described in Example A1.

According to the dry extract: [Polysaccharide 6]=22.2 mg/g
According to the acid/base titration: n=1.05
According to the $^1$H NMR: m=0.05.

Example A7

Preparation of Polysaccharide 7

Didecyl aspartate, para-toluenesulphonic acid salt, is obtained according to the process described in U.S. Pat. No. 4,826,818.

A sodium dextranmethylcarboxylate, synthesized according to the process described in Example A1 using a dextran with a weight-average molecular weight of approximately 10 kg/mol (q=38, Pharmacosmos), modified by didecyl aspartate, is obtained by a process similar to that described in Example A1.

According to the dry extract: [Polysaccharide 7]=19.8 mg/g
According to the acid/base titration: n=1.05
According to the $^1$H NMR: m=0.05.

Example A8

Preparation of Polysaccharide 8

Dilauryl aspartate, para-toluenesulphonic acid salt, is obtained according to the process described in U.S. Pat. No. 4,826,818.

A sodium dextranmethylcarboxylate, synthesized according to the process described in Example A1 using a dextran with a weight-average molecular weight of approximately 5 kg/mol (q=19, Pharmacosmos), modified by dilauryl aspartate is obtained by a process similar to that described in Example A1.

According to the dry extract: [Polysaccharide 8]=22.8 mg/g
According to the acid/base titration: n=1.05
According to the $^1$H NMR: m=0.05.

Example A9

Preparation of Polysaccharide 9

N-(2-aminoethyl)dodecanamide is obtained according to the process described in U.S. Pat. No. 2,387,201, from the methyl ester of dodecanoic acid (Sigma) and ethylenediamine (Roth).

A sodium dextranmethylcarboxylate, synthesized according to the process described in Example A1 using a dextran with a weight-average molecular weight of approximately 10 kg/mol (q=38, Pharmacosmos), modified by N-(2-aminoethyl)dodecanamide, is obtained by a process similar to that described in Example A1.

According to the dry extract: [Polysaccharide 9]=23.8 mg/g
According to the acid/base titration: n=1.0
According to the $^1$H NMR: m=0.1.

Example A10

Preparation of Polysaccharide 10

Sodium dextransuccinate is obtained from a dextran with a weight-average molar mass of approximately 10 kg/mol (q=38, Pharmacosmos) according to the method described in the paper by Sanchez-Chaves et al., 1998 (Manuel et al., Polymer, 1998, 39 (13), 2751-2757). According to the $^1$H NMR in $D_2O$/NaOD, the mean number of succinate groups per glucoside unit is 1.4.

Lauryl glycinate, para-toluenesulphonic acid salt, is obtained according to the process described in U.S. Pat. No. 4,826,818.

A sodium dextransuccinate modified by lauryl glycinate is obtained by a process similar to that described in Example A1.

According to the dry extract: [Polysaccharide 10]=16.1 mg/g
According to the acid/base titration: n=1.3
According to the $^1$H NMR: m=0.1.

Example A11

Preparation of Polysaccharide 11

Dioctyl aspartate, para-toluenesulphonic acid salt, is obtained according to the process described in U.S. Pat. No. 4,826,818.

12 g (i.e., 0.22 mol of hydroxyls) of dextran with a weight-average molar mass of approximately 10 kg/mol (q=38, Pharmacosmos) are dissolved in a DMF/DMSO mixture. The mixture is brought to 80° C. with stirring. 3.32 g (0.03 mol) of 1,4-diazabicyclo[2.2.2]octane and then 14.35 g (0.11 mol) of ethyl isocyanatoacetate are gradually introduced. After reacting for 5 h, the medium is diluted in water and purified by diafiltration through a 5 kDa PES membrane against 0.1N NaOH, 0.9% NaCl and water. The final solution is assayed by dry extract, to determine the concentration of polysaccharide; and then assayed by acid/base titration in 50/50 (V/V) water/acetone, to determine the mean number de N-methylcarboxylate carbamate units per glucoside unit.

According to the dry extract: [polysaccharide]=30.5 mg/g

According to the acid/base titration: the mean number of N-methylcarboxylate carbamate units per glucoside unit is 1.4.

An N-(sodium methylcarboxylate) dextran carbamate modified by dioctyl aspartate is obtained by a process similar to that described in Example A1.

According to the dry extract: [Polysaccharide 11]=17.8 mg/g
According to the acid/base titration: n=1.3
According to the $^1$H NMR: m=0.1.

Example A12

Preparation of Polysaccharide 12

Dilauryl aspartate, para-toluenesulphonic acid salt, is obtained according to the process described in U.S. Pat. No. 4,826,818.

A sodium dextranmethylcarboxylate, synthesized according to the process described in Example A1 using a dextran with a weight-average molecular weight of approximately 1 kg/mol (q=4, Pharmacosmos), modified by dilauryl aspartate, is obtained by a process similar to that described in Example A1.

According to the dry extract: [Polysaccharide 12]=12.3 mg/g
According to the acid/base titration: n=0.96
According to the $^1$H NMR: m=0.07.

Example A13

Preparation of Polysaccharide 13

2-(2-aminoethoxy)ethyl dodecanoate, para-toluenesulphonic acid salt, is obtained according to the process described in U.S. Pat. No. 4,826,818.

A sodium dextranmethylcarboxylate, synthesized according to the process described in Example A1 using a dextran with a weight-average molecular weight of approximately 10 kg/mol (q=38, Pharmacosmos), modified by 2-(2-aminoethoxy)ethyl dodecanoate is obtained, by a process similar to that described in Example A1.

According to the dry extract: [Polysaccharide 13]=25.6 mg/g
According to the acid/base titration: n=1.0
According to the $^1$H NMR: m=0.1.

Example A14

Preparation of Polysaccharide 14

2-(2-{2-[dodecanoylamino]ethoxy}ethoxy)ethylamine is obtained according to the process described in U.S. Pat. No. 2,387,201, from the methyl ester of dodecanoic acid (Sigma) and triethylene glycol diamine (Huntsman).

A sodium dextranmethylcarboxylate, synthesized according to the process described in Example A1 using a dextran with a weight-average molecular weight of approximately 10 kg/mol (q=38, Pharmacosmos), modified by 2-(2-{2-[dodecanoylamino]ethoxy}ethoxy)ethylamine, is obtained by a process similar to that described in Example A1.

According to the dry extract: [Polysaccharide 14]=24.9 mg/g
According to the acid/base titration: n=1.0
According to the $^1$H NMR: m=0.1.

Example A15

Preparation of Polysaccharide 15

2-(2-{2-[hexadecanoylamino]ethoxy}ethoxy)ethylamine is obtained, according to the process described in U.S. Pat. No. 2,387,201, from the methyl ester of palmitic acid (Sigma) and triethylene glycol diamine (Huntsman).

A sodium dextranmethylcarboxylate, synthesized according to the process described in Example A1 using a dextran with a weight-average molecular weight of approximately 10 kg/mol (q=38, Pharmacosmos), modified by 2-(2-{2-[hexadecanoylamino]ethoxy}ethoxy)ethylamine is obtained by a process similar to that described in Example A1.

According to the dry extract: [Polysaccharide 15]=22.2 mg/g
According to the acid/base titration: n=1.05
According to the $^1$H NMR: m=0.05.

Example A16

Preparation of Polysaccharide 16

Cetyl glycinate, para-toluenesulphonic acid salt, is obtained according to the process described in U.S. Pat. No. 4,826,818.

A sodium dextranmethylcarboxylate, synthesized according to the process described in Example A1 using a dextran with a weight-average molecular weight of approximately 5 kg/mol (q=19, Pharmacosmos), modified by cetyl glycinate is obtained by a process similar to that described in Example A1.

According to the dry extract: [Polysaccharide 16]=23 mg/g
According to the acid/base titration: n=1.05
According to the $^1$H NMR: m=0.05.

Example A17

Preparation of Polysaccharide 17

10 g (i.e., 185 mmol of hydroxyls) of dextran with a weight-average molar mass of approximately 10 kg/mol (q=38, Pharmacosmos) are dissolved in water at 420 g/l. 19 ml of 10N NaOH (185 mmol) are added to the solution. The mixture is brought to 35° C. and then 8.6 g (74 mmol) of sodium chloroacetate are added. The temperature of the reaction mixture is brought to 60° C. at 0.5° C./min and is then maintained at 60° C. for 100 minutes. The reaction medium is diluted with 200 ml of water, neutralized with acetic acid and purified by ultrafiltration through a 5 kDa PES membrane against 6 volumes of water. The final solution is assayed by dry extract, to determine the polysaccharide concentration, and then assayed by acid/base titration in 50/50 (V/V) water/acetone, to determine the mean number of methylcarboxylate units per glucoside unit.

According to the dry extract: [polysaccharide]=35.1 mg/g
According to the acid/base titration: the mean number of methylcarboxylate units per glucoside unit is 0.42.

The sodium dextranmethylcarboxylate solution is passed through a Purolite resin (anionic) in order to obtain dextranmethylcarboxylic acid, which is subsequently lyophilized for 18 hours.

Cetyl glycinate, para-toluenesulphonic acid salt, is obtained according to the process described in U.S. Pat. No. 4,826,818.

A sodium dextranmethylcarboxylate modified by cetyl glycinate is obtained by a process similar to that described in Example A1.

According to the dry extract: [Polysaccharide 17]=18 mg/g
According to the acid/base titration: n=0.37
According to the $^1$H NMR: m=0.05.

Example A18

Preparation of Polysaccharide 18

10 g of sodium dextranmethylcarboxylate, characterized by a degree of substitution as methylcarboxylate of 1.10 per glucoside unit, are synthesized from a dextran with a weight-average molar mass of 5 kg/mol (q=19, Pharmacosmos), according to a process similar to that described for Polysaccharide 1, and then lyophilized.

8 g (i.e., 64 mmol of hydroxyls) of sodium dextranmethylcarboxylate, characterized by a degree of substitution as methylcarboxylate of 1.10 per glucoside unit, are dissolved in water at 1000 g/l. 6 ml of 10N NaOH (64 mmol) are added. The mixture is heated to 35° C. and 7.6 g of sodium chloroacetate (65 mmol) are added. The mixture is gradually brought to a temperature of 60° C., and is maintained at this temperature for an additional 100 minutes. The mixture is diluted with water, neutralized with acetic acid and then purified by ultrafiltration through a 5 kDa PES membrane against water. The final solution is assayed by dry extract, to determine the polysaccharide concentration, and then assayed by acid/base titration in 50/50 (V/V) water/acetone, to determine the mean number of methylcarboxylate units per glucoside unit.

According to the dry extract: [polysaccharide]=45.8 mg/g
According to the acid/base titration: the mean number of methylcarboxylate units per glucoside unit is 1.65.

The sodium dextranmethylcarboxylate solution is passed through a Purolite resin (anionic) in order to obtain dextranmethylcarboxylic acid, which is subsequently lyophilized for 18 hours.

Cholesteryl leucinate, para-toluenesulphonic acid salt, is obtained according to the process described in U.S. Pat. No. 4,826,818.

A sodium dextranmethylcarboxylate modified by cholesteryl leucinate, is obtained by a process similar to that described in Example A1.

According to the dry extract: [Polysaccharide 18]=21 mg/g
According to the acid/base titration: n=1.61
According to the $^1$H NMR: m=0.04.

Example A19

Preparation of Polysaccharide 19

A sodium dextranmethylcarboxylate, synthesized according to the process described in Example A1 using a dextran with a weight-average molecular weight of approximately 5 kg/mol (q=19, Pharmacosmos), modified by cholesteryl leucinate, is obtained by a process similar to that described in Example A1.

According to the dry extract: [Polysaccharide 19]=19.4 mg/g
According to the acid/base titration: n=1.06
According to the $^1$H NMR: m=0.04.

Example A20

Preparation of Polysaccharide 20

16 g (i.e., 296 mmol of hydroxyls) of dextran with a weight-average molar mass of approximately 5 kg/mol (q=19, Pharmacosmos) are dissolved in water at 420 g/l. 30 ml of 10N NaOH (296 mmol) are added to this solution. The mixture is brought to 35° C. and then 26 g (222 mmol) of sodium chloroacetate are added. The temperature of the reaction medium is gradually brought to 60° C. and then maintained at 60° C. for 100 minutes. The reaction medium is diluted with water, neutralized with acetic acid and purified by ultrafiltration through a 5 kDa PES membrane against water. The final solution is assayed by dry extract, to determine the polysaccharide concentration, and then assayed by acid/base titration in 50/50 (V/V) water/acetone, to determine the mean number of methylcarboxylate units per glucoside unit.

According to the dry extract: [polysaccharide]=33.1 mg/g
According to the acid/base titration: the mean number of methylcarboxylate units per glucoside unit is 0.70.

The sodium dextranmethylcarboxylate solution is passed through a Purolite resin (anionic) in order to obtain dextranmethylcarboxylic acid, which is subsequently lyophilized for 18 hours.

A sodium dextranmethylcarboxylate modified by cholesteryl leucinate is obtained by a process similar to that described in Example A1.

According to the dry extract: [Polysaccharide 20]=18.9 mg/g
According to the acid/base titration: n=0.66
According to the $^1$H NMR: m=0.04.

Example A21

Preparation of Polysaccharide 21

16 g (i.e., 296 mmol of hydroxyls) of dextran with a weight-average molar mass of approximately 5 kg/mol (q=19, Pharmacosmos) are dissolved in water at 420 g/l. 30 ml of 10N NaOH (296 mmol) are added to this solution. The mixture is brought to 35° C. and then 18 g (158 mmol) of sodium chloroacetate are added. The temperature of the reaction medium is gradually brought to 60° C. and then maintained at 60° C. for 100 minutes. The reaction medium is diluted with water, neutralized with acetic acid and purified by ultrafiltration through a 1 kDa PES membrane against water. The final solution is assayed by dry extract, to determine the polysaccharide concentration, and then assayed by acid/base titration in 50/50 (V/V) water/acetone, to determine the mean number of methylcarboxylate units per glucoside unit.

According to the dry extract: [polysaccharide]=52.6 mg/g
According to the acid/base titration: the mean number of methylcarboxylate units per glucoside unit is 0.50.

The sodium dextranmethylcarboxylate solution is passed through a Purolite resin (anionic) in order to obtain dextranmethylcarboxylic acid, which is subsequently lyophilized for 18 hours.

A sodium dextranmethylcarboxylate modified by cholesteryl leucinate is obtained by a process similar to that described in Example A1.

According to the dry extract: [Polysaccharide 21]=18.9 mg/g
According to the acid/base titration: n=0.46
According to the $^1$H NMR: m=0.04.

Example A22

Preparation of Polysaccharide 22

A sodium dextranmethylcarboxylate, synthesized according to the process described in Example A18 using a dextran with a weight-average molecular weight of approximately 1 kg/mol (q=4, Pharmacosmos), modified by cholesteryl leucinate, is obtained by a process similar to that described in Example A18.

According to the dry extract: [Polysaccharide 22]=20.2 mg/g
According to the acid/base titration: n=1.61
According to the $^1$H NMR: m=0.04.

Example A23

Preparation of Polysaccharide 23

Cholesteryl 1-ethylenediaminecarboxylate hydrochloride is obtained according to the process described in the patent (Akiyoshi, K et al., WO 2010/053140).

A sodium dextranmethylcarboxylate, synthesized according to the process described in Example A 18 using a dextran with a weight-average molecular weight of approximately 5 kg/mol (q=19, Pharmacosmos), modified by cholesteryl 1-ethylenediaminecarboxylate, is obtained by a process similar to that described in Example A18.

According to the dry extract: [Polysaccharide 23]=20.1 mg/g
According to the acid/base titration: n=1.61
According to the $^1$H NMR: m=0.04.

Example A24

Preparation of Polysaccharide 24

12 g (i.e., 0.22 mol of hydroxyls) of dextran with a weight-average molar mass of approximately 5 kg/mol (q=19, Pharmacosmos) are dissolved in a DMF/DMSO mixture. The mixture is brought to 80° C. with stirring. 3.32 g (0.03 mol) of 1,4-diazabicyclo[2.2.2]octane and then 26.8 g (0.21 mol) of ethyl isocyanatoacetate are gradually introduced. After reacting for 5 h, the medium is diluted in water and purified by diafiltration through a 5 kDa PES membrane against 0.1N NaOH, 0.9% NaCl and water. The final solution is assayed by dry extract, to determine the concentration of polysaccharide; and then assayed by acid/base titration in 50/50 (V/V) water/acetone, to determine the mean number of N-methylcarboxylate carbamate units per glucoside unit.

According to the dry extract: [polysaccharide]=30.1 mg/g
According to the acid/base titration: the mean number of N-methylcarboxylate carbamate units per glucoside unit is 2.0.

An N-(sodium methylcarboxylate) dextran carbamate modified by cholesteryl leucinate is obtained by a process similar to that described in Example A1.

According to the dry extract: [Polysaccharide 24]=17.9 mg/g
According to the acid/base titration: n=1.96
According to the $^1$H NMR: m=0.04.

Example A25

Preparation of Polysaccharide 25

Cholesteryl 1-ethylenediaminecarboxylate hydrochlorate is obtained according to the process described in the patent (Akiyoshi, K et al., WO 2010/053140). 10 g of dextran with a weight-average molar mass of approximately 5 kg/mol (q=19, Pharmacosmos, 3.2 mmol of chain ends) are dissolved in DMSO at 80° C. 4.8 g of cholesteryl 1-ethylenediaminecarboxylate hydrochloride (9.5 mmol), 0.96 g of triethylamine (9.5 mmol) and 2.0 g of sodium cyanoborohydride (32 mmol) are added to the reaction medium, which is stirred at 80° C. for 24 hours. After cooling, the mixture is precipitated from dichloromethane and then from acetone, and dried under vacuum. According to the $^1$H NMR, a dextran modified at the chain end by cholesteryl 1-ethylenediaminecarboxylate is obtained. A sodium dextranmethylcarboxylate characterized by a degree of substitution as methylcarboxylate of 1.65 per glucoside unit and modified at the chain end by cholesteryl 1-ethylenediaminecarboxylate was synthesized by a process similar to that described in Example A18 using the dextran modified at the chain end by cholesteryl 1-ethylenediaminecarboxylate.

According to the dry extract: [Polysaccharide 25]=13.7 mg/g
According to the acid/base titration: n=1.65
According to the $^1$H NMR: each polymer chain carries a cholesteryl 1-ethylenediaminecarboxylate group grafted to the reducing chain end.

Example A26

Preparation of Polysaccharide 26

Cholesterol leucinate, para-toluenesulphonic acid salt, is obtained according to the process described in U.S. Pat. No. 4,826,818.

A sodium dextranmethylcarboxylate, synthesized according to the process described in Example A1 using a dextran with a weight-average molecular weight of approximately 10 kg/mol (q=38, Pharmacosmos), modified by cholesterol leucinate, is obtained by a process similar to that described in Example A1.

According to the dry extract: [Polysaccharide 26]=26.6 mg/g
According to the acid/base titration: n=0.99
According to the $^1$H NMR: m=0.05.

Example A27

Preparation of Polysaccharide 27

Dilauryl aspartate, para-toluenesulphonic acid salt, is obtained according to the process described in U.S. Pat. No. 4,826,818.

A sodium dextranmethylcarboxylate, synthesized according to the process described in Example A18 using a dextran with a weight-average molecular weight of approximately 1 kg/mol (q=4, Pharmacosmos), modified by dilauryl aspartate, is obtained by a process similar to that described in Example A1.

According to the dry extract: [Polysaccharide 27]=16.7 mg/g
According to the acid/base titration: n=1.41
According to the $^1$H NMR: m=0.16.

Example A28

Preparation of Polysaccharide 28

Dilauryl aspartate, para-toluenesulphonic acid salt, is obtained according to the process described in U.S. Pat. No. 4,826,818.

A sodium dextranmethylcarboxylate, synthesized according to the process described in Example A18 using a dextran with a weight-average molecular weight of approximately 1 kg/mol (q=4, Pharmacosmos), modified by dilauryl aspartate, is obtained by a process similar to that described in Example A1.

According to the dry extract: [Polysaccharide 28]=25 mg/g
According to the acid/base titration: n=1.50
According to the $^1$H NMR: m=0.07.

Example A29

Preparation of Polysaccharide 29

Didecyl aspartate, para-toluenesulphonic acid salt, is obtained according to the process described in U.S. Pat. No. 4,826,818.

A sodium dextranmethylcarboxylate, synthesized according to the process described in Example A1 using a dextran with a weight-average molecular weight of approximately 1 kg/mol (q=4, Pharmacosmos), modified by didecyl aspartate, is obtained by a process similar to that described in Example A1.

According to the dry extract: [Polysaccharide 29]=15 mg/g
According to the acid/base titration: n=1.05
According to the $^1$H NMR: m=0.05.

EXAMPLES

Part B

Demonstration of the Properties of the Compositions According to the Invention

Example B1

Solution of Rapid-Acting Insulin Analogue (NovoLog®) at 100 IU/ml

This solution is a commercial solution of insulin aspart, sold by the company Novo Nordisk under the name of NovoLog® in the USA and Novorapid® in Europe. This product is a rapid-acting insulin analogue.

Example B2

Solution of Rapid-Acting Insulin Analogue (Humalog®) at 100 IU/ml

This solution is a commercial solution of insulin lispro, sold by the company Eli Lilly under the name of Humalog®. This product is a rapid-acting insulin analogue.

Example B3

Solution of Rapid-Acting Insulin Analogue (Apidra®) at 100 IU/ml

This solution is a commercial solution of insulin glulisine, sold by the company Sanofi-Aventis under the name of Apidra®. This product is a rapid-acting insulin analogue.

Example B4

Solution of Slow-Acting Insulin Analogue (Lantus®) at 100 IU/ml

This solution is a commercial solution of insulin glargine, sold by the company Sanofi-Aventis under the name of Lantus®. This product is a slow-acting insulin analogue.

Example B5

Solution of Human Insulin (ActRapid®) at 100 IU/ml

This solution is a commercial solution from Novo Nordisk, sold under the name of Actrapid®. This product is a human insulin.

Example B6

Dissolution of Lantus® at 100 IU/ml and at pH 7 Using a Substituted Dextran 20 mg of Polysaccharide 4 described in Example A4 are weighed out accurately. This lyophilisate is taken up in 2 ml of Lantus® in its commercial formulation. A transient precipitate appears but the solution becomes clear after approximately 30 minutes. The pH of this solution is 6.3. The pH is adjusted to 7 with a 0.1N sodium hydroxide solution. This clear solution is filtered through a 0.22 µm filter and is then placed at +4° C.

Example B7

Preparation of a Substituted Dextran/Lantus®/Apidra® 75/25 Composition at pH 7

0.25 ml of Apidra® (in its commercial formulation) is added to 0.75 ml of the Polysaccharide 4/Lantus® solution prepared in Example B6, in order to form 1 ml of a composition at pH 7. The composition is clear, testifying to the good solubility of Lantus® and Apidra® under these formulation conditions. This clear solution is filtered through a 0.22 µm filter and is then placed at +4° C.

Example B8

Preparation of a Substituted Dextran/Lantus®/Humalog® 75/25 Composition at pH 7

0.25 ml of Humalog® (in its commercial formulation) is added to 0.75 ml of the Polysaccharide 4/Lantus® solution prepared in Example B6, in order to form 1 ml of a composition at pH 7. The composition is clear, testifying to the good solubility of Lantus® and Humalog® under these formulation conditions. This clear solution is filtered through a 0.22 µm filter and is then placed at +4° C.

Example B9

Preparation of a Substituted Dextran/Lantus®/NovoLog® 75/25 Composition at pH 7

0.25 ml of NovoLog® (in its commercial formulation) is added to 0.75 ml of the Polysaccharide 4/Lantus® solution prepared in Example B6, in order to form 1 ml of a composition at pH 7. The composition is clear, testifying to the good solubility of Lantus® and NovoLog® under these formulation conditions. This clear solution is filtered through a 0.22 µm filter and is then placed at +4° C.

Example B10

Preparation of a Substituted Dextran/Lantus®/ActRapid® 75/25 Composition at pH 7

0.25 ml of ActRapid® (in its commercial formulation) is added to 0.75 ml of the Polysaccharide 4/Lantus® solution prepared in Example B6, in order to form 1 ml of a composition at pH 7. The composition is clear, testifying to the good solubility of Lantus® and ActRapid® under these formulation conditions. This clear solution is filtered through a 0.22 µm filter and is then placed at +4° C.

Example B11

Preparation of a Substituted Dextran/Lantus®/Apidra® 60/40 Composition at pH 7

0.4 ml of Apidra® (in its commercial formulation) is added to 0.6 ml of the Polysaccharide 4/Lantus® solution prepared in Example B6, in order to form 1 ml of a composition at pH 7. The composition is clear, testifying to the good solubility of Lantus® and Apidra® under these formulation conditions. This clear solution is filtered through a 0.22 µm filter and is then placed at +4° C.

Example B12

Preparation of a Substituted Dextran/Lantus®/Apidra® 40/60 Composition at pH 7

0.6 ml of Apidra® (in its commercial formulation) is added to 0.4 ml of the Polysaccharide 4/Lantus® solution prepared in Example B6, in order to form 1 ml of a composition at pH 7. The composition is clear, testifying to the good solubility of Lantus® and Apidra® under these formulation conditions. This clear solution is filtered through a 0.22 µm filter and is then placed at +4° C.

Example B13

Precipitation of Lantus®

1 ml of Lantus® is added to 2 ml of a PBS solution containing 20 mg/ml of BSA (bovine serum albumin). The PBS/BSA mixture simulates the composition of the subcutaneous medium. A precipitate appears, which is in good agreement with the mechanism of operation of Lantus® (precipitation on injection due to the increase in the pH).

Centrifuging at 4000 rev/min is carried out in order to separate the precipitate from the supernatent. Subsequently, Lantus® is assayed in the supernatent. The result of this is that 86% of Lantus® is found in a precipitated form.

Example B14

Precipitation of a Substituted Dextran/Lantus® Composition 1 ml of Polysaccharide 4/Lantus® solution prepared in Example B6 is added to 2 ml of a PBS solution containing 20 mg/ml of BSA (bovine serum albumin). The PBS/BSA mixture simulates the composition of the subcutaneous medium. A precipitate appears.

Centrifuging at 4000 rev/min is carried out in order to separate the precipitate from the supernatent. Subsequently, Lantus® is assayed in the supernatent. The result of this is that 85% of Lantus® is found in a precipitated form. This percentage of precipitation of Lantus® is identical to that obtained for the control described in Example B13.

Dissolution and precipitation tests identical to those described in Examples B6 and B14 were carried out with other substituted dextrans at the same concentration of 10 mg/ml of polysaccharide per 100 IU/ml of Lantus®. 20 mg of polysaccharide in the lyophilisate form are weighed out accurately. This lyophilisate is taken up in 2 ml of Lantus® in its commercial formulation. A transient precipitate appears but the solution becomes clear after approximately 30 minutes to a few hours (depending on the nature of the polysaccharide). The pH of this solution is 6.3. The pH is adjusted to 7 with a 0.1N sodium hydroxide solution. This clear solution is filtered through a 0.22 µm filter and is then placed at +4° C. The results are collated in Table 2.

TABLE 2

| Polysaccharide No. | Dissolution of Lantus ® | Precipitation of Lantus ® | % of precipitation |
| --- | --- | --- | --- |
| 2 | Yes | Yes | 85 |
| 1 | Yes | Yes | Not measured |
| 4 | Yes | Yes | 87 |
| 3 | Yes | Yes | Not measured |
| 5 | Yes | Yes | 94 |
| 6 | Yes | Yes | Not measured |
| 7 | Yes | Yes | Not measured |
| 8 | Yes | Yes | Not measured |
| 9 | Yes | Yes | 94 |
| 10 | Yes | Yes | Not measured |
| 15 | Yes | Yes | Not measured |
| 14 | Yes | Yes | Not measured |
| 13 | Yes | Yes | Not measured |
| 12 | Yes | Yes | Not measured |
| 11 | Yes | Yes | Not measured |
| 16 | Yes | Yes | Not measured |
| 17 | Yes | Yes | Not measured |
| 18 | Yes | Yes | Not measured |
| 19 | Yes | Yes | Not measured |
| 20 | Yes | Yes | Not measured |
| 21 | Yes | Yes | Not measured |
| 22 | Yes | Yes | Not measured |
| 23 | Yes | Yes | Not measured |
| 24 | Yes | Yes | Not measured |
| 25 | Yes | Yes | Not measured |
| 26 | Yes | Yes | Not measured |

Example B15

Precipitation of a Substituted Dextran/Lantus®/Apidra® 75/25 Composition at pH 7

1 ml of the substituted dextran/Lantus®/Apidra® 75/25 composition (containing 7.5 mg/ml of polysaccharide, 75 IU/ml of Lantus® and 25 IU/ml of Apidra®) prepared in Example B7 is added to 2 ml of a PBS solution containing 20 mg/ml of BSA (bovine serum albumin). The PBS/BSA mixture simulates the composition of the subcutaneous medium. A precipitate appears.

Centrifuging at 4000 rev/min is carried out in order to separate the precipitate from the supernatent. Subsequently, Lantus® is assayed in the supernatent. The percentages of precipitation of Lantus® are similar to the control described in Example B13.

Example B16

Precipitation of Various Compositions, the Nature of the Substituted Dextran being Varied

Other tests under the same conditions as those of Example B15 were carried out in the presence of other substituted dextrans.

The results are combined in the following Table 3 and it is observed that the dissolution and the precipitation of Lantus® are retained.

TABLE 3

| Polysaccharide No | Dissolution Lantus ®/Apidra ® 75/25 | Percentage of precipitation of Lantus ® |
| --- | --- | --- |
| 2 | Yes | 85 |
| 1 | Yes | Not measured |
| 4 | Yes | 87 |
| 3 | Yes | Not measured |
| 5 | Yes | 86 |
| 6 | Yes | Not measured |
| 7 | Yes | Not measured |
| 8 | Yes | Not measured |
| 9 | Yes | 86 |
| 10 | Yes | 85 |
| 15 | Yes | 87 |
| 14 | Yes | 86 |
| 13 | Yes | 88 |
| 12 | Yes | 91 |
| 18 | Yes | Not measured |
| 19 | Yes | Not measured |
| 20 | Yes | Not measured |
| 21 | Yes | Not measured |
| 22 | Yes | Not measured |
| 23 | Yes | Not measured |
| 24 | Yes | Not measured |
| 25 | Yes | Not measured |
| 26 | Yes | Not measured |

Example B17

Precipitation of Various Compositions, the Nature of the Prandial Insulin being Varied

Compositions are prepared by mixing 0.75 ml of the Polysaccharide 4/Lantus® solution prepared in Example B6 with 0.25 ml of a prandial insulin in order to form 1 ml of substituted dextran/Lantus®/prandial insulin composition (containing 7.5 mg/ml of polysaccharide, 75 IU/ml of Lantus® and 25 IU/ml of prandial insulin).

This composition is added to 2 ml of PBS solution containing 20 mg/ml of BSA (bovine serum albumin). The PBS/BSA mixture simulates the composition of the subcutaneous medium. A precipitate appears.

Centrifuging at 4000 rev/min is carried out in order to separate the precipitate from the supernatent. Subsequently, Lantus® is assayed in the supernatent. In the presence of the four prandial insulins tested, Lantus® precipitates to approximately 90%. This percentage of precipitation of Lantus® is similar to the control described in Example B13; the results are collated in Table 4.

TABLE 4

| Nature of the prandial insulin | Dissolution Lantus ®/prandial insulin 75/25 | Percentage of precipitation of Lantus ® |
| --- | --- | --- |
| Apidra ® | Yes | 88 |
| NovoLog ® | Yes | 92 |
| Humalog ® | Yes | 89 |
| ActRapid ® | Yes | 90 |

Example B18

Preparation of a Concentrated Solution of Slow-Acting Insulin Analogue (Glargine)

A commercial solution of insulin glargine, sold by the company Sanofi-Aventis under the name of Lantus®, is concentrated by ultrafiltration through a 3 kDa membrane made of regenerated cellulose (Amicon® Ultra-15, sold by the company Millipore). On conclusion of this ultrafiltration stage, the concentration of insulin glargine is assayed in the retentate by reverse phase liquid chromatography (RP-HPLC). The final concentration of insulin glargine is subsequently adjusted by the addition of commercial 100 IU/ml glargine solution in order to obtain the desired final concentration. This process makes it possible to obtain concentrated solutions of glargine, denoted $C_{glargine}$, at various concentrations of greater than 100 IU/ml, such as $C_{glargine}$=200, 250, 300 and 333 IU/ml. The concentrated solutions are filtered through a 0.22 μm filter and then stored at +4° C.

Example B19

Dialysis of a Commercial Solution of Rapid-Acting Insulin Analogue (Lispro)

A commercial solution of insulin lispro, sold by the company Lilly under the name of Humalog® is dialyzed by ultrafiltration through a 3 kDa membrane made of regenerated cellulose (Amicon® Ultra-15, sold by the company Millipore). The dialysis is carried out in a 1 mM phosphate buffer at pH 7. On conclusion of this dialysis stage, the concentration $C_{dialyzed\ Humalog}$ of lispro in the retentate is determined by reverse phase liquid chromatography (RP-HPLC). The dialyzed solution is stored in a freezer at −80° C.

Example B20

Lyophilization of a Solution of Rapid-Acting Insulin Analogue (Lispro) in its Commercial Form

A volume $V_{Humalog}$ of a solution of rapid-acting insulin lispro at a concentration of 100 IU/ml in its commercial form is placed in a Lyoguard® sterilized beforehand in an autoclave. The Lyoguard® is placed in a freezer at −80° C. for approximately 1 h before being subjected to lyophilization overnight at a temperature of 20° C. and a pressure of 0.31 mbar.

The sterile lyophilisate thus obtained is stored at ambient temperature.

Example B21

Lyophilization of a Dialyzed Commercial Solution of Rapid-Acting Insulin Analogue (Lispro)

A volume $V_{dialyzed\ Humalog}$ of a solution of rapid-acting insulin lispro obtained according to Example B19 at a concentration of $C_{dialyzed\ Humalog}$ is placed in a Lyoguard® sterilized beforehand in an autoclave. The Lyoguard® is placed in a freezer at −80° C. for approximately 1 h before being subjected to lyophilization overnight at a temperature of 20° C. and a pressure of 0.31 mbar.

The sterile lyophilisate thus obtained is stored at ambient temperature.

Example B22

Preparation of a Substituted Dextran/Glargine Composition at pH 7 Using a Substituted Dextran, According to a Process Using Glargine in the Liquid Form (in Solution) and a Polysaccharide in the Solid Form (Lyophilized)

A weight $w_{polys.}$ of Polysaccharide 18 is weighed out accurately. This lyophilisate is taken up in a volume $V_{glargine}$ of a concentrated solution of glargine prepared according to Example B18, so as to obtain a composition exhibiting a concentration of polysaccharide $C_{polys.}$ (mg/ml)=$w_{polys.}$/$V_{glargine}$ and a concentration of glargine $C_{glargine}$ (IU/ml). The solution is opalescent. The pH of this solution is approximately 6.3. The pH is adjusted to 7 by addition of concentrated NaOH and then the solution is placed under static conditions in an oven at 37° C. for approximately 1 hour. A volume $V_{polys./glargine}$ of this visually clear solution is placed at +4° C.

Example B23

Preparation of a Substituted Dextran/Glargine Composition at pH 7 Using a Substituted Dextran, According to a Process Using Glargine in the Liquid Form (in Solution) and a Polysaccharide in the Liquid Form (in Solution)

Concentrated solutions of m-cresol, glycerol and tween 20 are added to a mother solution of polysaccharide 20 at pH 7 exhibiting a concentration $C_{polys.\ mother}$, so as to obtain a polysaccharide solution having the concentration $C_{polys.\ mother/excipients}$ (mg/ml) in the presence of these excipients at contents equivalent to those described in the Lantus® commercial solution in a 10 ml bottle.

A volume $V_{Lantus}$ of a commercial solution of slow-acting insulin glargine, sold under the name of Lantus® at a concentration de 100 IU/ml, is added to a volume $V_{polys.\ mother/excipients}$ of a polysaccharide solution at the concentration $C_{polys.\ mother/excipients}$ (mg/ml) in a sterile flask. A cloudiness appears. The pH is adjusted to pH 7 by addition of 1M NaOH and the solution is placed under static conditions in an oven at 37° C. for approximately 1 h. This visually clear solution is placed at +4° C.

Example B24

Preparation of a Concentrated Polysaccharide/Glargine Composition at pH=7 Using a Substituted Dextran, According to a Process for the Concentration of a Dilute Composition A dilute Polysaccharide 20/glargine composition at pH 7 described in Example B23 is concentrated by ultrafiltration through a 3 kDa membrane made of regenerated cellulose (Amicon® Ultra-15, sold by the company Millipore). On conclusion of this ultrafiltration stage, the retentate is clear and the concentration of insulin glargine in the composition is assayed by reverse phase chromatography (RP-HPLC). If necessary, the concentration of insulin glargine in the composition is subsequently adjusted to the desired value by diluting in a solution of m-cresol/glycerol/tween 20 excipients exhibiting, for each entity, a concentration equivalent to that described in the Lantus® commercial solution (in a 10 ml bottle). This solution at pH 7, which is visually clear, exhibiting a glargine concentration $C_{glargine}$ (IU/ml) and a polysaccharide concentration $C_{polys.}$ (mg/ml), is placed at +4° C.

Example B25

Preparation of a Substituted Dextran/Glargine/Lispro Composition at pH 7, Starting from a Rapid-Acting Insulin Lispro in its Commercial Form A volume $V_{polysach./glargine}$ of polysaccharide/glargine solution, pH 7, exhibiting a concentration of glargine $C_{glargine}$ (IU/ml) and a concentration of Polysaccharide 18 $C_{polys.}$ (mg/ml), prepared according to Example B22, is added to an insulin lispro lyophilisate obtained by lyophilization of a volume $V_{lispro}$, the preparation of which is described in Example B19, so that the ratio $V_{polysach./glargine}/V_{lispro}$=100/$C_{lispro}$, where $C_{lispro}$ is the concentration of lispro (IU/ml) targeted in the composition. The solution is clear. The zinc content of the formulation is adjusted to the desired concentration $C_{zinc}$ (µM) by addition of a concentrated zinc chloride solution. The final pH is adjusted to 7 by addition of concentrated NaOH or HCl.

The formulation is clear, testifying to the good solubility of glargine and lispro under these formulation conditions. This solution is filtered through a 0.22 µm filter and is placed at +4° C.

Example B26

Preparation of a Substituted Dextran/Glargine/Lispro Composition at pH 7, Starting from a Rapid-Acting Insulin Lispro Obtained by Dialysis of a Commercial Solution A volume $V_{polysach./glargine}$ of polysaccharide/glargine solution, pH 7, exhibiting a concentration of $C_{glargine}$ (IU/ml) and a concentration of Polysaccharide 20 $C_{polys.}$ (mg/ml), prepared according to Example B24, is added to an insulin lispro lyophilisate obtained by lyophilization of a volume $V_{dialyzed\ Humalog}$, the preparation of which is described in Example B21, so that the ratio $V_{polysach./glargine}/V_{dialyzed\ Humalog}$=$C_{dialyzed\ Humalog}/C_{lispro}$, where $C_{dialyzed\ Humalog}$ is the concentration of lispro (IU/ml) obtained on conclusion of the dialysis of the commercial solution, which stage is described in Example B19, and $C_{lispro}$ is the concentration of lispro (IU/ml) targeted in the composition. The solution is clear. The zinc content of the formulation is adjusted to the desired concentration $C_{zinc}$ (µM) by addition of a concentrated zinc chloride solution. The final pH is adjusted to 7 by addition of concentrated NaOH or HCl.

The formulation is clear, testifying to the good solubility of glargine and lispro under these formulation conditions. This solution is filtered through a 0.22 µm filter and is placed at +4° C.

Example B27

Preparation of a Substituted Dextran/Glargine/Lispro Composition at pH 7 Exhibiting a Concentration of Glargine of 200 IU/ml and a Concentration of Lispro of 33 IU/ml (Proportion as Percentage of Insulin: 85/15 as Glargine/Lispro)

A concentrated 200 IU/ml glargine solution is prepared according to Example B18. A Polysaccharide 18 (13 mg/ml)/ glargine 300 IU/ml composition, pH 7, is prepared from Polysaccharide 18 according to the method of preparation described in Example B22. This Polysaccharide 18/glargine 200 IU/ml composition is added to an insulin lispro lyophilisate obtained by lyophilization of the solution of rapid-acting analogue in its commercial form, according to the method of preparation described in Example B25. The solution is clear. The zinc content of the formulation is adjusted to the concentration $C_{zinc}$ (µM)=750 µM by addition of a concentrated zinc chloride solution. The final pH is adjusted to 7 by addition of concentrated NaOH or HCl.

This composition is described in Table 5.

Example B28

Preparation of a Substituted Dextran/Glargine/Lispro Composition at pH 7 Exhibiting a Concentration of Glargine of 200 IU/ml and a Concentration of Lispro of 66 IU/ml (Proportion as Percentage of Insulin: 75/25 as Glargine/Lispro)

A concentrated 200 IU/ml glargine solution is prepared according to Example B18. A Polysaccharide 18 (13 mg/ml)/glargine 300 IU/ml composition, pH 7, is prepared from Polysaccharide 18 according to the method of preparation described in Example B22. This Polysaccharide 18/glargine 200 IU/ml composition is added to an insulin lispro lyophilisate obtained by lyophilization of the solution of rapid-acting analogue in its commercial form, according to the method of preparation described in Example B25. The solution is clear. The zinc content of the formulation is adjusted to the concentration $C_{zinc}$ (µM)=1500 µM by addition of a concentrated zinc chloride solution. The final pH is adjusted to 7 by addition of concentrated NaOH or HCl.

The formulation is clear, testifying to the good solubility of glargine and lispro under these formulation conditions. This solution is filtered through a 0.22 µm filter and is placed at +4° C.

This composition is described in Table 5.

Example B29

Preparation of a Substituted Dextran/Glargine/Lispro Composition at pH 7 Exhibiting a Concentration of Glargine of 300 IU/ml and a Concentration of Lispro of 100 IU/ml (Proportion as Percentage of Insulin: 75/25 as Glargine/Lispro)

A concentrated 300 IU/ml glargine solution is prepared according to Example B18. A Polysaccharide 18 (23 mg/ml)/glargine 300 IU/ml composition, pH 7, is prepared from Polysaccharide 18 according to the method of preparation described in Example B22. This Polysaccharide 18/glargine 300 IU/ml composition is added to an insulin lispro lyophilisate obtained by lyophilization of the solution of rapid-acting analogue in its commercial form, according to the method of preparation described in Example B25. The solution is clear. The zinc content of the formulation is adjusted to the concentration $C_{zinc}$ (µM)=2000 µM by addition of a concentrated zinc chloride solution. The final pH is adjusted to 7 by addition of concentrated NaOH or HCl.

The formulation is clear, testifying to the good solubility of glargine and lispro under these formulation conditions. This solution is filtered through a 0.22 µm filter and is placed at +4° C.

This composition is described in Table 5.

Example B30

Preparation of a Substituted Dextran/Glargine/Lispro Composition at pH 7 Exhibiting a Concentration of Glargine of 250 IU/ml and a Concentration of Lispro of 150 IU/ml (Proportion as Percentage of Insulin: 63/37 as Glargine/Lispro)

A concentrated 300 IU/ml glargine solution is prepared according to Example B18. A Polysaccharide 18 (19 mg/ml)/glargine 300 IU/ml composition, pH 7, is prepared from Polysaccharide 18 according to the method of preparation described in Example B22. This Polysaccharide 18/glargine 250 IU/ml composition is added to an insulin lispro lyophilisate obtained by lyophilization of the solution of rapid-acting analogue in its commercial form, according to the method of preparation described in Example B25. The solution is clear. The zinc content of the formulation is adjusted to the concentration $C_{zinc}$ (µM)=1500 µM by addition of a concentrated zinc chloride solution. The final pH is adjusted to 7 by addition of concentrated NaOH or HCl.

The formulation is clear, testifying to the good solubility of glargine and lispro under these formulation conditions. This solution is filtered through a 0.22 µm filter and is placed at +4° C.

This composition is described in Table 5.

Example B31

Preparation of a Substituted Dextran/Glargine/Lispro Composition at pH 7 Exhibiting a Concentration of Glargine of 333 IU/ml and a Concentration of Lispro of 67 IU/ml (Proportion as Percentage of Insulin: 83/17 as Glargine/Lispro)

A concentrated 333 IU/ml glargine solution is prepared according to Example B18. A Polysaccharide 18 (20 mg/ml)/glargine 300 IU/ml composition, pH 7, is prepared from Polysaccharide 18 according to the method of preparation described in Example B22. This Polysaccharide 18/glargine 333 IU/ml composition is added to an insulin lispro lyophilisate obtained by lyophilization of the solution of rapid-acting analogue in its commercial form, according to the method of preparation described in Example B25. The solution is clear. The zinc content of the formulation is adjusted to the concentration $C_{zinc}$ (µM)=2000 µM by addition of a concentrated zinc chloride solution. The final pH is adjusted to 7 by addition of concentrated NaOH or HCl.

The formulation is clear, testifying to the good solubility of glargine and lispro under these formulation conditions. This solution is filtered through a 0.22 μm filter and is placed at +4° C.

This composition is described in Table 5.

Example B32

Preparation of a Substituted Dextran/Glargine/Lispro Composition at pH 7 Exhibiting a Concentration of Glargine of 300 IU/ml and a Concentration of Lispro of 100 IU/ml (Proportion as Percentage of Insulin: 75/25 as Glargine/Lispro)

A concentrated 300 IU/ml glargine solution is prepared according to Example B18. A Polysaccharide 19 (23 mg/ml)/glargine 300 IU/ml composition, pH 7, is prepared from Polysaccharide 19 according to the method of preparation described in Example B22. This Polysaccharide 19/glargine 300 IU/ml composition is added to an insulin lispro lyophilisate obtained by lyophilization of the solution of rapid-acting analogue under its dialyzed form, according to the method of preparation described in Example B26. The solution is clear. The zinc content of the formulation is adjusted to the concentration $C_{zinc}$ (μM)=3000 μM by addition of a concentrated zinc chloride solution. The final pH is adjusted to 7 by addition of concentrated NaOH or HCl.

The formulation is clear, testifying to the good solubility of glargine and lispro under these formulation conditions. This solution is filtered through a 0.22 μm filter and is placed at +4° C.

This composition is described in Table 5.

Example B33

Preparation of a Substituted Dextran/Glargine/Lispro Composition at pH 7 Exhibiting a Concentration of Glargine of 300 IU/ml and a Concentration of Lispro of 100 IU/ml (Proportion as Percentage of Insulin: 75/25 as Glargine/Lispro)

A Polysaccharide 20 (23 mg/ml)/glargine 300 IU/ml composition, pH 7, is prepared from Polysaccharide 20 according to the method of preparation described in Example B23. This Polysaccharide 20/glargine 300 IU/ml composition is added to an insulin lispro lyophilisate obtained by lyophilization of the solution of rapid-acting analogue resulting from the dialysis of a commercial solution, according to the method of preparation described in Example B26. The solution is clear. The zinc content of the formulation is adjusted to the concentration $C_{zinc}$ (μM)=1500 μM by addition of a concentrated zinc chloride solution. The final pH is adjusted to 7 by addition of concentrated NaOH or HCl.

The formulation is clear, testifying to the good solubility of glargine and lispro under these formulation conditions. This solution is filtered through a 0.22 μm filter and is placed at +4° C.

This composition is described in Table 5.

TABLE 5

Substituted dextran/glargine/lispro compositions at pH 7

| Example No. | Polysaccharide No. | $C_{polysach.}$ (mg/ml) | $C_{glargine}$ (IU/ml) | $C_{lispro}$ (IU/ml) | $C_{glargine}/C_{lispro}$ (%/%) | pH |
|---|---|---|---|---|---|---|
| B27 | 18 | 13 | 200 | 33 | 85/15 | 7 |
| B28 | 18 | 13 | 200 | 66 | 75/25 | 7 |
| B29 | 18 | 23 | 300 | 100 | 75/25 | 7 |
| B30 | 18 | 19 | 250 | 150 | 63/37 | 7 |
| B31 | 18 | 20 | 333 | 67 | 83/17 | 7 |
| B32 | 19 | 23 | 300 | 100 | 75/25 | 7 |
| B33 | 20 | 23 | 300 | 100 | 75/25 | 7 |

Example B34

Precipitation of Various Substituted Dextran/Glargine/Lispro Compositions at pH 7 Exhibiting Different Concentrations of Insulin Glargine and Insulin Lispro and Different Relative Proportions of the Two Insulins 1 ml of substituted dextran/Lantus®/Humalog® composition prepared in Examples B27 to B33 is added to 2 ml of a PBS solution containing 20 mg/ml of BSA (bovine serum albumin). The PBS/BSA mixture simulates the composition of the subcutaneous medium. A precipitate appears.

Centrifuging at 4000 rev/min is carried out in order to separate the precipitate from the supernatent. Subsequently, Lantus® is assayed in the supernatent. The percentages of precipitation of Lantus® are similar to the control described in Example B13. The results are summarized in Table 6.

TABLE 6

| Example No. | Polysaccharide No. | $C_{polysach.}$ (mg/ml) | $C_{glargine}$ (IU/ml) | $C_{lispro}$ (IU/ml) | $C_{glargine}/C_{lispro}$ (%/%) | Dissolution of glargine and of lispro at pH 7 | Precipitation of glargine | % Precipitation |
|---|---|---|---|---|---|---|---|---|
| B27 | 18 | 13 | 200 | 33 | 85/15 | YES | YES | 96 |
| B28 | 18 | 13 | 200 | 66 | 75/25 | YES | YES | 86 |
| B29 | 18 | 23 | 300 | 100 | 75/25 | YES | YES | 91 |
| B30 | 18 | 19 | 250 | 150 | 63/37 | YES | YES | 90 |
| B31 | 18 | 20 | 333 | 67 | 83/17 | YES | YES | 93 |
| B32 | 19 | 23 | 300 | 100 | 75/25 | YES | YES | 98 |
| B33 | 20 | 23 | 300 | 100 | 75/25 | YES | YES | Not measured |

Example B35

Chemical Stability of the Compositions

The substituted dextran/Lantus®/prandial insulin compositions described in Examples B7, B27, B28 and B29 and the corresponding controls are placed at 30° C. for 4 weeks. Regulations require 95% of native (nondegraded) insulin after 4 weeks at 30° C.

After 4 weeks, the formulations studied meet the specifications defined by the regulations. The results are combined in Table 7.

TABLE 7

| Compositions | Percentage of native glargine after 4 weeks at 30° C. | Percentage of native prandial insulin after 4 weeks at 30° C. |
|---|---|---|
| Lantus ® (commercial formulation) | 97 | na |
| Apidra ® (commercial formulation) | na | 95 |
| Humalog ® (commercial formulation) | na | 98 |
| B7 | 96 | 98 |
| B27 | 97 | 99 |
| B28 | 95 | 97 |
| B29 | 98 | 100 |

Thus, whatever the formulation studied, a percentage of native insulin of greater than 95% is obtained, which is in accordance with regulatory requirements.

Example B36

Injectability of the Solutions

All the compositions prepared can be injected with the normal systems for the injection of insulin. The solutions described in Examples B7 to B12 and the compositions described in Examples B27 à B33 are injected without any difficulty, both with insulin syringes equipped with 31-gauge needles and with insulin pens from Novo Nordisk, sold under the name of Novopen®, equipped with 31-gauge needles.

Example B37

Protocol for Measuring the Pharmacodynamics of the Insulin Solutions

Preclinical studies were carried out on pigs for the purpose of evaluating two compositions according to the invention:

Lantus®/Apidra® (75/25), formulated with Polysaccharide 4 (6 mg/ml), described in Example B7, and Lantus®/Humalog® (75/25), formulated with Polysaccharide 4 (6 mg/ml), described in Example B8.

The hypoglycaemic effects of these compositions were compared with respect to injections carried out with simultaneous but separate injections of Lantus® (pH 4) and then of a prandial insulin Apidra® or Humalog®.

Six domesticated pigs weighing approximately 50 kg, catheterized beforehand in the jugular vein, are deprived of food for 2 to 3 hours before the beginning of the experiment. In the hour preceding the injection of insulin, three blood samples are taken in order to determine the basal glucose level.

Injection of insulin at a dose of 0.4 IU/kg is carried out by subcutaneous injection into the neck, under the ear of the animal, using the Novopen® insulin pen equipped with at 31 G needle.

Blood samples are subsequently taken after 4, 8, 12, 16, 20, 30, 40, 50, 60, 90, 120, 240, 360, 480, 600, 660 and 720 minutes. After each sample has been taken, the catheter is rinsed with a dilute heparin solution.

A drop of blood is taken in order to determine the glycaemia using a glucose meter. The pharmacodynamic curves of glucose are subsequently plotted.

The results obtained are presented in the form of pharmacodynamic curves for glucose represented in FIGS. 1 to 6.

Lantus®/Apidra® (75/25), formulated with Polysaccharide 4 (6 mg/ml).

FIG. 1: Mean+standard deviation of the mean curves for the sequential administrations of Apidra® and Lantus®, in comparison with a composition according to the invention Polysaccharide 4/Lantus®/Apidra® (75/25).

Figure 2:
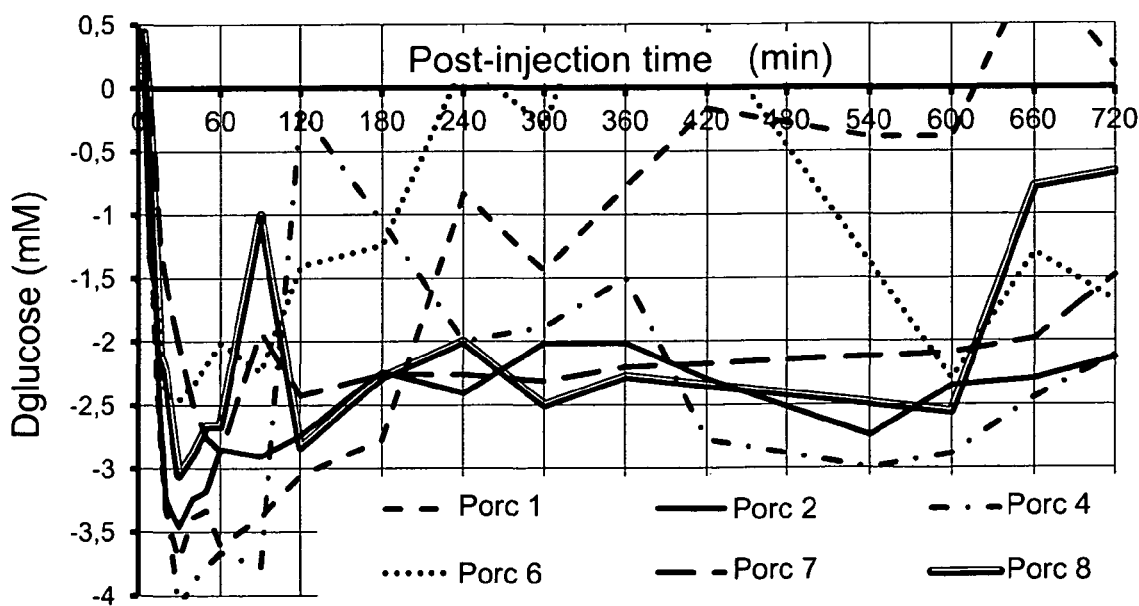

FIG. 2: Apidra® Lantus® individual curves.

Figure 3:
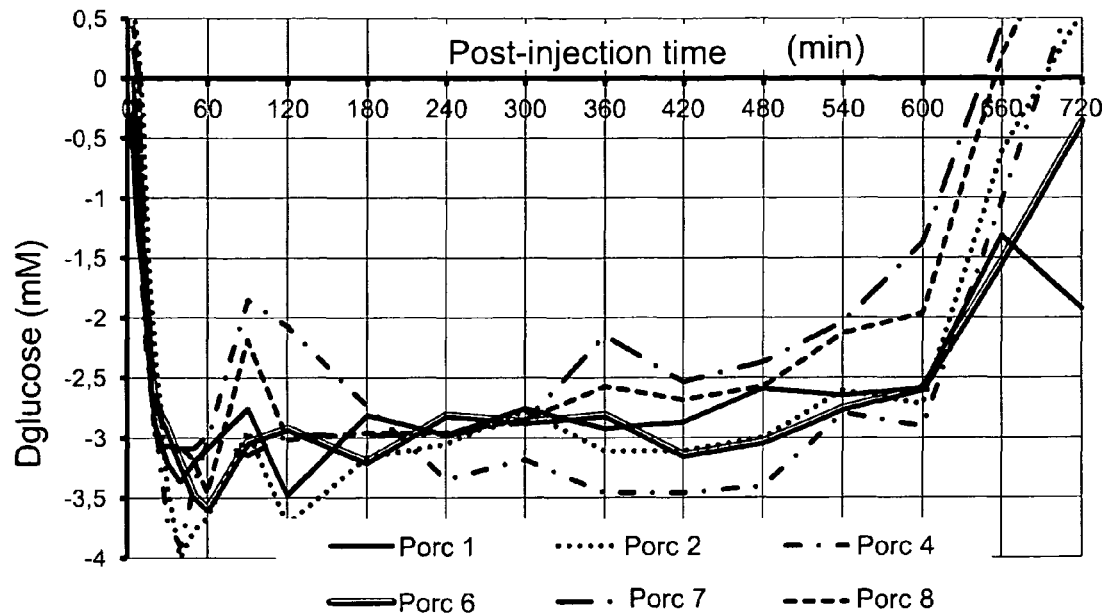

FIG. 3: Polysaccharide 4/Apidra®/Lantus® individual curves.

FIG. 1 presents the mean curves for drop in glycaemia and the standard deviations of the mean for the pigs tested for each formulation. The drop in glycaemia in the first 30 minutes is similar for the two formulations, indicating that the presence of a polysaccharide does not interfere with the rapid-acting nature of Apidra®.

On the other hand, between 90 min and 10 h (600 minutes), the sequential administration of Apidra® and Lantus® brings about a heterogeneous drop in glucose with a homogeneous plateau response with regard to three pigs and a heterogeneous response with regard to the other three pigs (FIG. 2). In contrast, the six pigs tested with the Polysaccharide 4/Apidra®/Lantus® formulation have a homogeneous response (FIG. 3). This is reflected by the analysis of the coefficients of variation (CV) between 60 min and 10 h, which are on average 54% (between 21% and 113%) for the Apidra® Lantus® control and 12% (between 5% and 25%) for Polysaccharide 4/Apidra®/Lantus®.

Lantus®/Humalog® (75/25), formulated with Polysaccharide 4 (6 mg/ml).

Figure 4:
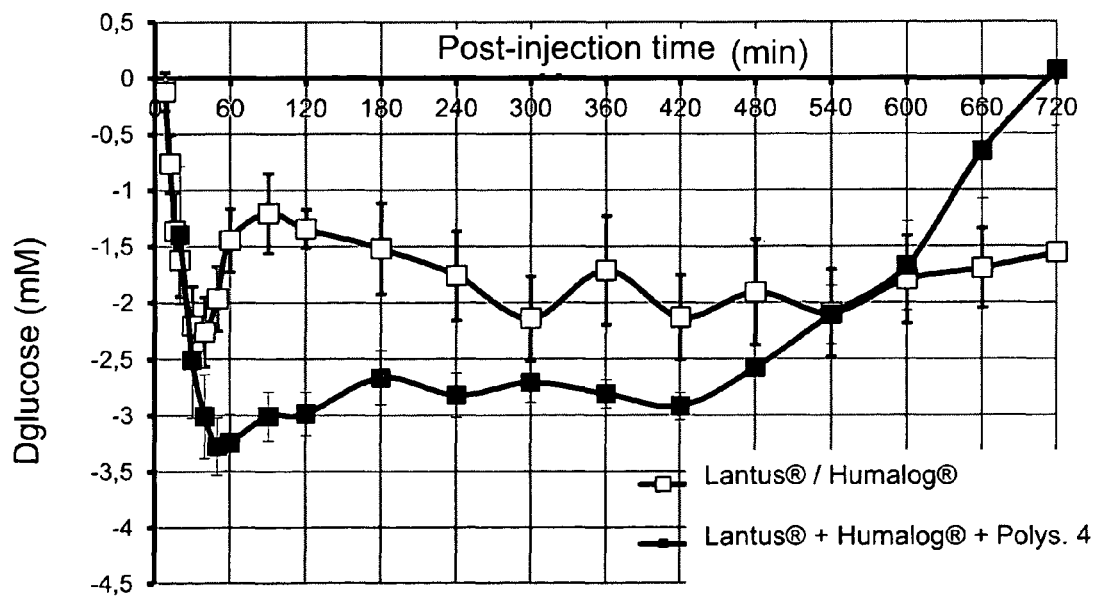

FIG. 4: Mean+standard deviation of the mean curves for the sequential administrations of Humalog® and Lantus® in comparison with the administration of a composition according to the invention Polysaccharide 4/Humalog®/Lantus®.

Figure 5:
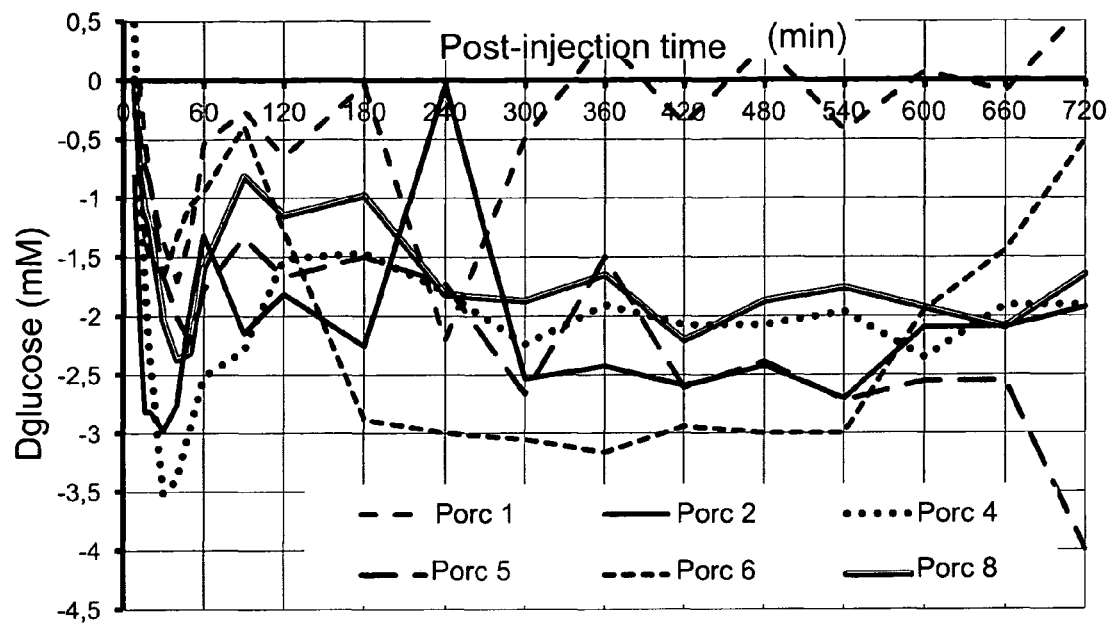

FIG. 5: Humalog® Lantus® individual curves.

Figure 6:
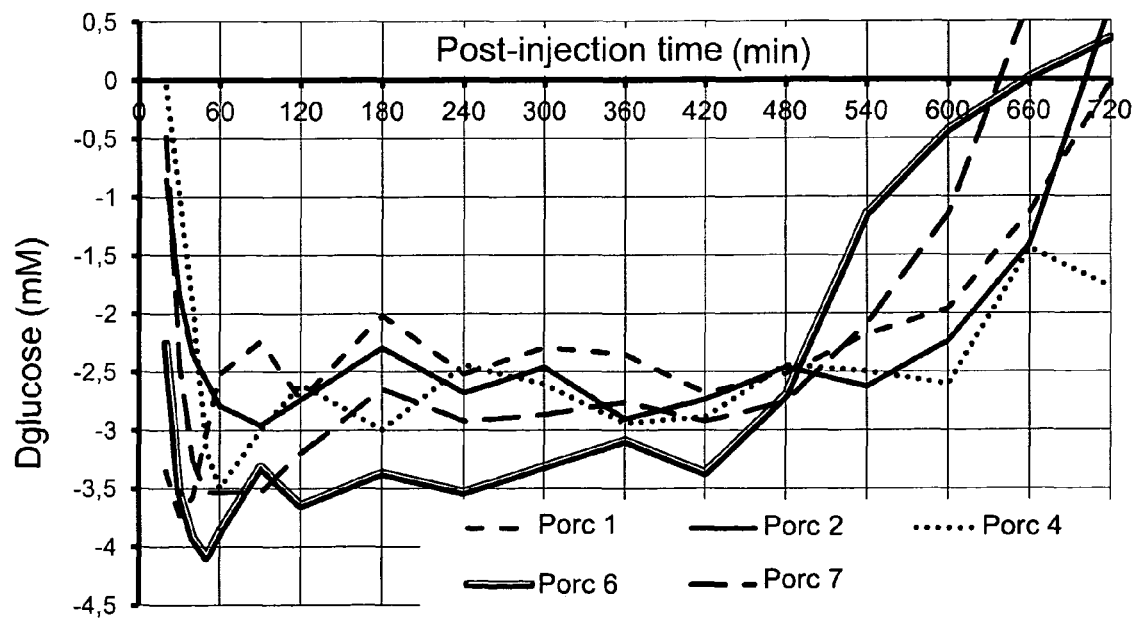

FIG. 6: Polysaccharide 4/Humalog®/Lantus® individual curves.

FIG. 4 presents the mean curves for drop in glycaemia and the standard deviations of the mean for the pigs tested with regard to each formulation. The drop in glycaemia in the first 30 minutes is similar for the two formulations, indicating that the presence of Polysaccharide 4 does not interfere with the rapid-acting nature of Humalog®. On the other hand, between 60 min and 8 h (480 minutes), the sequential administration of Humalog® and Lantus® brings about a heterogeneous drop in glucose with a homogeneous plateau response with regard to four pigs and a heterogeneous response with regard to the other two pigs (FIG. 5). In contrast, the 5 pigs tested with the Polysaccharide 4/Humalog®/Lantus® formulation have a homogeneous response (FIG. 6). This is reflected by the analysis of the coefficients of variation (CV) with regard to the data for drop in glycaemia between 60 min and 8 h, which are on average 54% (between 31% and 72%) for the Humalog® Lantus® control and 15% (between 6% and 28%) for Polysaccharide 4/Humalog®/Lantus®. The presence of Polysaccharide 4 thus greatly reduced the variability of Lantus® with regard to the drop in glycaemia.

Example B38

Protocol for Measuring the Pharmacodynamics of the Insulin Solutions

Preclinical Studies were Carried Out on Dogs for the Purpose of Evaluating Six Compositions According to the Invention:

The hypoglycaemic effects of these compositions were compared with respect to injections carried out with simultaneous but separate injections of 100 IU/ml Lantus® (pH 4) and then of a prandial insulin 100 IU/ml Humalog®.

Ten domesticated dogs (beagles) weighing approximately 12 kg are deprived of food for 18 hours before the beginning of the experiment. In the hour preceding the injection of insulin, three blood samples are taken in order to determine the basal glucose level.

The injection of insulin at a dose of 0.53 IU/kg (unless otherwise mentioned in the examples below) is carried out by subcutaneous injection into the neck of the animal using the Novopen® insulin pen equipped with a 31 G needle.

Blood samples are subsequently taken after 10, 20, 30, 40, 50, 60, 90, 120, 180, 240, 300, 360, 420, 480, 540, 600, 660, 720, 780, 840, 900 and 960 minutes. The first samples are taken with a catheter (up to 180 min) and then directly from the jugular vein. After each sample has been taken, the catheter is rinsed with a dilute heparin solution.

A drop of blood is taken in order to determine the glycaemia by means of a glucose meter. The pharmacodynamic curves for glucose are subsequently plotted.

The results obtained are presented in the form of pharmacodynamic curves for glucose represented in FIGS. 7 to 12.

The Solution of Example B28

Figure 7:
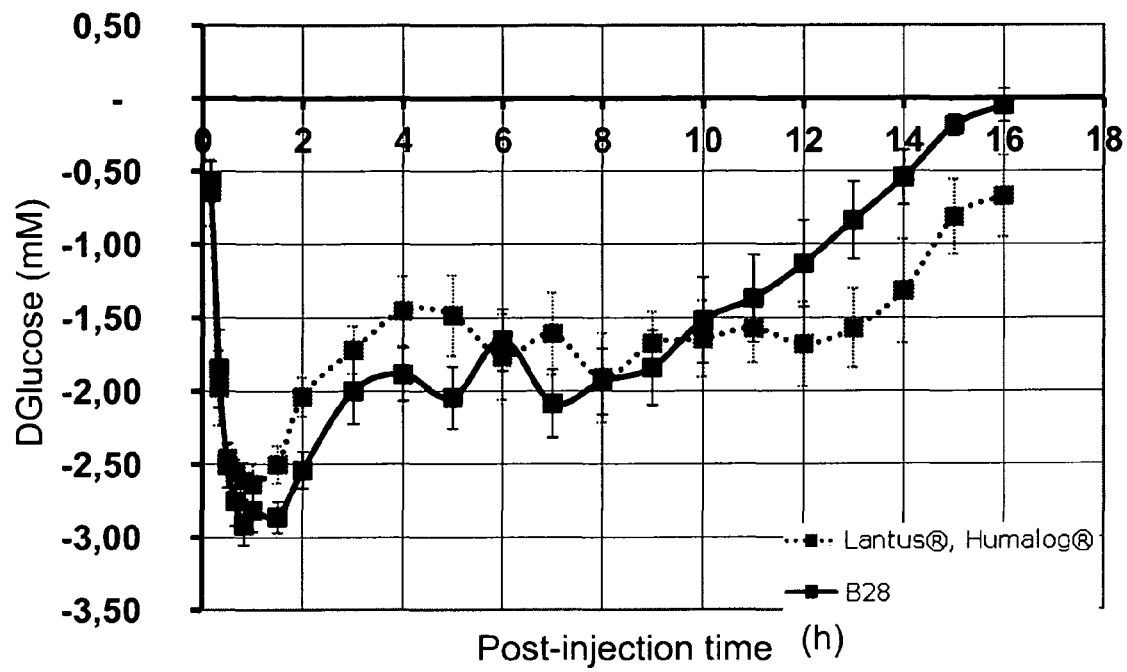
FIGS. 7 to 12 present the results obtained in the form of pharmacodynamic curves for glucose. The axis of the ordinates represents the Dglucose (expressed in mM) as a function of the post-injection time (expressed in hours).

FIG. 7: Mean+standard deviation of the mean curves for the sequential administrations of Humalog® (100 IU/ml, 0.13 IU/kg) and Lantus® (100 IU/ml, 0.4 IU/kg), in comparison with a composition according to the invention described in Example B28 (0.53 IU/kg).

FIG. 7 presents the mean curves for drop in glycaemia and the standard deviations of the mean for the dogs tested for each formulation. The two curves are similar up to 12 hours with a rapid drop in glycaemia, indicating that the polysaccharide does not influence the rapid-acting effect of Humalog®, a marked return between the peak due to Humalog® and the plateau due to glargine, and then a plateau of the glargine up to 12 h, indicating that the basal effect of glargine is well retained.

The Solution of Example B27

Figure 8:
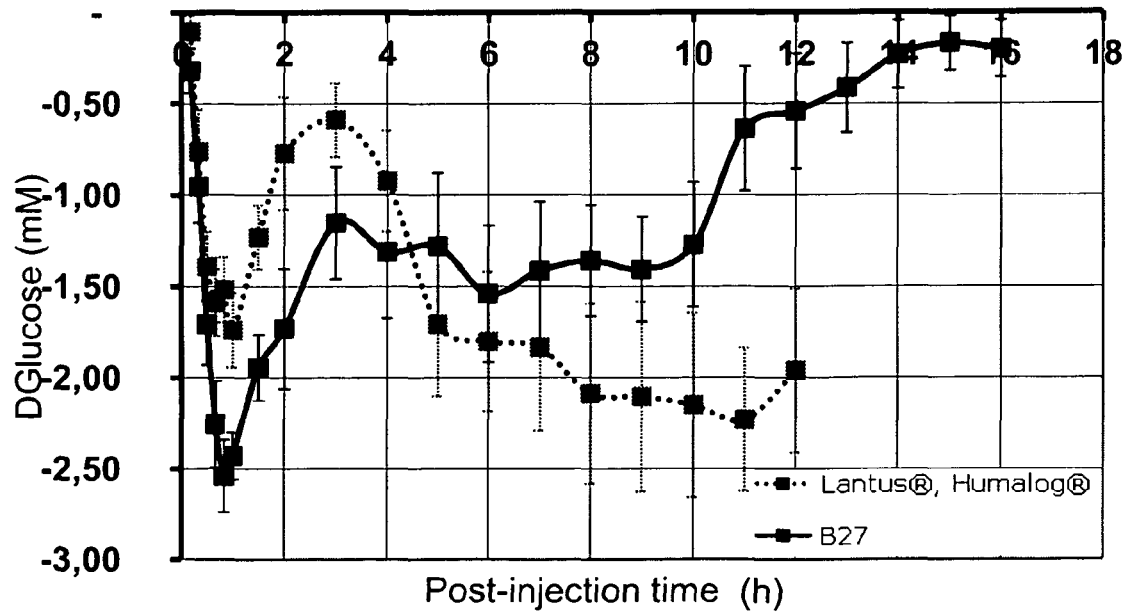

FIG. 8: Mean+standard deviation of the mean curves for the sequential administrations of Humalog® (100 IU/ml, 0.13 IU/kg) and Lantus® (100 IU/ml, 0.4 IU/kg) in comparison with a composition according to the invention described in Example B27 (0.47 IU/kg).

FIG. 8 presents the mean curves for drop in glycaemia and the standard deviations of the mean for the dogs tested for each formulation. In this comparison, the dose of basal insulin (Lantus®) is identical whereas the dose of Humalog® is half for the composition, with respect to the control. The drop in glucose is greater in the case of the formulation B27 in comparison with the control, whereas this control contains twice as much Humalog®. On the other hand, the duration of the plateau is shorter in the case of the combination, with respect to the control. This indicates that, in this composition, a portion of Lantus® is not precipitated on injection and acts with Humalog®.

The Solution of Example B29

Figure 9:
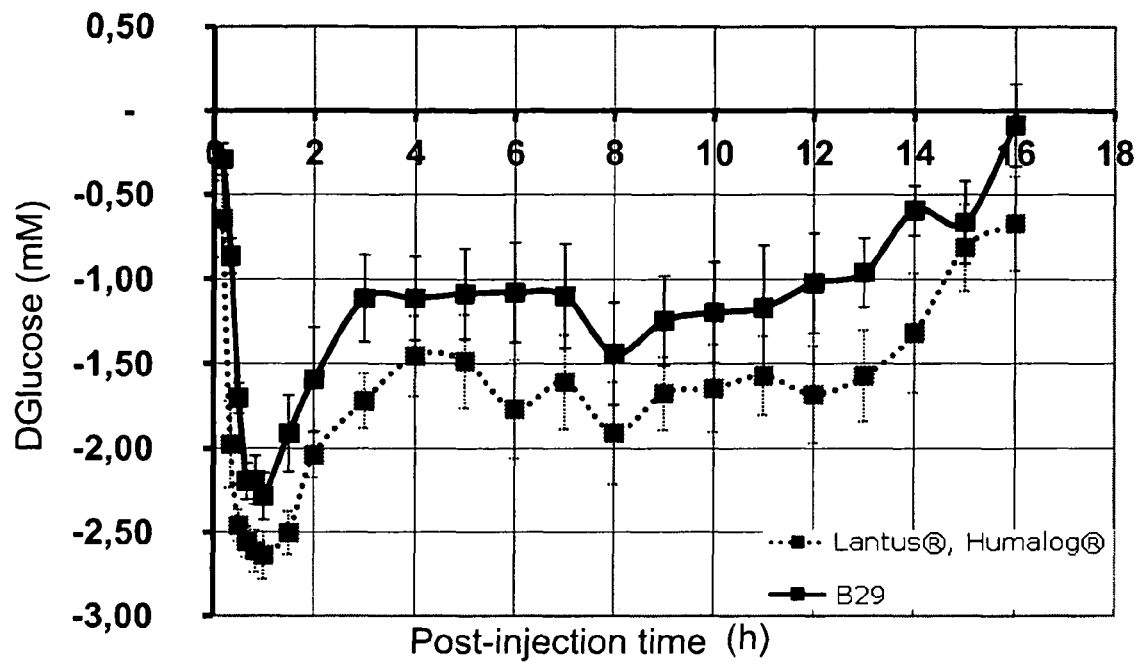

FIG. 9: Mean+standard deviation of the mean curves for the sequential administrations of Humalog® (100 IU/ml, 0.13 IU/kg) and Lantus® (100 IU/ml, 0.4 IU/kg) in comparison with a composition according to the invention described in Example B29 (0.53 IU/kg).

FIG. 9 presents the mean curves for drop in glycaemia and the standard deviations of the mean for the dogs tested for each formulation. The two curves are similar, with a rapid drop in glycaemia, indicating that the polysaccharide does not influence the rapid-acting effect of Humalog®, a marked return between the peak due to Humalog® and the plateau due to Lantus®, and then a plateau of the Lantus® up to 13 h, indicating that the basal effect of glargine is well retained.

The Solution of Example B31

Figure 10:
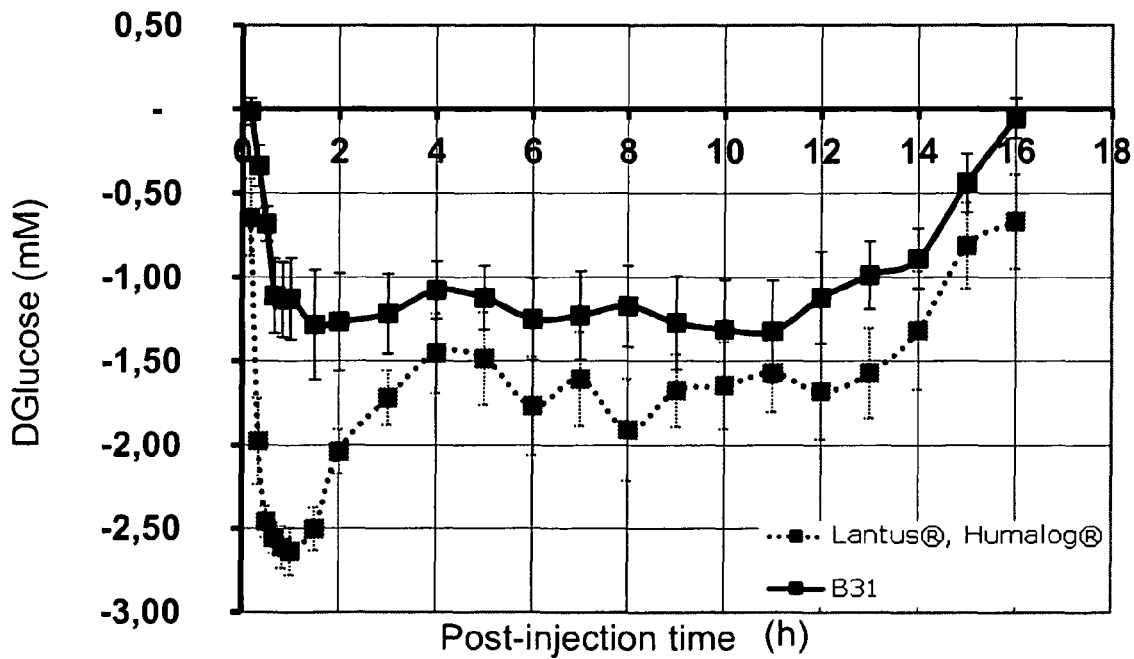

FIG. 10: Mean+standard deviation of the mean curves for the sequential administrations of Humalog® (100 IU/ml, 0.13 IU/kg) and Lantus® (100 IU/ml, 0.4 IU/kg), in comparison with a composition according to the invention described in Example B31 (0.48 IU/kg).

FIG. 10 presents the mean curves for drop in glycaemia and the standard deviations of the mean for the dogs tested for each formulation. In this comparison, the dose of basal insulin (Lantus®) is identical, whereas the dose of Humalog® is half, for the composition, with respect to the control. The drop in glucose is greater in the case of the control, with respect to the combination corresponding to Example B31. This response was expected, in view of the concentration of Humalog® in the combination, which was half that of the control. Furthermore, the duration of the Lantus® plateau is identical in the case of the combination, with respect to the control. This indicates that, in this composition and by comparison with the composition described in Example B29 (FIG. 9), it is possible to adjust the amount of Humalog® in the combination without modifying the Lantus® basal effect.

The Solution of Example B30

Figure 11:
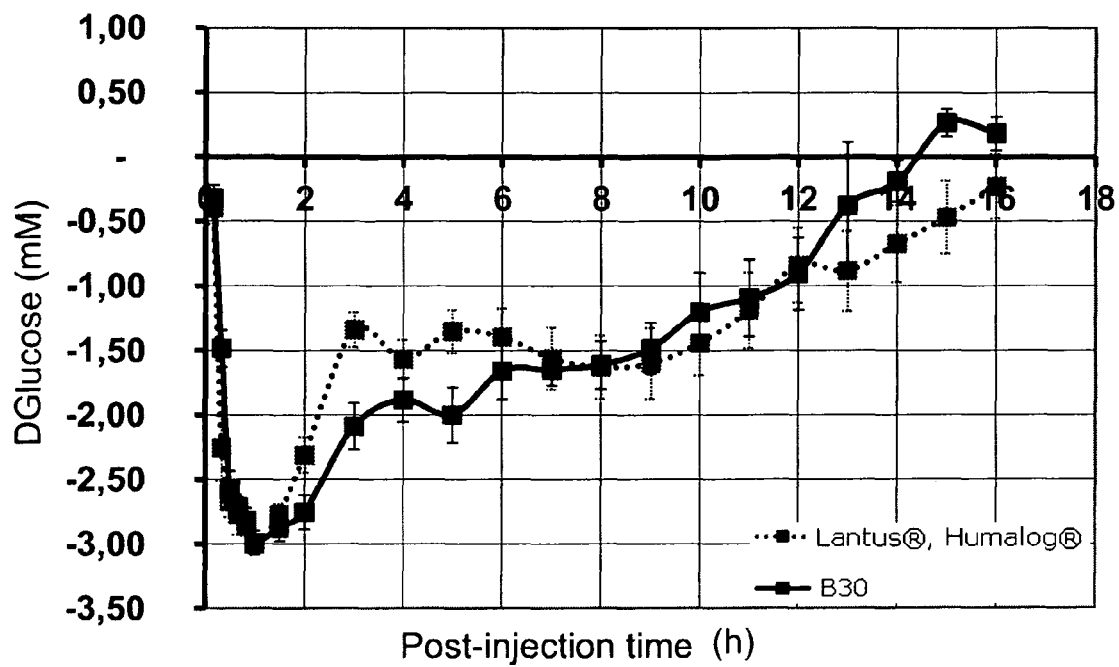

FIG. 11: Mean+standard deviation of the mean curves for the sequential administrations of Humalog® (100 IU/ml, 0.24 IU/kg) and Lantus® (100 IU/ml, 0.4 IU/kg) in comparison with a composition according to the invention described in Example B30 (0.64 IU/kg).

FIG. 11 presents the mean curves for drop in glycaemia and the standard deviations of the mean for the dogs tested for each formulation. The two curves are similar, with a rapid drop in glycaemia, indicating that the polysaccharide does not influence the rapid-acting effect of Humalog®, a marked return between the peak due to Humalog® and the plateau due to Lantus®, and then a plateau of the Lantus® up to 10 h, indicating that the glargine basal effect is well retained.

The Solution of Example B32

Figure 12:
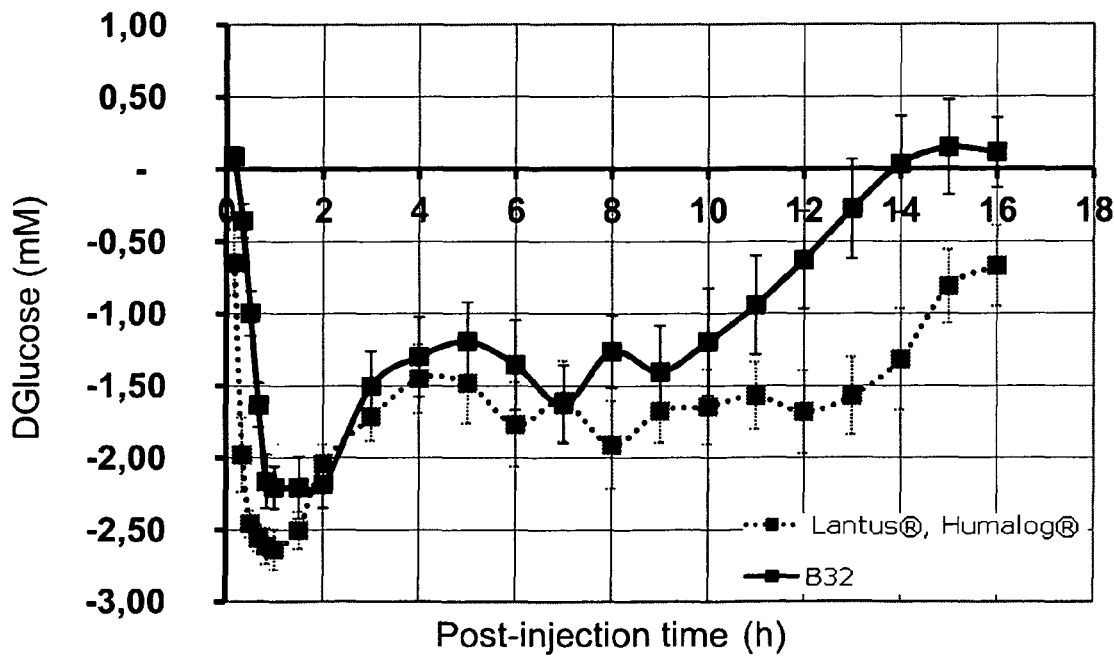

FIG. 12: Mean+standard deviation of the mean curves for the sequential administrations of Humalog® (100 IU/ml, 0.13 IU/kg) and Lantus® (100 IU/ml, 0.4 IU/kg) in comparison with a composition according to the invention described in Example B32 (0.53 IU/kg).

FIG. 12 presents the mean curves for drop in glycaemia and the standard deviations of the mean for the dogs tested for each formulation. The two curves are similar up to 10 hours, with a rapid drop in glycaemia, indicating that the polysaccharide does not influence the rapid-acting effect of Humalog®, a marked return between the peak due to Humalog® and the plateau due to Lantus®, and then a glargine plateau, indicating that the glargine basal effect is retained up to 10 h.

In conclusion, FIGS. 7 to 12 show that, by adjusting the composition of the polysaccharide and the concentrations of lispro and glargine, it is possible to obtain profiles identical to a double injection with different proportions of rapid-acting insulin and basal insulin. It is also possible to adjust the duration of the basal insulin without impacting the rapid-acting insulin or to adjust the amount of rapid-acting insulin without impacting the effect of the basal insulin.

EXAMPLES

Part C

Demonstration of the Properties of the Compositions Comprising a GLP-1 Analogue or Derivative According to the Invention

Example C1

0.25 mg/ml Solution of GLP-1 Analogue Exenatide (Byetta®)

This solution is an exenatide solution marketed by the company Eli Lilly and Company under the name of Byetta®.

Example C2

6 mg/ml Solution of GLP-1 Derivative Liraglutide (Victoza®)

This solution is a liraglutide solution marketed by the company Novo Nordisk under the name of Victoza®.

Example C3

Dissolution of Lantus® at 100 IU/ml and at pH 7 Using a Substituted Dextran at a Concentration of 10 mg/ml 20 mg of a substituted dextran chosen from those described in Table 1 are weighed out accurately. This lyophilisate is taken up in 2 ml of the insulin glargine solution of Example B4 in order to obtain a solution whose polysaccharide concentration is equal to 10 mg/ml. After mechanically stirring on rolls at ambient temperature, the solution becomes clear. The pH of this solution is 6.3. The pH is adjusted to 7 with a 0.1N sodium hydroxide solution. This clear solution is filtered through a membrane (0.22 μm) filter and is then placed at +4° C.

Generalization: Clear solutions of Lantus at 100 IU/ml and at pH 7 were also obtained with concentrations of substituted dextrans at 20 and 40 mg/ml by following the same protocol as that described in Example C3. Thus, a weight of lyophilized polysaccharide among those described in Table 1 is weighed out accurately. This lyophilisate is taken up in the insulin glargine solution of Example B4, so as to obtain a solution whose concentration of substituted dextran is 20 or 40 mg/ml, as described in Table 8. After mechanical stirring on rolls at ambient temperature, the solution becomes clear. The pH of this solution is less than 7. The pH is subsequently adjusted to 7 with a 0.1N sodium hydroxide solution. This clear final solution is filtered through a membrane (0.22 μm) and is then placed at +4° C.

TABLE 8

Preparation of a solution of Lantus ® at 100 IU/ml and at pH 7 using a substituted dextran at a concentration of 10, 20 or 40 mg/ml

| Final concentration of substituted dextran (mg/ml) | Weight of substituted dextran weighed out (mg) | Volume of the insulin glargine solution of Example B4 added (ml) |
|---|---|---|
| 10 | 20 | 2 |
| 20 | 40 | 2 |
| 40 | 80 | 2 |

Example C4

Preparation of a Lantus®/Byetta® 70/30 Composition at pH 7.5

0.09 ml of the exenatide solution of Example C1 is added to 0.21 ml of the insulin glargine solution of Example B4, in order to obtain 0.3 ml of composition whose pH is 4.5 on mixing. The composition, which contains 70 IU/ml of Lantus® and 0.075 mg/ml of Byetta®, is clear, testifying to the good solubility of Lantus® and Byetta® under these formulation conditions (pH 4.5). The pH is subsequently adjusted to 7.5 with a 0.1N sodium hydroxide solution. The composition then becomes cloudy, testifying to the poor solubility of the Lantus®/Byetta® composition at pH 7.5.

70/30 Lantus®/Byetta® compositions were also prepared at pH 4.5, 5.5, 6.5, 8.5 and 9.5 by following a protocol similar to that described in Example C4. For each of these compositions, 0.09 ml of the exenatide solution of Example C1 is added to 0.21 ml of the insulin glargine solution of Example B4, in order to obtain 0.3 ml of a composition whose pH is 4.5 on mixing. The composition is clear, testifying to the good solubility of Lantus® and Byetta® under these formulation conditions (pH 4.5). The pH is adjusted to 5.5 or 6.5 or 8.5 or 9.5 with a 0.1N sodium hydroxide solution. After adjusting the pH, the composition at 5.5 is slightly cloudy, the compositions at 6.5-7.5 and 8.5 are very cloudy and the composition at pH 9.5 is clear. These compositions are placed at +4° C. for 48 h. After 48 h at +4° C., only the composition at pH 4.5 remains clear. The visual appearance after 48 h of the 70/30 Lantus®/Byetta® compositions at different pH values is summarized in Table 9.

TABLE 9

Visual appearance after 48 h of the 70/30 Lantus ®/Byetta ® compositions at different pH values
70/30 Lantus ®/Byetta ® compositions at different pH values

| pH | Visual appearance at t = 48 h |
|---|---|
| 4.5 | Clear |
| 5.5 | Presence of a precipitate |
| 6.5 | Presence of a precipitate |
| 7.5 | Presence of a precipitate |
| 8.5 | Presence of a precipitate |
| 9.5 | Presence of a precipitate |

Example C5

Preparation of the 70/30 Lantus®/Victoza® Composition at pH 7.5

0.09 ml of the liraglutide solution of Example C2 is added to 0.21 ml of the insulin glargine solution of Example B4, in order to obtain 0.3 ml of a composition whose pH is 7 on mixing. The composition, which contains 70 IU/ml of glargine and 1.8 mg/ml of liraglutide, is cloudy, testifying to the poor solubility of the Lantus®/Victoza® composition under these formulation conditions. The pH is adjusted to 7.5 with a 0.1N sodium hydroxide solution. After adjusting the pH, the composition remains cloudy. This composition is placed at +4° C. for 48 h.

70/30 Lantus®/Victoza® compositions were also prepared at pH 4.5-5.5-6.5-8.5 and 9.5 by following a protocol similar to that described in Example C5. For each of these compositions, 0.09 ml of the liraglutide solution of Example C1 is added to 0.21 ml of the insulin glargine solution of Example B4, in order to obtain 0.3 ml of a composition whose pH is 7. The composition is cloudy, testifying to the poor solubility of the Lantus®/Victoza® composition under these formulation conditions (pH 7). The pH is adjusted to 4.5 or 5.5 or 6.5 with a 0.1N hydrochloric acid solution or to pH 9.5 with a 0.1N sodium hydroxide solution. After adjusting the pH, the compositions at pH 4.5-5.5 and 6.5 are cloudy, testifying to the poor solubility of the Lantus®/Victoza® composition under these formulation conditions. These compositions are placed at +4° C. for 48 h. After 48 h at 4° C., only the composition at pH 9.5 is clear. The visual appearance after 48 h of the 70/30 Lantus®/Victoza® compositions of different pH values is summarized in Table 10.

TABLE 10

Visual appearance after 48 h of the 70/30 Lantus ®/Victoza ® compositions at different pH values
70/30 Lantus ®/Victoza ® compositions at different pH values

| pH | Visual appearance at t = 48 h |
|---|---|
| 4.5 | Presence of a precipitate |
| 5.5 | Presence of a precipitate |
| 6.5 | Presence of a precipitate |
| 7.5 | Presence of a precipitate |
| 8.5 | Presence of a precipitate |
| 9.5 | Clear |

Example C6

Preparation of a Substituted Dextran-70/30 Lantus®/Byetta® Composition at pH 7

0.09 ml of the exenatide solution of Example C1 is added to 0.21 ml of the substituted dextran/Lantus® solution prepared in Example C3, in order to obtain 0.3 ml of a composition at pH 5.3. The pH is adjusted to 7 with a 0.1N sodium hydroxide solution. The composition, which contains 7 mg/ml of polysaccharide, 70 IU/ml of Lantus® and 0.075 mg/ml of Byetta® is clear, testifying to the good solubility of Lantus® and Byetta® in the presence of the substituted dextran at pH 7. This clear solution is placed at +4° C.

Generalization: Substituted dextran-Lantus®/Byetta® compositions at pH 7 were also prepared at ratios by volume $V_{Lantus}/V_{Byetta}$ of 90/10, 50/50, 30/70 and 10/90 by following the same protocol as that described in Example C6. Thus, a volume $V_{Byetta}$ of the exenatide solution of Example C1 is added to a volume $V_{Lantus}$ of the substituted dextran/Lantus® solution prepared in Example C3, in order to obtain a composition whose pH is adjusted to 7 with a 0.1N sodium hydroxide solution. The compositions obtained (see Table 11) are clear, testifying to the good solubility of Lantus® and Byetta® in the presence of a substituted dextran at pH 7. These clear solutions are placed at +4° C.

Example C7

Preparation of a Substituted Dextran-100/50 Lantus®/Byetta® Composition at pH 7

0.150 ml of the exenatide solution of Example C1 is lyophilized and then 0.3 ml of a substituted dextran/Lantus® solution prepared in Example C3 are added to the lyophilisate in order to obtain a composition whose pH is adjusted to 7 with a 0.1N sodium hydroxide solution. The composition, which contains 10 mg/ml of polysaccharide, 100 IU/ml of Lantus® and 0.125 mg/ml of Byetta®, is clear, testifying to the good solubility of Lantus® and Byetta® in the presence of the substituted dextran at pH 7. This clear solution is placed at +4° C.

TABLE 11

Final concentrations of Lantus ®, substituted dextran and Byetta ® of the compositions obtained in Examples C6 and C7

| Lantus ® | | [Polysaccharide No.] | Byetta ® |
|---|---|---|---|
| IU/ml | mg/ml | (mg/ml) | (mg/ml) |
| 100/50 | 100 | 3.5 | 10 | 0.125 |
| 90/10 | 90 | 3.15 | 9 | 0.025 |
| 70/30 | 70 | 2.45 | 7 | 0.075 |
| 50/50 | 50 | 1.75 | 5 | 0.125 |
| 30/70 | 30 | 1.05 | 3 | 0.175 |

Example C8

Preparation of a Substituted Dextran-70/30 Lantus®/Victoza® Composition at pH 7

0.09 ml of the liraglutide solution of Example C2 is added to 0.21 ml of the substituted dextran/Lantus® solution prepared in Example C3, in order to obtain 0.3 ml of a composition at pH 7.6. The pH is adjusted to 7 with a 0.1N hydrochloric acid solution. The composition, which contains 7 mg/ml of polysaccharide, 70 IU/ml of Lantus® and 1.8 mg/ml of Victoza®, is clear, testifying to the good solubility of Lantus® and Victoza® in the presence of the substituted dextran at pH 7. This clear solution is placed at +4° C.

Generalization: Substituted dextran-Lantus®/Victoza® compositions at pH 7 have also been prepared at $V_{Lantus}/V_{Victoza}$ ratios by volume of 90/10, 50/50, 30/70, and 90/10 by following the same protocol as that described in Example C6. Thus, a volume $V_{Victoza}$ of the liraglutide solution of Example C2 is added to a volume $V_{Lantus}$ of the substituted dextran/Lantus® solution prepared in Example B3, in order to obtain a composition whose pH is adjusted to 7 with a 0.1N hydrochloric acid solution.

The compositions obtained (see Table 12) are clear, testifying to the good solubility of Lantus® and Victoza® in the presence of a substituted dextran at pH 7. These clear solutions are placed at +4° C.

Example C9

Preparation of a Substituted Dextran-100/50 Lantus®/Victoza® Composition at pH 7

0.150 ml of the liraglutide solution of Example C2 is lyophilized and then 0.3 ml of a substituted dextran/Lantus® solution prepared in Example C3 is added to the lyophilisate, in order to obtain a composition whose pH is adjusted to 7 with a 0.1N sodium hydroxide solution. The composition, which contains 10 mg/ml of polysaccharide, 100 IU/ml of Lantus® and 3 mg/ml of Victoza®, is clear, testifying to the good solubility of Lantus® and Victoza® in the presence of the substituted dextran at pH 7. This clear solution is placed at +4° C.

TABLE 12

Final concentrations of Lantus ®, substituted dextran and Victoza ® of the compositions obtained in Examples C8 and C9

| | Lantus ® | | [Polysaccharide No.] | |
|---|---|---|---|---|
| | IU/ml | mg/ml | (mg/ml) | Victoza ® (mg/ml) |
| 100/50 | 100 | 3.5 | 10 | 3 |
| 90/10 | 90 | 3.15 | 9 | 0.6 |
| 70/30 | 70 | 2.45 | 7 | 1.8 |
| 50/50 | 50 | 1.75 | 5 | 3 |
| 30/70 | 30 | 1.05 | 3 | 4.2 |

Example C10

Preparation of a Substituted Dextran-60/20/20 Lantus®/Apidra®/Byetta® Composition at pH 7

20 mg of lyophilized Polysaccharide 4 described in Example A3 are weighed out accurately. This lyophilisate is taken up in 2 ml of the insulin glargine solution of Example B4. After mechanical stirring on rolls at ambient temperature, the solution becomes clear. The pH of this solution is 6.3. The pH is adjusted to 7 with a 0.1N sodium hydroxide solution. 0.2 ml of the exenatide solution of Example C1 and 0.2 ml of the insulin glulisine solution of Example B3 are added to 0.6 ml of the substituted dextran/Lantus® solution prepared above, in order to obtain 1 ml of a composition at pH 7. The composition, which contains 6 mg/ml of polysaccharide, 60 IU/ml of Lantus®, 20 IU/ml Apidra® and 0.05 mg/ml of Byetta®, is clear, testifying to the good solubility of Lantus®, Apidra® and Byetta® in the presence of substituted dextran at pH 7. This clear solution is filtered through a membrane (0.22 μm) and is then placed at +4° C.

Example C11

Precipitation of Lantus®

0.250 ml of Lantus® is added to 0.5 ml of a PBS (Phosphate Buffer Solution) solution containing 20 mg/ml of BSA (Bovine Serum Albumin). The PBS/BSA mixture simulates the composition of the subcutaneous medium.

A precipitate appears, which is in good agreement with the mechanism of operation of Lantus® (precipitation on injection due to the increase in the pH).

Centrifuging at 4000 rev/min is carried out in order to separate the precipitate from the supernatant. Subsequently, Lantus® is assayed in the supernatent. The result of this is that 90% of Lantus® is found in a precipitated form.

Example C12

Precipitation of a Substituted Dextran/Lantus® Composition 0.250 ml of substituted dextran/Lantus® solution prepared in Example C3 is added to 0.5 ml of a PBS solution containing 20 mg/ml of BSA. The PBS/BSA mixture simulates the composition of the subcutaneous medium. A precipitate appears.

Centrifuging at 4000 rev/min is carried out in order to separate the precipitate from the supernatent. Subsequently, Lantus® is assayed in the supernatent. The result of this is that 90% of Lantus® is found in a precipitated form. This percentage of precipitation of Lantus® is identical to that obtained for the control described in Example C11.

Example C13

Precipitation of a Substituted Dextran-Lantus®/Byetta® Composition 0.250 ml of the substituted dextran-Lantus®/Byetta® composition prepared in Example C6 is added to 0.5 ml of a PBS solution containing 20 mg/ml of BSA. The PBS/BSA mixture simulates the composition of the subcutaneous medium. A precipitate appears.

Centrifuging at 4000 rev/min is carried out in order to separate the precipitate from the supernatent. Subsequently, Lantus® and Byetta® are assayed in the supernatent. The percentage of precipitation of Lantus® is similar to the control described in Example C11.

Example C14

Precipitation of a Substituted Dextran-70/30 Lantus®/Victoza® Composition 0.250 ml of the substituted dextran-Lantus®/Victoza® composition prepared in Example C8 is added to 0.5 ml of a PBS solution containing 20 mg/ml of BSA (bovine serum albumin). The PBS/BSA mixture simulates the composition of the subcutaneous medium. A precipitate appears.

Centrifuging at 4000 rev/min is carried out in order to separate the precipitate from the supernatent. Subsequently, Lantus® and Victoza® are assayed in the supernatent. The percentage of precipitation of Lantus® is similar to the control described in Example C11.

Example C15

Precipitation of Different Compositions, the Nature of the Substituted Dextran being Varied Other tests under the same conditions as those of Examples C13 and C14 were carried out in the presence of other dextrans.

Results with at most 20 mg/ml of substituted dextran and a 70/30 Lantus®/Byetta® composition are combined in the following Table 13. It is observed that the dissolution and the precipitation of Lantus® are retained.

TABLE 13

Results of the dissolution and precipitation tests obtained with at most 20 mg/ml of substituted dextran and a 70/30 Lantus ®/Byetta ® composition

| Polysaccharide No. | Dissolution 70/30 Lantus ®/Byetta ® | Percentage of precipitation of Lantus ® |
|---|---|---|
| 1 | Yes | 94 |
| 2 | Yes | 96 |
| 5 | Yes | 88 |
| 7 | Yes | 95 |
| 10 | Yes | Not measured |
| 11 | Yes | 81 |
| 14 | Yes | Not measured |
| 16 | Yes | 96 |
| 26 | Yes | 81 |
| 27 | Yes | 96 |
| 28 | Yes | 96 |
| 29 | Yes | 95 |

Results with at most 20 mg/ml of substituted dextran and various Lantus®/Byetta® compositions are combined in the following Table 14. It is observed that the dissolution and the precipitation of Lantus® are retained.

TABLE 14

Results of the dissolution and precipitation tests obtained with at most 20 mg/ml of substituted dextran and various Lantus ®/Byetta ® compositions

| Polysaccharide No. | Ratio Lantus ®/Byetta ® | Dissolution Lantus ®/Byetta ® | Percentage of precipitation of Lantus ® |
|---|---|---|---|
| 4 | 100/50 | Yes | 95 |
| 4 | 90/10 | Yes | 94 |
| 4 | 70/30 | Yes | 95 |
| 4 | 50/50 | Yes | 90 |
| 4 | 30/70 | Yes | 82 |
| 8 | 100/50 | Yes | 96 |
| 8 | 90/10 | Yes | 94 |
| 8 | 70/30 | Yes | 96 |
| 8 | 50/50 | Yes | 90 |
| 8 | 30/70 | Yes | 81 |

Results with at most 40 mg/ml of substituted dextran and a 70/30 Lantus®/Victoza® composition are combined in the following Table 15. It is observed that the dissolution and the precipitation of Lantus® are retained.

TABLE 15

Results of the dissolution and precipitation tests obtained with at most 40 mg/ml of substituted dextran and a 70/30 Lantus ®/Victoza ® composition

| Polysaccharide No. | Dissolution 70/30 Lantus ®/Victoza ® | Percentage of precipitation of Lantus ® |
|---|---|---|
| 1 | Yes | 95 |
| 2 | Yes | 97 |
| 5 | Yes | Not measured |
| 7 | Yes | 97 |
| 10 | Yes | Not measured |
| 11 | Yes | Not measured |
| 14 | Yes | 90 |
| 16 | Yes | 97 |
| 26 | Yes | 74 |
| 27 | Yes | 96 |
| 28 | Yes | 95 |
| 29 | Yes | 94 |

Results with at most 20 mg/ml of substituted dextran and various Lantus®/Victoza® compositions are combined in the following Table 16. It is observed that the dissolution and the precipitation of Lantus® are retained.

TABLE 16

Results of the dissolution and precipitation tests obtained with at most 20 mg/ml of substituted dextran and various Lantus ®/Victoza ® compositions

| Polysaccharide No. | Ratio Lantus ®/Victoza ® | Dissolution Lantus ®/Victoza ® | Percentage of precipitation of Lantus ® |
|---|---|---|---|
| 4 | 90/10 | Yes | 94 |
| 4 | 70/30 | Yes | Not measured |
| 4 | 50/50 | Yes | 90 |
| 4 | 30/70 | Yes | 86 |
| 8 | 100/50 | Yes | 93 |
| 8 | 90/10 | Yes | 95 |
| 8 | 70/30 | Yes | 98 |
| 8 | 50/50 | Yes | 89 |
| 8 | 30/70 | Yes | 85 |

Example C16

Precipitation of a Substituted Dextran-60/20/20 Lantus®/Apidra®/Byetta® Composition at pH 7

0.250 ml of the substituted dextran-Lantus®/Apidra®/Byetta® composition prepared in Example C10 is added to 0.5 ml of a PBS solution containing 20 mg/ml of BSA. The PBS/BSA mixture simulates the composition of the subcutaneous medium. A precipitate appears.

Centrifuging at 4000 rev/min is carried out in order to separate the precipitate from the supernatent. Subsequently, Lantus® is assayed in the supernatent. The percentage of precipitation of Lantus® is similar to the control described in Example C11.

The invention claimed is:

1. A composition in the form of an injectable aqueous solution, the pH of which is between 6.0 and 8.0, comprising at least:
   a) a basal insulin, the isoelectric point pI of which is between 5.8 and 8.5;
   b) dextran polymers substituted by radicals carrying carboxylate charges and hydrophobic radicals of formula I or of formula II:

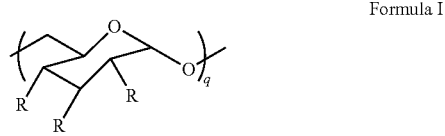

Formula I in which:
   R is —OH or is chosen from the group consisting of the radicals:
      -(f-[A]-COOH)$_n$; and
      -(g-[B]-k-[D])$_m$, D comprising at least one alkyl chain comprising at least 8 carbon atoms;
   n represents the degree of substitution of the glucoside units of the dextran polymers by -f-[A]-COOH, and 0.1≤n≤2;
   m represents the degree of substitution of the glucoside units of the dextran polymers by -g-[B]-k-[D], and 0<m≤0.5;
   q represents the degree of polymerization measured as the mean number of glucoside units per polysaccharide chain of the dextran polymers, and 3≤q≤50;
   wherein for -(f-[A]-COOH)$_n$:
      -A- is a linear or branched radical comprising from 1 to 4 carbon atoms; the -A- radical:
      being bonded to a glucoside unit via a functional group f chosen from the group consisting of ether, ester and carbamate functional groups;
   wherein for -(g-[B]-k-[D])$_m$:
      —B— is a linear or branched, at least divalent, radical comprising from 1 to 4 carbon atoms; the —B— radical:
      being bonded to a glucoside unit via a functional group g chosen from the group consisting of ether, ester and carbamate functional groups;
      being bonded to a -D radical via a functional group k; k chosen from the group consisting of ester, amide and carbamate functional groups; the -D radical:
      being an —X(-l-Y)$_p$ radical, X being an at least divalent radical comprising from 1 to 12 atoms chosen from the group consisting of C, N and O atoms, optionally carrying carboxyl or amine functional groups and/or resulting from an amino acid, a dialcohol, a diamine or a mono- or polyethylene glycol mono- or diamine; Y being a linear or cyclic alkyl group, an alkylaryl or an arylalkyl, of 8 to 30 carbon atoms, optionally substituted by one or more $C_1$ to $C_3$ alkyl groups; p≥1 and l a functional group chosen from the group consisting of ester, amide and carbamate functional groups;

f, g and k being identical or different;

free acid functional groups being in the form of salts of alkali metal cations chosen from the group consisting of $Na^+$ and $K^+$;

and, when p=1, if Y is a $C_8$ to $C_{14}$ alkyl, then q*m≤2, if Y is a $C_{15}$ alkyl, then q*m≥2; and if Y is a $C_{16}$ to $C_{20}$ alkyl, then q*m≥1;

and, when p≥2, if Y is a $C_8$ to $C_9$ alkyl, then q*m≥2 and, if Y is a $C_{10}$ to $C_{16}$ alkyl, then q*m≥0.2;

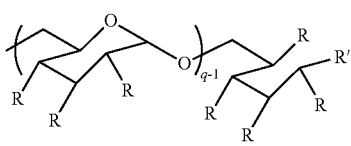

Formula II in which:

R is —OH or is a -(f-[A]-COOH)$_n$ radical:
 -A- is a linear or branched radical comprising from 1 to 4 carbon atoms; the radical -A-:
 being bonded to a glucoside unit via a functional group f chosen from the group consisting of ether, ester and carbamate functional groups;
 n represents the degree of substitution of the glucoside units of the dextran polymers by -f-[A]-COOH and is 0.1<n<2;

R' is chosen from the group consisting of the radicals:
 —C(O)NH-[E]-(o-[F])$_t$; and
 —CH$_2$N(L)$_z$-[E]-(o-[F])$_t$;

in which:
 z is a positive integer equal to 1 or 2,
 L is chosen from the group consisting of:
  —H and z is equal to 1, and/or
  -[A]-COOH and z is equal to 1 or 2, if f is an ether functional group,
  —CO-[A]-COOH and z is equal to 1 if f is an ester functional group, and
  —CO—NH-[A]-COOH and z is equal to 1 if f is a carbamate functional group;
 wherein for -[E]-(o-[F])$_t$:
  -E- is a linear or branched, at least divalent, radical comprising from 1 to 8 carbon atoms and optionally comprising heteroatoms;
  —F— is a linear or cyclic alkyl group, an alkylaryl or an arylalkyl, of 12 to 30 carbon atoms, optionally substituted by one or more $C_1$ to $C_3$ alkyl groups;
  o is a functional group chosen from the group consisting of ether, ester, amide and carbamate functional groups;
  t is a positive integer equal to 1 or 2;
 q represents the degree of polymerization measured as the mean number of glucoside units per polysaccharide chain of the dextran polymers, and 3≥q≥50;

free acid functional groups being in the form of salts of alkali metal cations chosen from the group consisting of $Na^+$ and $K^+$; and when z=2, the nitrogen atom is in the form of a quaternary ammonium;

c) a prandial insulin; and d) a zinc salt;

wherein the basal insulin is soluble in the injectable aqueous solution and precipitates by at least 85 percent in subcutaneous medium, and the basal insulin exhibits its biological activity and a basal insulin action profile following injection of the injectable aqueous solution.

2. The composition according to claim 1, wherein the dextran polymers substituted by radicals carrying carboxylate charges and hydrophobic radicals are dextran polymers of formula I.

3. The composition according to claim 1, wherein the dextran polymers substituted by radicals carrying carboxylate charges and hydrophobic radicals are dextran polymers of formula II.

4. The composition according to claim 1, wherein the dextran polymers substituted by radicals carrying carboxylate charges and hydrophobic radicals are dextran polymers of formula I in which the -(f-[A]-COON)$_n$ radical is chosen from the group consisting of the following sequences, f having the meaning given above:

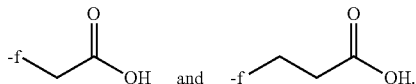

5. The composition according to claim 1, wherein the dextran polymers substituted by radicals carrying carboxylate charges and hydrophobic radicals are dextran polymers of formula I in which the -(g-[B]-k-[D])$_m$ radical is chosen from the group consisting of the following sequences, g, k and D having the meanings given above:

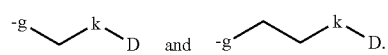

6. The composition according to claim 1, wherein the dextran polymers substituted by radicals carrying carboxylate charges and hydrophobic radicals are dextran polymers formula I in which the -(g-[B]-k-[D])$_m$ radical is such that:
 —B— is a radical comprising one carbon atom; the —B— radical being bonded to a glucoside unit via an ether functional group g, and X is a radical resulting from an amino acid.

7. The composition according to claim 1, wherein the dextran polymers substituted by radicals carrying carboxylate charges and hydrophobic radicals are dextran polymers of formula I in which the X radical is an at least divalent radical resulting from an amino acid chosen from the group consisting of glycine, phenylalanine, lysine, isoleucine, alanine, valine, aspartic acid and glutamic acid.

8. The composition according to claim 1, wherein the dextran polymers substituted by radicals carrying carboxylate charges and hydrophobic radicals are dextran polymers of formula I in which the Y group is chosen from the group consisting of a hydrophobic alcohol, a hydrophobic acid, a sterol and a tocopherol.

9. The composition according to claim 1, wherein the dextran polymers substituted by radicals carrying carboxylate charges and hydrophobic radicals are dextran polymers of formula I in which the Y group is a sterol chosen from cholesterol derivatives.

10. The composition according to claim 1, wherein the dextran polymers substituted by radicals carrying carboxylate charges and hydrophobic radicals are dextran polymers of formula II in which the R' group is such that the -E- radical results from a diamine.

11. The composition according to claim 1, wherein the dextran polymers substituted by radicals carrying carboxylate charges and hydrophobic radicals are dextran polymers of formula II in which the R' group is such that the —F— group results from a cholesterol derivative.

12. The composition according to claim 1, wherein the dextran polymers substituted by radicals carrying carboxylate charges and hydrophobic radicals are one or more of the following dextran polymers of formula I:
Sodium dextranmethylcarboxylate modified by octyl glycinate,
Sodium dextranmethylcarboxylate modified by cetyl glycinate,
Sodium dextranmethylcarboxylate modified by octyl phenylalaninate,
Sodium dextranmethylcarboxylate modified by 3,7-dimethyl-1-octyl phenylalaninate,
Sodium dextranmethylcarboxylate modified by dioctyl aspartate,
Sodium dextranmethylcarboxylate modified by didecyl aspartate,
Sodium dextranmethylcarboxylate modified by dilauryl aspartate,
Sodium dextranmethylcarboxylate modified by N-(2-aminoethyl)dodecanamide,
Sodium dextransuccinate modified by lauryl glycinate,
N-(sodium methylcarboxylate) dextran carbamate modified by dioctyl aspartate,
Sodium dextranmethylcarboxylate modified by 2-(2-aminoethoxy)ethyl dodecanoate,
Sodium dextranmethylcarboxylate modified by 2-(2-{2-[dodecanoylamino]ethoxy}ethoxy)ethylamine,
Sodium dextranmethylcarboxylate modified by 2-(2-{2-[hexadecanoylamino]ethoxy}ethoxy)ethylamine,
Sodium dextranmethylcarboxylate modified by cholesteryl leucinate,
Sodium dextranmethylcarboxylate modified by cholesteryl 1-ethylenediaminecarboxylate,
N-(sodium methylcarboxylate) dextran carbamate modified by cholesteryl leucinate.

13. The composition according to claim 1, wherein the dextran polymers substituted by radicals carrying carboxylate charges and hydrophobic radicals are dextran polymers of formula II and are:
Sodium dextranmethylcarboxylate modified by cholesteryl 1-ethylenediaminecarboxylate grafted by reductive amination to the reducing chain end.

14. The composition according to claim 1, wherein the basal insulin whose isoelectric point is between 5.8 and 8.5 is insulin glargine.

15. The composition according to claim 1, wherein the composition comprises from 40 IU/ml to 500 IU/ml of basal insulin whose isoelectric point is between 5.8 and 8.5.

16. The composition according to claim 1, wherein the composition comprises from 40 to 800 IU/ml of total insulin.

17. The composition according to claim 1, wherein the composition comprises proportions, expressed as percentage, between the basal insulin whose isoelectric point is between 5.8 and 8.5 and the prandial insulin of 25/75, 30/70, 40/60, 50/50, 60/40, 70/30, 80/20 or 90/10.

18. The composition according to claim 1, wherein the composition additionally comprises a GLP-1, a GLP-1 analogue or a GLP-1 derivative.

19. The composition according to claim 1, wherein the composition additionally comprises zinc salts at a concentration of between 0 and 5000 µM.

20. The composition according to claim 1, wherein the composition comprises buffers chosen from the group consisting of Tris, citrates and phosphates at concentrations of between 0 and 100 mM.

21. The composition according to claim 1, wherein the prandial insulin is chosen from the group formed by human insulin, insulin glulisine, insulin lispro and insulin aspart.

22. Single-dose formulation comprising a composition according to claim 1, at a pH of between 6.6 and 7.8.

23. Single-dose formulation comprising a composition according to claim 1, at a pH of between 6.6 and 7.8, and a GLP-1, a GLP-1 derivative or a GLP-1 analogue.

24. Single-dose formulation according to claim 22, wherein the prandial insulin is human insulin.

25. Single-dose formulation according to claim 22, wherein the prandial insulin is chosen from the group consisting of insulin lispro, insulin glulisine and insulin aspart.

* * * * *

UNITED STATES PATENT AND TRADEMARK OFFICE
CERTIFICATE OF CORRECTION

PATENT NO. : 9,089,476 B2
APPLICATION NO. : 13/571026
DATED : July 28, 2015
INVENTOR(S) : Olivier Soula et al.

It is certified that error appears in the above-identified patent and that said Letters Patent is hereby corrected as shown below:

Claims

In Col. 63, line 15, Claim 1 "$q*m \leq 2$," should be ---$q*m \geq 2$---.

In Col. 63, line 67, Claim 1 "$3 \geq q \geq 50$;" should be ---$3 \leq q \leq 50$;---.

In Col. 64, line 24, Claim 4 "$-(f-[A]-COON)_n$" should be --- $-(f-[A]-COOH)_n$---.

Signed and Sealed this
Twelfth Day of January, 2016

Michelle K. Lee
*Director of the United States Patent and Trademark Office*